United States Patent [19]

Lee et al.

[11] Patent Number: 5,693,657
[45] Date of Patent: Dec. 2, 1997

[54] HETEROCYCLIC-SUBSTITUTED ALKYL AMIDE ACAT INHIBITORS

[75] Inventors: Helen Tsenwhei Lee, Ann Arbor; Patrick Michael O'Brien, Stockbridge; Joseph Armand Picard, Ypsilanti; Claude Forsey Purchase, Jr.; Bruce David Roth, both of Ann Arbor; Drago Robert Sliskovic, Ypsilanti; Andrew David White, Lakeland, all of Mich.

[73] Assignee: Warner-Lambert Company, Morris Plains, N.J.

[21] Appl. No.: 786,062

[22] Filed: Jan. 21, 1997

Related U.S. Application Data

[62] Division of Ser. No. 433,776, May 3, 1995, which is a division of Ser. No. 274,088, Jul. 12, 1994, Pat. No. 5,441,975, which is a division of Ser. No. 19,411, Feb. 18, 1993, Pat. No. 5,366,987, which is a continuation of Ser. No. 913,643, Jul. 20, 1992, abandoned, which is a continuation of Ser. No. 748,568, Aug. 22, 1991, abandoned.

[51] Int. Cl.$^6$ .................. A61K 31/44; C07D 401/06
[52] U.S. Cl. .................. 514/340; 514/381; 546/276; 548/253
[58] Field of Search .................. 514/340, 381; 546/276; 548/253

[56] References Cited

U.S. PATENT DOCUMENTS

| | | | |
|---|---|---|---|
| 3,152,140 | 10/1964 | Zeultz | 260/307 |
| 3,296,304 | 1/1967 | Tilley et al. | 260/558 |
| 3,505,349 | 4/1970 | Beaman et al. | 260/309 |
| 4,044,144 | 8/1977 | Sellstedt et al. | 548/253 |
| 4,072,498 | 2/1978 | Moon et al. | 71/92 |
| 4,160,829 | 7/1979 | Heijboer et al. | 424/246 |
| 4,663,323 | 5/1987 | Uchida et al. | 514/227 |
| 4,783,487 | 11/1988 | Brune | 514/563 |
| 4,826,868 | 5/1989 | Wachter et al. | 514/407 |
| 5,059,614 | 10/1991 | Lepage et al. | 514/378 |
| 5,073,566 | 12/1991 | Lifer et al. | 514/381 |
| 5,258,397 | 11/1993 | Lepage et al. | 514/380 |
| 5,312,726 | 5/1994 | Mihayashi et al. | 430/544 |

FOREIGN PATENT DOCUMENTS

| | | |
|---|---|---|
| 0035046 | 9/1981 | European Pat. Off. . |
| 0295631 | 11/1991 | German Dem. Rep. . |
| 4040619A | 12/1990 | Germany . |
| 2135996 | 9/1984 | United Kingdom ........ 548/247 |
| WO8603199 | 6/1986 | WIPO . |
| 9117150 | 11/1991 | WIPO . |
| WO9206948 | 4/1992 | WIPO . |

OTHER PUBLICATIONS

*Bull. Soc. Chim. Belg.*, vol. 96/n° Mar. 1987, pp. 225–228, Essassi et al.
*J. Org. Chem.*, 1984, 49, 5247–5250, Chang-Kyu Kim, et al.
Chem. Abst., 98(19) 154905J, 1982, Ahmad et al.
Ahmad et al. Clinical Abstract, 98(19), 154905J. 1982.

*Primary Examiner*—Yogendra N. Gupta
*Attorney, Agent, or Firm*—Todd M. Crissey

[57] ABSTRACT

Pharmaceutically useful compounds having ACAT inhibitory activity of the formula

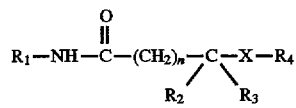

wherein n is 0, 1, or 2, for X other than tetrazole and n=2 then $R_2=R_3=H$; $R_1$ is phenyl, substituted phenyl, naphthyl, substituted naphthyl, a heteroaromatic group or a hydrocarbon group having from one to 18 carbon atoms; $R_2$ and $R_3$ are hydrogen, halo, hydroxy, alkyl, alkenyl, cycloalkyl, phenyl, substituted phenyl, a heteroaryl, or form a spiroalkyl group; X is a heteromonocyclic 5-membered ring containing one to four heteroatoms, said heteroatoms being nitrogen, oxygen or sulfur, and combination thereof; and $R_4$ is a hydrocarbon group having from one to 20 carbon atoms are described as well as methods of their manufacture.

10 Claims, No Drawings

HETEROCYCLIC-SUBSTITUTED ALKYL AMIDE ACAT INHIBITORS

CROSS-REFERENCE TO RELATED APPLICATION

This application is a divisional application of application Ser. No. 08/433,776, filed May 3, 1995, now allowed; which is a divisional application of U.S. Ser. No. 08/274,088, filed Jul. 12, 1994, now U.S. Pat. No. 5,441,975, issued Aug. 15, 1995; which is a divisional application of U.S. Ser. No. 08/019,411, filed Feb. 18, 1993, now U.S. Pat. No. 5,366,987, issued Nov. 22, 1994; which is a continuation of U.S. Ser. No. 07/913,643, filed Jul. 20, 1992, now abandoned; which is a continuation of U.S. Ser. No. 07/748,568, filed Aug. 22, 1991, now abandoned.

The present invention describes a series of novel heterocyclic-substituted alkyl amides which inhibit acyl-CoA:cholesterol acyltransferase (ACAT), the enzyme responsible for the esterification of dietary cholesterol. Such agents may decrease the absorption of dietary cholesterol and therefore provide a therapy for individuals with hypercholesterolemia.

SUMMARY OF THE INVENTION

The compounds of the present invention can be described by the following general formula $$R_1-NH-C(=O)-(CH_2)_n-\underset{R_2}{\overset{R_3}{C}}-X-R_4 \quad \text{Formula I}$$

wherein n is 0, 1, or 2, for X other than tetrazole and n=2 then $R_2=R_3=H$;

wherein $R_1$ is selected from (a) phenyl which is unsubstituted or is substituted with from one to three substituents selected from:
  alkyl having from one to four carbon atoms and which is straight or branched,
  alkoxy having from one to three carbon atoms and which is straight or branched,
  alkylthio having from one to three carbon atoms and which is straight or branched,
  phenyl,
  hydroxy,
  fluorine,
  chlorine,
  bromine,
  nitro,
  cyano,
  trifluoromethyl,
  —COOH,
  —COOalkyl wherein alkyl has from one to four carbon atoms and which is straight or branched,
  —(CH$_2$)$_m$NR$_5$R$_6$ wherein m is 0 or 1, and each of R$_5$ and R$_6$ is hydrogen or a straight or branched alkyl group having one to four carbon atoms;

(b) 1- or 2-naphthyl which is unsubstituted or substituted with one to three substituents selected from:
  alkyl having from one to four carbon atoms and which is straight or branched,
  alkoxy having from one to three carbon atoms and which is straight or branched,
  hydroxy,
  fluorine,
  chlorine,
  bromine,
  nitro,
  cyano,
  trifluoromethyl,
  —COOH,
  —COOalkyl wherein alkyl has from one to four carbon atoms and is straight or branched,
  —(CH$_2$)$_m$NR$_5$R$_6$ wherein m, R$_5$, and R$_6$ have the meanings defined above;

(c) the group

[structure with $R_8$, $R_9$, $R_{10}$ on a diazole ring]

wherein $R_8$ and $R_9$ are straight or branched alkyl having from one to four carbon atoms or phenyl, and $R_{10}$ is a straight or branched hydrocarbon group having from one to 18 carbon atoms which is saturated or is unsaturated containing one double bond or two nonadjacent double bonds; phenyl; phenyl substituted with from one to three substituents selected from straight or branched alkyl having one to four carbon atoms, straight or branched alkoxy having from one to three carbon atoms, hydroxy, fluorine, chlorine, bromine, nitro, cyano, trifluoromethyl, —COOH, —COOalkyl wherein alkyl has from one to four carbon atoms and is straight or branched or (CH$_2$)$_m$N$_5$R$_6$ wherein m, R$_5$, and R$_6$ are as defined above; or a heterocyclic group selected from 2-, 3-, or 4-pyridyl, 2-, 4-, or 5-pyrimidinyl, 2- or 3-pyrazinyl, 2-, 3-, 4-, 5-, 6-, 7-, or 8-quinolinyl, or 3- or 4-pyridazinyl and the N-oxides thereof;

(d) the group

[structure: quinoline with CH$_3$ groups]

(e) the group

[structure: biphenyl/quinoline with Cl and CH$_3$ groups]

(f) a straight or branched hydrocarbon group having from one to 18 carbon atoms which is saturated or is unsaturated containing one double bond or two nonadjacent double bonds;

(g) a cycloalkyl group having from three to eight carbon atoms;

(h) the group

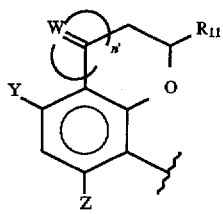

wherein — denotes a single or double bond; Y and Z are each independently hydrogen, a straight or branched alkyl group of one to four carbon atoms, an alkoxy group of one to three carbon atoms, or halo;
W is oxygen or two hydrogen atoms;
$R_{11}$ is hydrogen or a straight or branched alkyl group of one to four carbon atoms, and n' is 0 or 1; or (i) is selected from the group

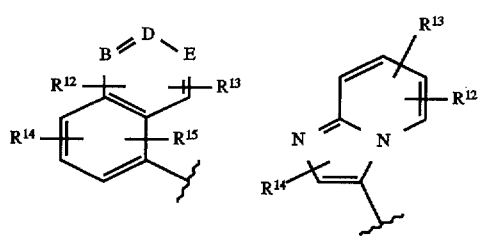

and

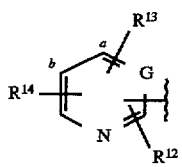

wherein $R^{12}$, $R^{13}$, $R^{14}$, and $R^{15}$ are each independently hydrogen, halo, a straight or branched alkyl group of one to four carbon atoms, an alkoxy group of one to three carbon atoms, an alkylthio group of one to three carbon atoms, cycloalkylthio of five to seven carbon atoms, phenylalkylthio in which alkyl is one to four carbon atoms, substituted phenylthio, heteroarylthio, or heteroaryloxy; and B, D, E, and G are nitrogen or carbon where one or more of B, D, and E is nitrogen; with the proviso that when G=N the group is attached to the nitrogen atom of Formula I at the four or five position of the pyrimidine ring (a and b), wherein $R_2$ and $R_3$ are the same or different and are selected from:

(a) hydrogen or halo (or hydroxy when X=tetrazole);

(b) a straight or branched alkyl group having from one to 12 carbon atoms, or a cycloalkyl group having from three to eight carbon atoms;

(c) a phenyl or phenylalkyl group where alkyl is from one to four carbon atoms and which the phenyl ring is unsubstituted or substituted with from one to three substituents selected from straight or branched alkyl having from one to four carbon atoms, straight or branched alkoxy having from one to four carbon atoms, alkylthio (straight or branched) having one to four carbon atoms, hydroxy, fluorine, chlorine, bromine, trifluoromethyl, cyano, nitro, phenyl, cycloalkyl, or $(CH_2)_m N_5 R_6$ wherein m, $R_5$, and $R_6$ have the meanings defined above;

(d) a straight or branched alkenyl group having from two to six carbon atoms; or (e) $R_2$ and $R_3$ taken together with the carbon atom to which they are attached form an alkylidene group of one to four carbon atoms, a benzylidene group or a spiroalkyl group having from three to seven carbon atoms;

(f) when $R_2$ is hydrogen, F, alkyl of $C_1$-12 atoms, $R_3$ can be heteroaryl selected from a 5- or 6-membered monocyclic or fused bicyclic heterocyclic group containing at least one to four heteroatoms in at least one ring, said heteroatoms being nitrogen, oxygen, or sulfur and combinations thereof, said heterocyclic group being unsubstituted or substituted with an alkyl group having from one to four carbon atoms and the N-oxides thereof; or (g) 1- or 2-naphthyl which is unsubstituted or substituted with one to three substituents selected from:
alkyl having from one to four carbon atoms and which is straight or branched, and
alkoxy having from one to three carbon atoms and which is straight or branched, wherein X is a 5-membered heteromonocyclic group containing at least one to four heteroatoms, said heteroatoms being nitrogen, oxygen, or sulfur and combinations thereof, said heteromonocyclic group being unsubstituted or substituted at any available position along the ring with $R_4$. Such a heterocyclic group includes, for example, pyrazole, isoxazole, isothiazole, oxazole, thiazole, imidazole, furan, thiophene, pyrrole, tetrazole, 1,2,3-triazole, 1,2,4-oxadiazole, 1,3,4-oxadiazole, 1,3,4-thiadiazole, 1,2,4-triazole, and 1,2,4-oxadiazole;

wherein $R_4$ is a straight or branched hydrocarbon chain having from one to 20 carbon atoms and is saturated or is unsaturated and has one double bond or has two nonadjacent double bonds or is alkyl substituted with trifluoromethyl or phenyl; is alkoxy having one to 20 carbon atoms and is saturated or unsaturated and has one double bond or has two nonadjacent double bonds; is alkylthio having one to 20 carbon atoms and is saturated; or is phenyl or phenyl substituted with one or more of the following: hydroxy, fluorine, chlorine, bromine, nitro, cyano, trifluoromethyl or —COOalkyl wherein alkyl has from one to four carbon atoms and which is straight or branched; pharmaceutically acceptable salts and individual enantiomeric isomers of the compounds.

DETAILED DESCRIPTION

Pharmaceutically acceptable salts of the compounds of Formula I are also included as a part of the present invention. Suitable acids for forming acid salts of the compounds of Formula I containing a basic group include, but are not necessarily limited to acetic, benzoic, benzenesulfonic, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. Additional acids for use to form acid salts of the compounds of Formula I include, but are not necessarily limited to, those acids found in Tables 3 and 4 of Grant & Hackh's Chemical Dictionary, Fifth Edition, 1987:11–13. The acid addition salts are formed by procedures well known in the art.

Certain compounds of the present invention may also exist in different isomeric forms, specifically stereoisomeric forms, by virtue of the presence of asymmetric centers in the compound. The present invention contemplates all stereoisomers that may be obtained, if desired, by methods known in the art as, for example, the separation of stereoisomers by chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

Illustrative examples of straight or branched saturated hydrocarbon chains having from one to 20 carbon atoms include methyl, ethyl, n-propyl, isopropyl, n-butyl, isobutyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon chains having from one to 20 carbon atoms and having one double bond or two nonadjacent double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having one to three carbon atoms include methoxy, ethoxy, n-propoxy, and isopropoxy.

Straight or branched alkyl groups having from one to four carbon atoms include, for example, methyl, ethyl, n-propyl, isopropyl, t-butyl, and n-butyl.

Cycloalkyl groups having from three to eight carbon atoms which $R_1$ may represent are cyclopropyl, cyclobutyl, cyclopentyl, cyclohexyl, cycloheptyl, and cyclooctyl.

Halo is fluoro, chloro, bromo, or iodo, but preferably fluoro.

A 5- or 6-membered monocyclic or fused bicyclic heterocycle is a monocyclic or fused bicyclic aromatic ring containing at least one to four heteroatoms in at least one ring, such as nitrogen, oxygen, or sulfur, or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycles containing a nitrogen atom.

More specifically, such a heterocycle may be a 2- or 3-thienyl; 2- or 3-furanyl; 2-, 3-, or 4-pyridyl or 2-, 3-, or 4-pyridinyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5-tetrazolyl; 3- or 5-(1,2,4)-triazolyl; 4- or 5-(1,2,3)-triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

Preferred compounds of this invention, wherein X is a tetrazole, are those wherein the $R_4$ substituent group is attached to the 2-position of the tetrazole moiety and the side chain or remainder of the molecule is attached to the carbon atom of the tetrazole moiety, the 5-position. Compounds wherein n is 0, or one when $R_2=R_3=H$ are also preferred with compounds wherein n is 0 being more preferred. Compounds wherein $R_1$ is other than naphthyl or substituted naphthyl are also preferred. Compounds wherein n is 0, $R_1$ is substituted phenyl, and $R_2$ (or $R_3$, but not both) is phenyl or substituted phenyl, and $R_4$ is in the 2-position of a tetrazole moiety and has from 8 to 18 carbon atoms are most preferred.

Most preferred are compounds of Formula I wherein. $R_1$ is 2,6-(1-methylethyl)phenyl or 2,4,6-trimethoxy-phenyl; n is 0; $R_2$ and $R_3$ are each independently hydrogen, methyl, fluoro, cyclohexyl, or phenyl, X is a 5-membered ring heterocycle (e.g., tetrazole, pyrazole, 1,2,4-oxadiazole), and $R_4$ is in the 2-position if X is a tetrazole ring and has 12 carbon atoms.

As shown by the data presented below in Table I, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, *Biochemica et Biophysica Acta* 1982;712:557–570. The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes (designated IAI) or from rat liver microsomes (designated LAI).

These data, as they relate to compounds when X is a tetrazole, appear in Tables I and III where they are expressed as $IC_{50}$ values; i.e., the concentration of test compound required to inhibit the activity of the enzyme by 50%.

TABLE I

| Example | IAI $IC_{50}$ (µM) |
|---|---|
| 1 | 0.003 |
| 2 | 0.092 |
| 3 | 0.007 |
| 5 | 0.01 |
| 6 | 0.12 |
| 7 | 0.028 |
| 9 | 0.28 |
| 11 | 0.017 |
| 13 | 0.009 |
| 14 | 0.091 |
| 15 | 0.008 |
| 16 | 0.008 |
| 17 | 0.19 |
| 18 | 0.028 |
| 19 | 0.014 |
| 20 | 0.047 |
| 21 | 0.015 |
| 22 | 0.091 |
| 23 | 0.0075 |
| 24 | 0.041 |
| 25 | 0.08 |
| 26 | 0.079 |
| 27 | 0.014 |
| 28 | 0.018 |
| 29 | 0.010 |
| 30 | 0.77 |
| 31 | 0.27 |
| 32 | 0.053 |
| 33 | 0.017 |
| 34 | 0.069 |
| 35 | 0.009 |
| 36 | >5 |
| 37 | 0.21 |
| 38 | 0.059 |
| 41 | 0.025 |

TABLE I-continued

| Example | IAI IC$_{50}$ (µM) |
|---|---|
| 44 | 0.029 |
| 45 | 0.23 |
| 46 | 11 |
| 47 | 2.1 |
| 48 | 0.12 |
| 49 | 0.015 |
| 50 | 1 |
| 51 | 0.66 |
| 52 | 0.036 |
| 53 | 0.097 |
| 54 | 0.22 |
| 55 | 0.026 |
| 56 | 0.20 |
| 58 | 0.031 |
| 59 | 0.049 |
| 60 | 0.028 |
| 61 | 0.31 |
| 62 | 0.014 |
| 65 | 0.015 |
| 66 | 0.020 |
| 111 | 0.040 |
| 112 | 0.019 |
| 113 | 0.025 |
| 114 | 0.016 |
| 115 | 0.22 |
| 116 | 0.41 |
| 117 | 0.054 |
| 118 | 1.76 |
| 119 | 0.17 |
| 121 | 0.014 |

In one in vivo screen designated APCC, male Sprague-Dawley rats (200 to 225 g) were randomly-divided into treatment groups and dosed at 4 PM with either vehicle (CMC/Tween) or suspensions of compounds in vehicle. The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table II. The compounds were dosed at 30 mg/kg unless otherwise noted.

TABLE II

| Example | APCC (% ΔTC) |
|---|---|
| 1 | −64 |
| 2 | −32 |
| 3 | −39 |
| 5 | −60 |
| 6 | −37 |
| 7 | −1 |
| 9 | −44 |
| 11 | −41 |
| 13 | −63 |
| 14 | −33 |
| 15 | −66 |
| 16 | −56 |
| 17 | −8 |
| 18 | +15 |
| 19 | −62 |
| 20 | −62 |
| 21 | −61 |
| 22 | −22 |
| 23 | −52 |
| 24 | −56 |
| 25 | −61 |

TABLE II-continued

| Example | APCC (% ΔTC) |
|---|---|
| 26 | −44 |
| 27 | −69 |
| 29 | −56 |
| 31 | −39 |
| 32 | −47 |
| 33 | −55 |
| 34 | −22 |
| 35 | −60 |
| 36 | −13 |
| 37 | −17 |
| 38 | −60 |
| 41 | −65 |
| 44 | −66 |
| 45 | −60 |
| 46 | +4 |
| 47 | −4 |
| 48 | −37 |
| 49 | −51 |
| 50 | −34 |
| 51 | −62 |
| 53 | −59 |
| 54 | −43 |
| 55 | −64 |
| 56 | −57 |
| 60 | −63 |
| 61 | −64 |
| 62 | −68 |
| 66 | −61 |
| 111 | −54 |
| 112 | −46 |
| 113 | −59 |
| 114 | −57 |
| 115 | −49 |
| 116 | −23 |
| 117 | −75 |
| 118 | −44 |
| 119 | |
| 121 | |

Compounds of Formula I where the amide side chain is attached directly to a nitrogen atom of a tetrazole ring were also active in the above described tests and the results are shown in Table III.

TABLE III

| Example | IAI (IC$_{50}$) (µM) | APCC (% ΔTC) |
|---|---|---|
| 88 | 0.010 | −62 |
| 89 | 0.390 | −35 |
| 90 | 0.10 | +5 |
| 91 | 0.006 | −68 |
| 92 | 0.015 | −77 |
| 93 | 0.022 | −30 |
| 94 | 0.029 | −26 |
| 95 | 0.058 | −64 |
| 96 | 0.19 | −47 |
| 97 | 0.056 | −69 |
| 98 | 0.021 | −65 |
| 99 | 0.032 | −51 |
| 100 | 0.080 | −63 |
| 101 | >5.0 | +8 |
| 102 | 0.042 | −47 |
| 103 | 0.049 | −60 |
| 104 | 0.055 | −50 |
| 109 | >1.0 | −19 |
| 110 | 0.017 | −75 |

Data indicating that compounds of the present invention, wherein X is not a tetrazole, are potent inhibitors of ACAT is presented in Table IV. Where they are expressed as IC$_{50}$ values; i.e., the concentration of test compound required to inhibit the activity of the enzyme by 50%.

TABLE IV

| Example | LAI IC$_{50}$ (µM) |
| --- | --- |
| 122 | 0.046 |
| 123 | 0.044 |
| 125 | 0.110 |
| 126 | 0.022 |
| 127 | 0.032 |
| 128 | 0.015 |
| 129 | 0.022 |
| 130 | 0.019 |
| 131 | 0.024 |
| 132 | 0.051 |
| 133 | 0.10 |
| 134 | 0.017 |
| 135 | 0.014 |
| 136 | 0.14 |
| 137 | 0.031 |
| 138 | 0.031 |

Following the procedure discussed previously, in another in vivo screen designated APCC, male Sprague-Dawley rats (200–225 g) were randomly divided into treatment groups and dosed at 4 PM with either vehicle (CMC/Tween) or suspensions of compounds in vehicle. The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table V. The compounds were dosed at 30 mg/kg unless otherwise noted.

TABLE V

| Example | APCC (% ΔTC) |
| --- | --- |
| 122 | −68 |
| 123 | −72 |
| 125 | −62 |
| 126 | −69 |
| 127 | −59 |
| 128 | −68 |
| 129 | −72 |
| 130 | −52 |
| 132 | −50 |
| 133 | −29 |
| 134 | −57 |
| 135 | −64 |
| 136 | −27 |
| 137 | −54 |

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention can be prepared by various routes all of which are generally known in the art. The compounds of Formula I wherein n is 0, each of $R_2$ and $R_3$ is hydrogen, X is a tetrazole, and $R_1$ and $R_4$ are as defined in Formula I can be prepared as set forth in Chart I hereof.

In Chart I, the tetrazole ester (2) is synthesized via treatment of ethyl cyanoacetate (1) with sodium azide. Alkylation of the tetrazole ester (2) with a halide of the formula $R_4$ halo (3) wherein $R_4$ has the meaning defined in Formula I and halo is, e.g., bromine or chlorine, provides a mixture of (4) and (7), i.e., the 2- and 1-regioisomers, respectively, isomers which are separable by chromatography. Esters (4) and (7) can then be independently hydrolyzed to the acids (5) and (8) which are coupled with an amine of the formula $R_1NH_2$ wherein $R_1$ has the meaning defined in Formula I using carbonyldiimidazole in THF to give the 2 and 1 substituted tetrazole amides (6) and (9), respectively.

Compounds of Formula I wherein n is 0, X is a tetrazole, and $R_1$, $R_2$, $R_3$, and $R_4$ are as defined in Formula I except that both $R_2$ and $R_3$ are not hydrogen and $R_3$ is other than heteroaryl or naphthyl are best synthesized employing the synthetic sequence presented in Chart II. In Chart II the ethyl cyanoacetate derivatives (11) are treated with tri-n-butyltin azide in dioxane at reflux to give compound (12) after acidic hydrolysis with HCl in ether or tetrahydrofuran. The tetrazole is then alkylated with a halide of the formula $R_4$ halo, wherein $R_4$ has the meaning defined in Formula I and halo is chlorine or bromine, in acetonitrile at reflux using a base such as triethylamine or pyridine. The resulting 2- and 1-regioisomers compounds (13) and (14)] are separated by chromatography. Compound (13) is easily hydrolyzed to carboxylic acid (15) when treated with NaOH or KOH in an alcoholic solvent such as methanol or ethanol at room temperature. However, when $R_2$ is hydrogen and $R_3$ is alkyl, aryl, or alkenyl, regioisomer (14) decarboxylates to (17) when subjected to the previously described hydrolytic conditions. The desired acid (19) is obtained under these conditions, however, when $R_2=R_3=H$ or $R_2$ and $R_3$ is alkyl, alkenyl, aryl, or spirocycloalkyl. The carboxylic acids (15, 19) are easily converted to the corresponding amides (16, 18) when treated with a coupling agent such as carbonyldiimidazole or dicyclohexylcarbodiimide in tetrahydrofuran or dichloromethane and an appropriate amine of the formula $R_1NH_2$ wherein $R_1$ has the meaning defined in Formula I. Alternatively, regioisomer (18) is prepared by treating (17) with n-butyllithium in tetrahydrofuran at $-20°$ C. followed by the addition of an appropriate isocyanate ($R_1NCO$).

Also when $R_2=H$ in Compound 15 (Chart II(a)), Compound 15 may be deprotonated using n-BuLi in THF at $-78°$ C. to give an anion Which can then be treated with an electrophilic reagent ($R_2X$) to give the $\alpha,\alpha'$-disubstituted acid shown which can then be coupled with an appropriate amine ($R_1NH_2$) in a manner as previously described to yield the corresponding amides. Also when Compound 13 (Chart II), $R_2=H$, $R_3$ as defined in Formula I, this ester can also be deprotonated and the anion fluorinated using N-fluorobenzenesulfonimide to yield the $\alpha$-fluoro ester which is then used as described in the text for Compound 13.

Compounds of formula (11) are either commercially available or can be synthesized employing the following conditions:

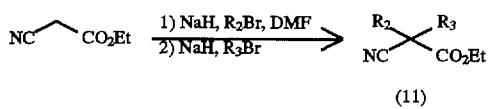

(11)

Ethyl cyanoacetate is treated with one equivalent of sodium hydride in dimethylformamide or tetrahydrofuran followed by the addition of an appropriate alkylating agent such as 1-bromopropane or benzyl bromide to give the monoalkylated analog. Similarly, a second equivalent of base may then be added followed by the addition of an appropriate alkylating agent to give disubstituted ethyl cyanoacetates of formula (11). The compounds of Formula I wherein n is 0, $R_2$ is hydrogen, $R_3$ is heteroaryl, 1- or 2-naphthyl, substituted phenyl, X is a tetrazole, and $R_1$ and $R_4$ are as defined in Formula I are prepared as shown in Chart VI hereof wherein the reaction conditions are set forth. Specific Example 38 is illustrative of this synthetic route. The acetonitriles, $R_3CH_2CN$, are known in the art or are prepared from the alcohol, $R_3CH_2OH$, by procedures generally known in the art, e.g., *J. Am. Chem. Soc.* 1949; (71):3994. Spirocycloalkyl analogues are synthesized in a similar manner by employing dihalo alkyl halides of the formula halo-$(CH_2)_p$-halo wherein p is two to six and halo is chlorine or bromine as the alkylating agent. An illustrative alkylating agent is 1,4-dibromobutane. Compounds of Formula I wherein n=0, $R_2$, $R_3$=alkyl, aryl, X is a tetrazole, $R_1$, $R_4$ as defined in Formula I can also be synthesized as shown in Chart XI. The commercially available acetonitriles are treated with tri-n-butyltin azide in dioxane at reflux to give the corresponding tetrazoles which are then alkylated with a primary alkyl halide in acetonitrile at reflux using a base such as TEA or pyridine. The resulting 1- and 2-regioisomers are separated by chromatography. Treatment of these compounds with n-butyllithium in tetrahydrofuran at $-78°$ C. followed by the addition of an appropriate isocyanate ($R_1NCO$) gives the desired amides. Specific Example 46 is illustrative of this synthetic route. Additionally compounds of Formula I wherein n=0, $R_2$, and/or $R_3$ is F or OH, X is a tetrazole, $R_1$, $R_4$ as defined in Formula I can be synthesized as shown in Chart XII. The alkylated tetrazole is treated with n-BuLi and TMEDA in THF at $-78°$ C. followed by an $\alpha$-keto ester. The resulting hydroxy compound was then treated with diethyl amino sulfur trifluoride (DAST) in dichloromethane at $-78°$ C. under $N_2$. The resulting fluoro ester was then hydrolyzed using NaOH in methanol/water. The resulting acid was converted to the acid chloride via treatment with oxalyl chloride in dichloromethane at room temperature. The crude acid. chloride was treated with an appropriate amine in dichloromethane with $Et_3N$ as base at $0°$ C. to yield the desired amide. Specific Example 65 is illustrative of this synthetic route. Also the hydroxyester may be treated with t-butyldimethyl silyl trifluoromethane sulfonate in dichloromethane with $Et_3N$ as base to yield the protected hydroxy ester, which can then be converted to the desired amide as shown in the scheme.

The compounds of Formula I wherein n is one or two, $R_2$ and $R_3$ are hydrogen, X is a tetrazole, and $R_1$ and $R_4$ are as defined in Formula I are prepared as set forth in Chart III hereof. In Chart III an appropriate nitrile ester (20) is heated with an alkali metal azide, such as $LiN_3$ or $NaN_3$, and $NH_4Cl$ in dimethylformamide at temperatures ranging from $50°$ to $80°$ C. to give after work-up the corresponding tetrazole ester (20-A). The tetrazole ester (20-A) is heated, typically at temperatures between $50°$ and $100°$ C., with a tertiary amine such as triethylamine, and an appropriate alkyl halide, including alkyl bromides, chlorides, and iodides, or an arylalkyl halide in a polar solvent, such as $CH_3CN$, to give after work-up and chromatographic separation both of the corresponding regioisomeric 1-alkylated and 2-alkylated tetrazole esters (22) and (21). The alkyl tetrazole esters (21 and 22) are stirred, typically at temperatures between $0°$ and $30°$ C., with alkali metal hydroxides, such as LiOH, NaOH, or KOH, in an alcoholic solvent such as methanol or ethanol for 1 to 24 hours to give after work-up the corresponding alkyltetrazole carboxylic acids (23 and 24). The alkyltetrazole carboxylic acids are coupled with primary amines, especially aryl amines of the formula $R_1NH_2$ wherein $R_1$ is as defined in Formula I such as 2,4,6-trimethoxyaniline, 2,6-diisopropylaniline, and 2,4-difluoroaniline, using a carboxylic acid activating reagent such as carbonyldiimidazole or dicyclohexylcarbodiimide in an aprotic solvent such as THF or $CH_2Cl_2$, at temperatures between $-10°$ and $+110°$ C. to give after work-up the corresponding alkyltetrazole amides (25 and 26).

The compounds of general Formula I wherein n is one, $R_2$ is hydrogen, $R_3$ is phenyl, substituted phenyl, heteroaryl, alkyl, or alkenyl, X is a tetrazole, and $R_1$ and $R_4$ are as defined in Formula I are prepared as set forth in Chart IV. In Chart IV the group $R_3$ is phenyl, substituted phenyl or heteroaryl as defined in Formula I or $R_3$ is a straight or branched alkyl having from 1 to 6 carbon atoms or a straight or branched alkenyl having from 2 to 6 carbon atoms. The β-substituted cyanopropionic acid compound (27) is prepared from the corresponding aldehyde of the formula $R_3CHO$ using the procedure described in U.S. Pat. No. 4,760,089. Compound (27) is treated with an appropriate amine, $R_1NH_2$ wherein $R_1$ has the meaning defined in Formula I employing a coupling agent such as carbonyldiimidazole in tetrahydrofuran at room temperature or dicyclohexylcarbodiimide in dichloromethane at 0° C. to give the nitrile amide (28). The nitrile amide (28) is converted to the tetrazole (29) by treatment with $(n-Bu)_3SnN_3$ in refluxing dioxane and then is alkylated with an appropriate compound of the formula $R_4halo$ wherein $R_4$ has the meaning defined in Formula I and halo is chlorine, or bromine employing triethylamine in acetonitrile. The products (30) and (31) are separated by chromatography. Specific Example 45 is illustrative of this synthetic route.

The compounds of Formula I wherein n is two, $R_2$ is hydrogen, $R_3$ is phenyl or substituted phenyl, and X is a tetrazole are prepared as set forth in Chart V. Compound (32) is prepared according to the method of Paganelli (*Tett. Lett.* 1991;32:2807–2810) by a transition metal catalyzed Michael addition of benzyl cyanide to methyl acrylate. Compound (32) is then treated with $(n-Bu)_3SnN_3$ in refluxing dioxane to give the tetrazole (33), which is then alkylated with-an alkyl halide, $R_4halo$, e.g., $R_4Br$, wherein $R_4$ is as defined in Formula I, in acetonitrile employing $Et_3N$ as base, giving a mixture of regioisomers (34) and (35) which are separated by flash chromatography. Hydrolysis of each ester with ethanolic NaOH at room temperature gives the respective acids (36) and (38). The acids are then coupled with an appropriate amine of the formula $R_1NH_2$ wherein $R_1$ is as defined in Formula I employing carbonyldiimidazole in tetrahydrofuran at room temperature or dicyclohexylcarbodiimide in $CH_2Cl_2$ at 0° C. as coupling agent to give the amides (37) and (39).

The compounds of Formula I wherein n is one, $R_3$ is other than heteroaryl, X is a tetrazole, and $R_1$, $R_2$, and $R_4$ are as defined in Formula I are prepared as set forth in Chart VII.

Ethyl cyanoacetate is alkylated (or dialkylated) by treatment with NaH in an appropriate solvent such as dimethylformamide or tetrahydrofuran at from 0° to 25° C. to give the alkylated nitrile (40). The nitrile is then treated with $(n-Bu)_3SnN_3$ in dioxane at reflux for 24 hours to give after acidic hydrolysis the tetrazole (41) which is then alkylated with an alkyl halide $(R_4Br)$ in $CH_3CN$ employing $Et_3N$ as base to give a mixture of regioisomers (42) and (43). The regioisomers are separated by flash chromatography and each ester is reduced by DIBAL-H in $CH_2Cl_2$ or toluene at −78° C. to give the corresponding alcohols (44) and (45). The alcohols are treated with methanesulfonyl chloride in $CH_2Cl_2$ using triethylamine as a base at 0° C. to give the corresponding mesylates which are then treated with KCN in dimethylformamide or dimethyl sulfoxide at 100° C. to give the corresponding nitriles (46) and (47). These are then hydrolyzed to the corresponding acids (48) and (49) by treatment with ethanolic NaOH (or KOH) at reflux. The acids are then coupled with an appropriate amine employing carbonyldiimidazole in tetrahydrofuran at room temperature or dicyclohexylcarbodiimide in $CH_2Cl_2$ at 0° C. to give the amides (50) and (51).

The compounds of Formula I wherein n is one, $R_3$ is heteroaryl, X is a tetrazole, and $R_1$ and $R_4$ are as defined in Formula I are prepared in the same manner as set forth in Chart VII beginning with compounds which are the same as compounds (42) and (43) except that $R_2$ is hydrogen and $R_3$ is heteroaryl. These comparable tetrazole intermediates are prepared as set forth in Chart VIII hereof wherein $R_3$ is heteroaryl and $R_4$ has the meaning defined in Formula I. The reaction conditions are set forth in Chart VIII.

The compounds of Formula I wherein n is two, $R_2$ and $R_3$ are as defined in Formula I only at least one is other than hydrogen, X is a tetrazole, and $R_1$ and $R_4$ are as defined in Formula I are prepared as set forth in Chart IX.

Malonitrile is alkylated (or dialkylated) by treatment with NaH in an appropriate solvent such as dimethylformamide or tetrahydrofuran at 0° to 25° C. to give compounds (51). Treatment of the substituted nitrile with $(n-Bu)_3SnN_3$ in refluxing dioxane for 24 hours gives, after acidic hydrolysis, the tetrazole (52), which is then alkylated with an alkyl halide $(R_4Br)$ in $CH_3CN$ employing $Et_3N$ as base to give a mixture of regioisomers (53) and (54). The regioisomers are then separated by flash chromatography and each nitrile is then reduced to the corresponding aldehydes (55) and (56) by treatment with Raney nickel in formic acid at 60° C. The resulting aldehydes are then treated with a stabilized ylide such as ethyl(triphenylphosphoranylidene)acetate in $CH_2Cl_2$ at room temperature to give (57) and (58) which are reduced catalytically using hydrogen gas, Pd/C as catalyst in methanol or ethanol at room temperature to give esters (59) and (60). These are then hydrolyzed to the corresponding acids (61) and (62) by treatment with alcoholic (MeOH/EtOH) alkali metal hydroxide (NaOH or KOH) at reflux. The acids are then coupled with an appropriate amine employing carbonyldiimidazole in tetrahydrofuran at room temperature or dicyclohexylcarbodiimide in $CH_2Cl_2$ at 0° C. to give amides (63) and (64).

The N-oxides of compounds of this invention are prepared by standard procedures known in the art, for example, by treatment with m-perchlorobenzoic acid at reflux in chloroform or dichloromethane.

The isocyanates, $R_1NCO$, and the amines $R_1NH_2$ wherein $R_1$ has the meaning defined in Formula I, employed in preparing the compounds of this invention are known in the art or can be prepared by procedures generally known in the art. For example, the pyrazole amines are prepared as set forth in Chart X hereof wherein the reaction conditions are indicated in the chart.

In addition, compounds of Formula I having an asymmetric carbon atom can be synthesized in either enantiomeric form ($R_2$ does not equal $R_3$) by treating compounds (15) or (19) in Chart II, (27) in Chart IV, (36) or (38) in Chart V, (48) or (49) in Chart VII, and (61) or (62) in Chart IX with appropriate chiral amines such as R-(+)- or S-(−)-α-methylbenzyl amine, (1S, 2R) ephedrine, or brucine.

Whereas the charts provided herein, including but not limited to Charts II, IV, V, VII, IX, XIII–XVI, XVIII–XIX, XXIa, XXIII, and XXIV–XXVII, illustrate specific examples of acids containing a chiral center, it should be pointed out that one skilled in the art would know of other acids containing a chiral center that may be obtained by known procedures and employed in the present invention. Some of the acid types include, but are not limited to, the acids previously discussed with regard to forming acid addition salts (see Grant & Hackh's Chemical Dictionary, Fifth Edition, 1987:11–13).

The salts above are prepared by dissolving the racemic acid enumerated above in ethyl acetate or a mixture of hexane/ethyl acetate containing the appropriate chiral amine. The chiral salt is collected by filtration and recrystallized several times from hexane/ethyl acetate. The chiral acid is then liberated through an acidic workup and its enantiomeric purity is determined by chiral HPLC. The chiral acids are then coupled with appropriate amines to give enantiomerically pure compounds designated as (16), (18), (28), (37), (39), (50), (51), (63), and (64), respectively. Similarly, to obtain the chiral products of the compounds of formulas (67) and (68) in Chart VI the intermediates (65) and (66) are treated with n-BuLi and ethyl chloroformate as shown in Chart VIII and the resulting esters are hydrolyzed to obtain acids corresponding to (48) and (49). These acids are then treated with chiral amines as described above.

For compounds of Formula I where the amide side chain is attached on a nitrogen atom of the tetrazole ring (Chart XIII), a nitrile ($R_4CN$) is converted to the corresponding 5-substituted tetrazole by cycloaddition with an azide (ammonium azide, tributyltin azide, etc) in an inert solvent such as dimethylformamide. The resulting 5-substituted tetrazole can be alkylated with an α-bromo ester using a base such as triethylamine in a neutral solvent such as acetonitrile. The resulting mixture of 1,5 and 2,5 regioisomers is separated by chromatography or recrystallization. The esters of the pure regioisomers are then individually saponified. using an inorganic base (NaOH, KOH, etc) and acidified with a mineral acid such as HCl to give the corresponding carboxylic acids. The carboxylic acids are coupled with various amines ($R_1NH_2$) using standard coupling reagents (CDI, DCC, mixed anhydride, etc) to give the final products.

With respect to the compounds of the present invention, wherein X is not a tetrazole, these compounds can also be prepared by various routes all of which are generally known in the art. The compounds of Formula I wherein n is 0, X is pyrazole, and $R_1$, $R_2$, $R_3$, and $R_4$ are as defined in Formula I can be prepared as set forth in Chart XIV hereof. The preferred embodiment is shown where the alkylamide moiety is attached to either pyrazole nitrogen atom.

In Chart XIV, pyrazole is alkylated with an alkyl halide which possesses a masked carboxylic acid group (i.e., an ester or a nitrile). The pyrazole is then formylated using standard Vilsmeier-Haack formylation conditions to give the 4-formyl pyrazole. Wittig reaction of this aldehyde with the ylid generated from the appropriately substituted phosphonium salt gives a 4-vinyl pyrazole (predominantly of the Z configuration). Base hydrolysis (NaOH/EtOH) of the ester gives the free acid which can be coupled to an amine ($R_1NH_2$) using standard amide bond forming reactions (i.e., DCC, CDI, acid chloride, etc) to give the desired pyrazole amides. The alkene in the 4-position of the pyrazole may be hydrogenated to give the desired pyrazole amides with a saturated alkyl chain.

The compounds of Formula I wherein n is 0, X is imidazole, and $R_1$, $R_2$, $R_3$, and $R_4$ are as defined in Formula I can be prepared as set forth in Chart XV, XXII, and XXIII hereof. In Chart XV, Wittig reaction of N-protected 4-formyl imidazole with the ylid generated from the appropriately substituted phosphonium salt gives a 4-vinyl imidazole (predominantly the Z configuration). The 4-alkene group can optionally be reduced using standard hydrogenation methods. The protected imidazole is then deprotected to give the corresponding 4-alkyl or 4-alkenyl imidazole. The imidazole is then alkylated with an alkyl halide which possesses a masked carboxylic acid group (i.e., an ester or a nitrile). Base hydrolysis of the ester gives the free acid which can be coupled to an amine ($R_1NH_2$) using standard amide bond forming reactions (i.e., DCC, CDI, acid chloride, etc) to give the desired imidazole amides where the alkylamido moiety is connected to the 1 position of the imidazole ring.

The compounds of Formula I wherein n is 0, X is imidazole, $R_2$ and $R_3$ are hydrogen, and $R_1$ and $R_4$ are as defined in Formula I can be prepared as set forth in Chart XXII hereof. In Chart XXII, the imidazole ring is constructed via cyclization of dihydroxyacetone and an imino ester. The imidazole is then protected as the benzyl derivative. The alcohol functionality is converted by standard techniques to the carboxylic acid homologue (halide displacement, nitrile displacement, acid hydrolysis) which is coupled with an amine ($R_1NH_2$)and deprotected to yield the imidazole amide ($R_2$, $R_3$=H where the alkylamide moiety is connected to the 4-position of the imidazole ring).

The compounds of Formula I wherein n is 0, X is imidazole, $R_3$ is hydrogen, and $R_1$, $R_2$, and $R_4$ are as defined in Formula I can be prepared as set forth in Chart XXIII hereof. In Chart XXIII, the protected imidazole (see Chart XII) is oxidized and a Grignard reagent added to yield the substituted alcohol. The alcohol functionality is then elaborated via standard techniques (halide displacement, nitrile displacement, acid hydrolysis, amine Coupling ($R_1NH_2$) and deprotection) to yield the amide.

The compounds of Formula I wherein n is 0, X is 1,2,3-triazole and $R_1$, $R_2$, $R_3$, and $R_4$ are as defined in Formula 1 can be prepared as set forth in Chart XVI hereof. In Chart XVI, cycloaddition of an alkyne to an azide gives a 4-substituted 1,2,3-triazole. The triazole is alkylated with an alkyl halide which possesses a masked carboxylic acid group (i.e., an ester or a nitrile) to give a mixture of regioisomers (1,4-, 2,4-, and 1,5-substituted 1,2,3-triazoles). Chromatographic separation affords the pure regioisomers. Base hydrolysis of the esters gives the free acids which can be coupled to an amine using standard amide bond forming reactions (i.e., DCC, CDI, acid chloride, etc) to give the desired 1,2,3-triazole amides.

The compounds of Formula I wherein n is 0, X is isoxazole, $R_2$ and $R_3$ are hydrogen, and $R_1$ and $R_4$ are as defined in Formula I can be prepared as set forth in Chart XVII hereof. In Chart XVII, condensation of a ketone with diethyloxalate in the presence of base yields an enolate which is cyclized under acidic conditions to give a 5-isoxazole carboxylic acid. Homologation is then achieved via reduction to the alcohol conversion to the bromide, debromination to yield the methyl isoxazole and finally deprotonation, and quenching with carbon dioxide, to yield 5-isoxazole acetic acid. The acid can be coupled to an amine ($R_1NH_2$) using standard techniques to give the desired isoxazole amides.

The compounds of Formula I wherein n is 0, X is isoxazole, $R_3$ is hydrogen, and $R_1$, $R_2$, and $R_4$ are as defined in Formula I can be prepared as set forth in Chart XVIII hereof. In Chart XVIII, a trimethyl silyl enolate is prepared from a methyl ketone using standard techniques, then quenched with an aldehyde ($R_2R_3CHCHO$) in the presence of a Lewis acid to give an aldol product which can be oxidized to a 1,3-diketone under standard Swern conditions. Cyclization of the 1,3-diketone with hydroxylamine yields a mixture of isoxazoles which are deprotonated and quenched with $CO_2$ to give the acids, subsequent coupling with an amine ($R_1NH_2$) under standard conditions yields the amides which are separable by column chromatography.

In charts XVIIIa and XVIIIb the regiospecific synthesis of the isoxazole amides is described. A nitroalkane is prepared from the bromide via displacement with sodium nitrite. A 3+2 cycloaddition of nitrile oxide (generated in situ via dehydration of nitroalkane) and an acetylene yields an isoxazole. Subsequent deprotonation and quenching with isocyanate yields the 3-alkyl-5-acetamido-isoxazole. Chart XVIIIb describes the synthesis of the 5-alkyl-3-acetamido-isoxazole prepared similarly via a 3+2 cycloaddition using the appropriate acetylene and nitrile oxide.

The compounds of Formula I wherein n is 0, X is 1,3,4-oxadiazole, $R_3$ is hydrogen, and $R_1$, $R_2$, and $R_4$ are as defined in Formula I can be prepared as set forth in Chart XIX hereof. In Chart XIX, the α-anion of an ester ($R_2R_3CHCO_2Et$) is added to an isocyanate ($R_1NCO$) to yield the amido acetic acid ester. Hydrolysis of the ester and coupling with an acyl hydrazide under standard conditions yields a 1,2-diacylhydrazide which can be dehydrated to the 1,3,4-oxadiazole using $P_2O_5$-EtOH.

The compounds of Formula I wherein n is 0, X is thiazole, $R_1$, $R_2$, $R_3$, and $R_4$ are as defined in Formula I can be prepared as set forth in Chart XX hereof. In Chart XX, the thioamide is prepared via standard conditions by conversion of an acid chloride to an amine, then treatment with $P_2S_5$ yields a thioamide which is cyclized with an α-haloketone to yield a thiazole ester which is hydrolysed to the acid and coupled with an amine ($R_1NH_2$) under standard conditions to give the thiazole amide. The α-haloketone may be purchased ($R_1R_2$=H) or synthesized via silyl ketene acetal addition to chloroacetyl chloride (Chart XX).

The compounds of Formula I wherein n is 0, X is 1,2,4-oxadiazole, $R_3$ is hydrogen, and $R_1$, $R_2$, and $R_4$ are as defined in Formula I can be prepared as set forth in Charts XXIa and XXIb hereof. In Charts XXIa and XXIb, the regioisomeric 1,2,4-oxadiazoles are synthesized. In Chart XXIa, an amido acetic acid derivative (Chart XIX) is coupled with an N-hydroxyamidine, the intermediate is then cyclized by acid to yield the 3-alkyl-5-acetamido-oxadiazole. The N-hydroxyamidine is synthesized under standard conditions from the nitrile. In Chart XXIb the 5-alkyl-1,2,4-oxadiazole-3-acetamide regioisomer is prepared via addition of an α-anion of a nitrile to an isocyanate ($R_1NCO$). The amido-acetonitrile derivative is then converted to the N-hydroxyamidine via reaction with hydroxyamine, coupled with an acid chloride ($R_4COCl$) and cyclized under acidic conditions to give the oxadiazole.

The compounds of Formula I wherein n is 0, X is oxazole, $R_3$ is hydrogen, and $R_1$, $R_2$, and $R_4$ are as defined in Formula I can be prepared as set forth in Chart XXIV hereof. In Chart XXIV, allyl amine is protected as the BOC-derivative then epoxidized under standard conditions. The epoxide is then opened with a Grignard reagent ($R_4MgBr$) or organolithium and the resultant alcohol oxidized to the protected aminoketone. Deprotection and formation of the acid salt is achieved in one step to give an amino ketone which is cyclized with an acid (Synthesized in chart XIX) to give the oxazole.

The compounds of Formula I wherein n is 0, X is thiophene, $R_2$ is phenyl, $R_3$ is hydrogen, and $R_1$ and $R_4$ are as defined in Formula I can be prepared as set forth in Chart XXV hereof. In Chart XXV, the thiophene ring is constructed via cyclization of a 1,4-diketone with $H_2S$. The 1,4-diketone is obtained from a Stetter reaction of vinyl ketone and aldehyde. The thiophene intermediate is elaborated via deprotonation, quenching with $CO_2$ and coupling of the acid with an amine ($R_1NH_2$) under standard conditions to give the thiophene amide.

The compounds of Formula I wherein n is 0, X is pyrrole, $R_2$ is phenyl, $R_3$ is hydrogen, and $R_3$ and $R_4$ are as defined in Formula I can be prepared as set forth in Chart XXVI hereof. In Chart XXVI, the pyrrole ring is constructed via cyclization of a 1,4-diketone with ammonium acetate. The 1,4-diketone is obtained from a Stetter reaction of vinyl ketone and aldehyde. The pyrrole intermediate is elaborated via protection, deprotonation, quenching with $CO_2$, coupling of the acid with an amine ($R_1NH_2$) under standard conditions and deprotection to give the pyrrole amide.

The compounds of Formula I wherein n is 0, X is furan, $R_3$ is hydrogen, and $R_1$, $R_2$, and $R_4$ are as defined in Formula I can be prepared as set forth in Chart XXVII hereof. In Chart XXVII, furaldehyde is elaborated via Wittig reaction, and subsequent reduction of the double bond to yield the $R_4$ substituent. α-Deprotonation of the furan and quenching with an aldehyde gives an alcohol. The alcohol functionally is then elaborated via standard techniques (halide displacement, nitrile displacement, acid hydrolysis, amine coupling with an appropriate $R_1NH_2$) to yield the furan amide.

The compounds of Formula I wherein n is 0, X is 1,3,4-thiadiazole, $R_3$ is hydrogen, and $R_1$, $R_2$, and $R_4$ are as defined in Formula I can be prepared as set forth in Chart XXVIII hereof. In Chart XXVIII, an ester is converted to a diacylhydrazide via reaction with hydrazine and then an acid chloride ($R_4COCl$). The intermediate is then cyclized to the 1,2,4-thiadiazole with $P_4S_{10}$. The amide functionally is installed via deprotonation and quenching with an isocyanate ($R_1NCO$).

EXAMPLE 1

N-[2,6-Bis(1-methylethyl)phenyl]-2-dodecyl-2H-tetrazole-5-acetamide ($R_1$=2,6-diisopropylphenyl; n is 0; $R_2$ and $R_3$ are hydrogen; and $R_4$ is 2-$(CH_2)_{11}CH_3$.

(a) Tetrazoleacetic acid ethyl ester

To a solution of ethylcyanoacetate (20.0 g, 0.177 mol) in dimethylformamide (DMF) (180 mL) was added $NH_4Cl$ (10.4 g, 0.19 mol) and sodium azide (12.6 g, 0.19 mol) sequentially. The mixture was heated for 5 hours at 100° C., allowed to cool, and the DMF removed in vacuo. The residue was taken up in water (150 mL), acidified to pH 2 with concentrated HCl, and filtered. The filtrate was cooled to 5° C. and allowed to crystallize. The solid was filtered, dried in vacuo over self-indicating silica gel to give 10.61 g, 42%, mp 124°–129° C.

(b) 1-Dodecyltetrazoleacetic acid ethyl ester and 2-Dodecyltetrazole acetic acid ethyl ester 1-Bromododecane (8.78 g, 0.035 mol) was added to a refluxing solution of the tetrazole acetic acid ethyl ester (5.0 g, 0.032 mol) obtained in (1a) above, and triethylamine (3.56 g, 0.035 mol) in acetonitrile (150 mL). The mixture was refluxed for 18 hours, allowed to cool, and filtered. The filtrate was concentrated in vacuo and partitioned between ethyl acetate (150 mL) and wager (150 mL). The organic layer was washed with brine (100 mL) and dried over $MgSO_4$, then filtered, concentrated, and chromatographed on silica gel, eluting with 10%, then 20% ethyl acetate in hexanes to give 5.40 g, 52% of the 2-isomer (Rf 0.66, 50% ethyl acetate/hexane) as an oil and 3.39 g, 33% of the 1-isomer (Rf 0.50, 50% ethyl acetate/hexane) as a solid, mp 59°–62° C.

(c) 2-Dodecyltetrazoleacetic acid

A solution of KOH (4.21 g, 0.075 mol) in water (10 mL) was added to a solution of the 2-dodecyltetrazole acetic acid ethyl ester (23.2 g, 0.0715 mol) in ethanol (250 mL). The mixture was stirred at room temperature for 3 hours, concentrated in vacuo to ~50 mL, diluted with water (200 mL), and washed with ethyl acetate (100 mL). The aqueous layer was acidified with 1.0M HCl and extracted with ethyl acetate. The organic layer was dried over $MgSO_4$, filtered, and concentrated to give 18.0 g, 85% of a white solid, mp 70°–73° C.

(d) N-[2,6-Bis(1-methylethyl)phenyl]-2-dodecyl-2H-tetrazole-5-acetamide

Carbonyldiimidazole (5.74 g, 0.035 mol) was added to a solution of the 2-dodecyltetrazole acetic acid (10.0 g, 0.034 mol) obtained in (c) above in dry THF (100 mL) under an inert atmosphere ($N_2$). The mixture was stirred at room temperature for 30 minutes, then 2,6-diisopropylaniline (6.7 mL, 0.038 mol) was added in one portion. The resulting solution was stirred for 3 days at room temperature, concentrated in vacuo, taken up in dichloromethane (200 mL), washed with water (100 mL) and brine (100 mL), and dried over $Na_2SO_4$. The dried solution was filtered, concentrated, and chromatographed on silica gel, eluting with 15% ethyl acetate in hexanes to give 10.6 g, 68% of the title compound as an off-white solid, mp 75°–79° C.

EXAMPLE 2

N-[2,6-Bis(1-methylethyl)phenyl]-1-dodecyl-1H-tetrazole-5-acetamide (R=2,6-diisopropylphenyl; n is 0; $R_2$ and $R_3$ are hydrogen; and $R_4$ is 1-$(CH_2)_{11}CH_3$.

Following the procedure set forth in steps (c) and (d) of Example 1, only substituting 1-dodecyl-tetrazoleacetic acid ethyl ester for 2-dodecyl-tetrazoleacetic acid ethyl ester, the title compound was obtained, mp 88°–91° C.

Following the general procedure of Examples 1 and 2 only substituting an appropriate amount of the amine listed below for 2,6-diisopropylaniline, the respective products listed below were obtained.

| Example | Amine | Product |
| --- | --- | --- |
| 3 | 4,6-dimethoxy-pyrimidin-5-ylamine | N-(4,6-dimethoxy-5-pyrimidinyl)-2-dodecyl-2H-tetrazole-5-acetamide |
| 4 | 4,6-dimethoxy-pyrimidine-5-ylamine | N-(4,6-dimethoxy-5-pyrimidinyl)-2-dodecyl-1H-tetrazole-5-acetamide |
| 5 | 2,4,6-trimethoxy-aniline | 2-dodecyl-N-(2,4,6-trimethoxyphenyl)-2H-tetrazole-5-acetamide, mp 117–118° C. |
| 6 | 2,4,6-trimethoxy-aniline | 1-dodecyl-N-(2,4,6-trimethoxyphenyl)-1H-tetrazole-5-acetamide, mp 108–109.5° C. |
| 7 | 3-methylpyridin-2-ylamine | 2-dodecyl-N-(3-methyl-2-pyridinyl)-2H-tetrazole-5-acetamide, mp 63–65° C. |
| 8 | 3-methylpyridin-2-ylamine | 1-dodecyl-N-(3-methyl-2-pyridinyl)-1H-tetrazole acetamide |
| 9 | 2,4-difluoroaniline | N-(2,4-difluorophenyl)-2-dodecyl-2H-tetrazole-5-acetamide, mp 79–80° C. |
| 10 | 2,4-difluoroaniline | N-(2,4-difluorophenyl)-1-dodecyl-1H-tetrazole-5-acetamide |
| 11 | 1,3,5-trimethyl-1H-pyrazol-4-ylamine | 2-dodecyl-N-(1,3,5-trimethyl-1H-pyrazol-4-yl)-2H-tetrazole-5-acetamide, mp 95–97° C. |
| 12 | 1,3,5-trimethyl-1H-pyrazol-4-ylamine | 1-dodecyl-N-(1,3,5-trimethyl-1H-pyrazol-4-yl)-1H-tetrazole-5-acetamide |

The compounds of Example 9 and 10 above were made as a mixture.

EXAMPLE 13

(±) 2-Dodecyl-α-phenyl-N-(2,4,6-trimethoxyphenyl)-2H-tetrazole-5-acetamide (a) (±) α-Phenyl tetrazole-5-acetic acid, ethyl ester Ethyl phenylcyanoacetate (44.4 g; 0.23 moles) was dissolved in p-dioxane (900 mL) and treated with n-tributyltin azide (76.3 g; 0.23 moles) in one portion. The solution was heated to reflux for hours, cooled to room temperature, and then concentrated in vacuo. The resulting liquid was dissolved in ethyl ether (500 mL) and treated with gaseous HCl for over 15 minutes. The ether was removed in vacuo leaving a viscous liquid which solidified when triturated with boiling hexanes. Yield: 47.29 (88%).

$^1$H NMR (DMSO-$D_6$) δ7.3 (s, 5H), 5.7 (s, 1H), 4.2 (q, 2H), 1.1 (t, 3H) ppm.

(b) (±) 2-Dodecyl-α-phenyl-2H-tetrazole-5-acetic acid, ethyl ester

The tetrazole ester (a) (47 g; 0.20 moles) was dissolved in acetonitrile (550 mL) containing one equivalent of triethylamine (20.2 g; 0.20 moles). The solution was heated to reflux and then 1-bromododecane (49.8 g; 0.20 moles) was added dropwise over 20 minutes. Upon completion, the solution was heated to reflux for 16 hours, cooled to room temperature, and concentrated in vacuo. The residue was triturated with ethyl acetate (1L), filtered, and the filtrate was washed with aqueous HCl (1N), brine, and dried over magnesium sulfate. The drying agent was removed by filtration and the solvent concentrated in vacuo, leaving a viscous liquid containing both 1- and 2-isomers. The regioisomers were separated by silica gel chromatography using 75% hexane and 25% ethyl acetate as the eluent, obtaining the title compound as a colorless liquid. Yield: 33 g (41%).

$^1$H NMR (CDCl$_3$) δ7.5 (d, 2H), 7.3 (m, 3H), 5.3 (s, 1H), 4.5 (t, 2H), 4.2 (m, 2H), 2.0 (m, 2H), 1.2 (s, 18H), 0.8 (t, 3H) ppm.

(c) (±) 1-Dodecyl-α-phenyl-1H-tetrazole-5-acetic acid, ethyl ester

The 1-dodecyl compound was isolated from the silica gel column previously described in isolating compound (b) above. Yield: 14.3 g (18%).

$^1$H NMR (CDCl$_3$) δ7.2–7.4 (m, 5H), 5.3 (s, 1H), 4.2 (q, 2H), 4.0 (t, 2H), 1.5 (m, 2H), 1.2 (s, 18H), 0.8 (t, 3H) ppm.

(d) (±) 2-Dodecyl-α-phenyl-2H-tetrazole-5-acetic acid

Compound (c) (33.0 g; 0.082 moles) obtained above was dissolved in absolute ethanol (400 mL) and treated with sodium hydroxide pellets (6.5 g; 0.16 moles) in one portion. The solution was stirred for several hours at room temperature before concentrating the ethanol in vacuo, leaving a viscous syrup. The carboxylic acid sodium salt was dissolved in water (300 mL) and washed with one portion of ethyl ether (75 mL). The aqueous solution was then acidified to a pH of 1.0 with concentrated HCl, and the product was extracted with two portions of ethyl acetate. The combined organic solution was washed once with brine, dried over MgSO$_4$, and filtered. The filtrate was concentrated in vacuo, leaving a colorless liquid that solidified on standing, mp 55°–57° C. Yield: 27.8 g (91%).

$^1$H NMR (DMSO-D$_6$) δ7.4 (d, 2H), 7.3 (m, 3H), 5.4 (s, 1H), 4.6 (t, 2H), 1.8 (m, 2H), 1.2 (s, 18H), 0.8 (s, 3H) ppm.

(e) (±) 2-Dodecyl-α-phenyl-N-(2,4,6-trimethoxyphenyl)-2H-tetrazole-5-acetamide

The compound obtained in (d) above (6.58 g; 17.6 mmoles) was dissolved in tetrahydrofuran (50 mL), treated with carbonyldiimidazole (3.1 g; 19.1 mmoles), and stirred for 1 hour at room temperature under an atmosphere of N$_2$. A solution of 2,4,6-trimethoxyaniline (3.2 g; 17.6 mmoles/ 50 mL THF) was then added in one portion and the solution was stirred at room temperature for overnight. Ethyl acetate (150 mL) was then added as well as aqueous HCl (1N). The layers were separated and the organic portion was washed with NaOH (1N), brine, and then dried over MgSO$_4$. The drying agent was filtered and the filtrate concentrated in vacuo leaving a lavender colored solid which was purified by silica gel chromatography using chloroform (95%)/ methanol (5%) as the eluent. Yield: 6.7 g (70%), mp 119°–120° C.

When in the procedure of Example 13(e) an appropriate amount of the amine listed below was substituted for 2,4,6-trimethoxyaniline and the general procedure of Example 13(e) was followed, the respective products listed below were obtained.

| Example | Amine | Product |
| --- | --- | --- |
| 14 | Aniline | (±)-2-dodecyl-N,α-diphenyl-2H-tetrazole-5-acetamide, mp 74–76° C. |
| 15 | 2,6-diisopropylaniline | (±)-N-[2,6-bis(1-methylethyl)phenyl]-2-dodecyl-α-phenyl-2H-tetrazole-5-acetamide, $^1$H NMR(CDCl$_3$) δ 7.9 (s, 1H), 7.5(d, 2H), 7.4(m, 3H), 7.2(t, 1H), 7.1(d, 2H), 5.5 (s, 1H), 4.6(t, 2H), 2.8(m, 2H), 2.0(m, 2H), 1.3(s, 18H), 1.0 (d, 12H), 0.8(t, 3H) ppm. |
| 16 | 4,6-dimethoxy-pyrimidin-5-ylamine | (±)-N-(4,6-dimethoxy-5-pyrimidinyl)-2-dodecyl-α-phenyl-2H-tetrazole-5-acetamide, $^1$H NMR(CDCl$_3$) δ 8.3 (s, 1H), 7.9(bs, 1H), 7.5(d, 2H), 7.3(q, 3H), 5.4(s, 1H), 4.6 (t, 2H), 3.9(s, 6H), 2.0(m, 2H), 1.3(s, 18H), 0.8(t, 3H) ppm. |
| 17 | 5,7-dimethyl-1,8-naphthyridine-2-ylamine | (±)-N-(5,7-dimethyl-1,8-naphthyridine-2-yl)-2-dodecyl-α-phenyl-2H-tetrazole-5-acetamide, mp 148–149° C. |
| 18 | 3-amino-4-(2-chlorophenyl)-6,8-dimethyl quinoline | (±)-N-[4-(2-chloro phenyl)-6,8-dimethyl-3-quinolinyl]-2-dodecyl-α-phenyl-2H-tetrazole-5-acetamide, $^1$H NMR(CDCl$_3$) δ 9.0 (d, 1H), 7.1–7.6(m, 11H), 5.6(s, 1H), 4.6 (tr, 2H), 2.8(s, 3H), 2.3(s, 3H), 1.9(tr, 2H), 1.2(s, 18H), 0.9 (m, 3H) ppm. |
| 19 | 1,3,5-trimethyl-1H-pyrazol-4-ylamine | (±)-2-dodecyl-α-phenyl-N-(1,3,5-trimethyl-1H-pyrazol-4-yl)-2H-tetrazole-5-acetamide, $^1$H NMR (CDCl$_3$) δ 7.7 (bs, 1H), 7.4(d, 2H), 7.2 (m, 4H), 5.4(s, 1H), 4.6(t, 3H), 3.6(s, 3H), 2.0(d, 6H), 1.3 (s, 18H), 0.8(t, 3H) ppm. |
| 20 | cyclopropylamine | (±)-N-cyclopropyl-2-dodecyl-α-phenyl-2H-tetrazole-5-acetamide, $^1$H NMR(CDCl$_3$) δ 7.3–7.4(m, 5H), 6.7(bs, 1H), 5.2(s, 1H), 4.6 (s, 3H), 2.7(m, 1H), 2.0(m, 2H), 1.3(s, 18H), 0.8(t, 3H), 0.7 (m, 2H), 0.4(m, 2H) ppm. |
| 21 | 2,4-difluoroaniline | (±)-N-(2,4-difluoro-phenyl)-2-dodecyl-α-phenyl-2H-tetrazole-5-acetamide, $^1$H NMR (CDCl$_3$) δ 8.9(bs, 1H), 8.3(m, 1H), 7.5 (dd, 2H), 7.4(m, 3H), 6.9(m, 2H), 5.4(s, 1H), 4.6(t, 2H), 2.0 (m, 2H), 1.2(s, 18H), 0.8(t, 3H) ppm. |
| 22 | 2-pyridinylamine | (±)-2-dodecyl-α-phenyl-N-2-pyridinyl-2H-tetrazole-5-acetamide, $^1$H NMR (CDCl$_3$) δ 9.0(bs, 1H), 8.2(m, 2H), 7.6 (t, 1H), 7.5(d, 2H), 7.3(m, 3H), 7.0(m, 1H), 5.4(s, 1H), 4.6 (t, 2H), 2.0(m, 2H), 1.3(s, 18H), 0.8(t, 3H) ppm. |
| 23 | 3-methylpyridin-2-ylamine | (±)-2-dodecyl-N-(3-methyl-2-pyridinyl)-α-phenyl-2H-tetrazole-5-acetamide, $^1$H NMR (CDCl$_3$) δ 8.7(bs, 1H), 8.2(d, 1H), 7.5 (t, 3H), 7.3(q, 3H), 7.0(m, 1H), 5.5(s, 1H), 4.6(t, 2H), 2.1 (s, 3H), 2.0(m, 2H), 1.3(s, 18H), 0.8(t, 3H) ppm. |

EXAMPLE 24

(±)-2-Dodecyl-N-(3-methyl-2-pyridinyl)-2-phenyl-2H-tetrazole-5-acetamide, N-oxide The compound of Example 23 (0.50 g; 1.0 mmole) was dissolved in dichloromethane and then treated with MCPBA (0.22 g; 1.1 mmole) in one portion and stirred at room temperature for 12 hours. The resulting 3-chlorobenzoic acid byproduct was removed by washing the organic solution with aqueous potassium carbonate and then brine. The dichloromethane was dried over magnesium sulfate, filtered, and concentrated in vacuo, leaving a white precipitate. The crude product was triturated with ethyl ether and collected by filtration.

¹H NMR (CDCl₃) δ9.7 (bs, 1H), 8.1 (d, 1H), 7.6 (d, 2H), 7.3 (q, 3H), 7.1 (d, 1H), 7.0 (t, 1H), 5.5 (s, 1H), 4.6 (t, 2H), 2.2 (S, 3H), 2.0 (m, 2H), 1.3 (s, 18H), 0.8 (t, 3H) ppm.

EXAMPLE 25

(±)-N-(2,4-Difluorophenyl)-1-dodecyl-α-phenyl-1H-tetrazole-5-acetamide (a) 5-Benzyl-1-dodecyl-1H-tetrazole (±)-1-Dodecyl-α-phenyl-1H-tetrazole-5-acetic acid, ethyl ester, i.e., the compound of Example 13(c) (14 g; 0.034 mmoles) was dissolved in absolute ethanol (175 mL) and treated with sodium hydroxide pellets (2.7 g; 0.069 mmoles). The solution was stirred for 30 minutes forming a gelatinous precipitate. The solid was removed by filtration, dissolved in water, and then acidified to a pH of 1.0 using concentrated HCl. The precipitate was collected by filtration and washed with water. Yield: 8.5 g (76%), mp 50°–51° C.

(b) (±)-N-(2,4-Difluorophenyl)-1-dodecyl-α-phenyl-1H-tetrazole-5-acetamide

The compound from (a) above (1.5 g; 4.5 mmoles) was dissolved in tetrahydrofuran (20 mL), cooled to −20° C., and then treated dropwise with n-butyllithium (2.8 mL; 4.5 mmoles) for over 5 minutes. The solution was stirred for 5 minutes before adding 2,4-difluorophenyl isocyanate (0.7 g; 4.5 mmoles). The ice bath was removed and the solution gradually warmed to room temperature over 30 minutes, at which time the reaction was quenched with water (20 mL) and diluted with ethyl acetate. The layers were separated and the organic portion was washed with aqueous HCl (1N), aqueous sodium carbonate (10%), and brine. The solution was dried over magnesium sulfate, filtered, and stripped to dryness leaving a viscous liquid that was dissolved in 75% hexane/25% ethyl acetate and chromatographed using silica gel. Yield: 0.9 g (41%).

¹H NMR (CDCl₃) δ10.1 (S, 1H), 8.1 (m, 1H), 7.3 (s, 5H), 6.8 (m, 2H), 5.2 (s, 1H), 4.2 (t, 2H), 1.6 (m, 2H), 1.2 (d, 18H), 0.8 (t, 3H) ppm.

EXAMPLE 26

(±)-N-[2,6-Bis(1-methylethyl)phenyl]-1-dodecyl-α-phenyl-1H-tetrazole-5-acetamide When in the procedure of Example 25(b) an appropriate amount of 2,6-diisopropylphenylisocyanate was substituted for 2,4-difluorophenylisocyanate and the general procedure of Example 25(b) was followed, the title compound was obtained, mp 113°–115° C.

EXAMPLE 27

2-Dodecyl-α,α-dimethyl-N-(2,4,6-trimethoxyphenyl)-2H-tetrazole-5-acetamide (a) Ethyl 2,2-dimethylcyanoacetate A solution of ethyl cyanoacetate (20 g; 0.17 moles) in tetrahydrofuran (350 mL) was cooled to −10° C. followed by the addition of sodium hydride (7.25 g; 0.17 moles) in several portions. The suspension was stirred for 10 minutes at −10° C. before adding iodomethane (23.3 g; 0.17 moles). The ice bath was removed and the solution gradually warmed to 20° C. for over 45 minutes. The solution was then recooled to −10° C. and a second equivalent of sodium hydride (7.25 g; 0.17 moles) was added, again, in small portions. Soon after, iodomethane (23.3 g; 0.17 moles) was added, the ice bath removed, and the solution stirred at room temperature for 2 hours before being quenched with H₂O. The product was extracted with ethyl ether (500 mL) and washed with brine, dried over MgSO₄, and the solution concentrated in vacuo, leaving a crude product that was purified by distillation.

Yield: 16.9 g, b.p. 82°–85° C.; 15 mm Hg.

(b) α,α'-Dimethyltetrazole-5-acetic acid, ethyl ester

Ethyl-2,2-dimethylcyanoacetate (a) (11.6 g; 0.082 moles) was dissolved in dioxane (240 mL) and treated with tri-n-butyltin azide (76.3 g; 0.23 moles) in one portion. The solution was refluxed for overnight, cooled to room temperature, and then concentrated in vacuo. The resulting liquid was dissolved in ethyl ether (500 mL) and treated with gaseous HCl continuously for 15 minutes. The ether was concentrated in vacuo, leaving a viscous liquid which gradually solidified on standing. Yield: 8.4 g.

¹H NMR (CDCl₃) δ12.2 (bs, 1H), 4.2 (q, 2H), 1.8 (s, 6H), 1.3 (5, 3H) ppm.

(c) 2-Dodecyl-α,α'-dimethyl-2H-tetrazole-5-acetic acid, ethyl ester

The compound obtained in (b) above (4.0 g; 0.021 moles) was dissolved in acetonitrile (50 mL) containing one equivalent of triethylamine (2.3 g; 0.021 moles). The solution was heated to reflux followed by the addition of 1-bromododecane (5.6 g; 0.022 moles). The solution was refluxed for 16 hours, cooled to room temperature, and then concentrated in vacuo. The residue was triturated with ethyl acetate. (250 mL), filtered, and the filtrate was washed with aqueous HCl (1N), brine, and dried over magnesium sulfate. Concentration of the solution after filtration afforded a viscous liquid containing both the 1- and 2-regioisomers. The latter isomer was obtained by silica gel chromatography using 75% hexane and 25% ethyl acetate as the eluant. The product was isolated as a colorless liquid (4.5 g).

¹H NMR (CDCl₃) δ4.5 (t, 2H), 4.1 (q, 2H), 1.9 (m, 2H), 1.7 (s, 6H), 1.2 (s, 18H), 0.9 (t, 3H) ppm.

(d) 2-Dodecyl-α,α'-dimethyl-2H-tetrazole-5-acetic acid

The compound obtained in (c) above (3.2 g; 0.009 moles) was dissolved in absolute ethanol (40 mL) and treated with sodium hydroxide pellets (0.38 g; 0.0095 moles) in one portion. The solution was stirred at room temperature for overnight before concentrating the ethanol in vacuo. The residue was dissolved in H₂O and acidified to a pH of 1.0. The product was extracted with ethyl acetate in two portions. The combined organic solution was washed with brine, dried over magnesium sulfate, and filtered. The filtrate was concentrated in vacuo leaving a colorless liquid that solidified on standing. Yield: 2.05 g.

¹H NMR (CDCl₃) δ4.5 (t, 2H), 2.0 (m, 2H), 1.7 (s, 6H), 1.2 (s, 18H), 0.9 (t, 3H) ppm.

(e) 2-Dodecyl-α,α'-dimethyl-N-(2,4,6-trimethoxy-phenyl)-2H-tetrazole-5-acetamide The carboxylic acid obtained in (d) above (2.0 g; 0.006 moles) was dissolved in dry THF (50 mL) and then treated with carbonyldiimidazole (1.0 g; 0.006 moles) in one portion. The solution was stirred for 1 hour under nitrogen before adding 2,4,6-trimethoxyaniline (1.0 g; 0.006 moles), also in one portion. The solution was stirred for 5 days under nitrogen and at room temperature. The solution was diluted with ethyl acetate and washed with aqueous HCl (1N), NaOH (1N), and brine. Magnesium sulfate was added as the drying agent and the solution filtered. The filtrate was concentrated in vacuo leaving a maroon-colored liquid. The crude product was purified by silica gel chromatography employing 75% hexane and 25% ethyl acetate as the eluant. Yield: 1.5 g colorless liquid.

¹H NMR (CDCl₃) δ7.2 (bs, 1H), 6.1 (s, 2H), 4.6 (t, 1H), 3.7 (d, 9H), 2.1 (m, 2H), 1.7 (s, 6H), 1.3 (s, 18H), 0.9 (t, 3H) ppm.

EXAMPLE 28

2-Dodecyl-α,α'-(2-propenyl)-N-(2,4,6-trimethoxyphenyl)-2H-tetrazole-5-acetamide

Following the general procedure of Example 27, only substituting ethyl-2,2-bis (allyl)cyanoacetate for ethyl-2,2-dimethylcyanoacetate in 27(a) and following the general procedure of 13(a) through 13(e) the title compound was obtained.

$^1$H NMR (CDCl$_3$) δ8.5 (bs, 1H), 6.1 (s, 2H), 5.7 (m, 2H), 5.0 (m, 4H), 4.6 (t, 2H), 3.7 (d, 9H), 3.0 (dd, 2H), 2.9 (dd, 2H), 1.9 (m, 2H), 1.2 (s, 18H), 0.8 (t, 3H) ppm.

EXAMPLE 29

1-(2-Dodecyl-2H-tetrazol-5-yl)-N-(2,4,6-trimethoxyphenyl)cyclopentanecarboxamide (a) 1,1-Dicyanocyclopentane Sodium hydride (37.8 g; 0.94 moles) was suspended in dimethylformamide (250 mL) under an atmosphere of N$_2$. A solution of malononitrile (30 g; 0.45 moles) and 1,4-dibromobutane 99.7 g; 0.45 moles) in dimethylformamide (150 mL) was added dropwise at such a rate so as not to exceed 30° C. The mixture was stirred for overnight, poured into H$_2$O (500 mL), and then washed with two portions of ethyl ether. The organics were combined, washed with brine, and dried over magnesium sulfate. The drying agent was removed by filtration and the filtrate was concentrated in vacuo, leaving a bilayered liquid. The lower portion was separated (28.8 g) and identified as the desired product.

$^1$H NMR (CDCl$_3$) δ2.4 (m, 4H), 2.0 (m, 4H) ppm.

(b) 5-Cyanocyclopentyl tetrazole

The compound obtained in (a) above (9.8 g; 0.082 moles) was dissolved in dioxane (240 mL) and treated with tri-n-butyltin azide (27.3 g; 0.082 moles) in one portion. The solution was refluxed overnight, cooled, and the dioxane removed in vacuo. The resulting liquid was taken up in ethyl ether and continuously treated with gaseous HCl for over 15 minutes. The ethereal solution was concentrated in vacuo leaving a viscous orange syrup. Yield: 11.0 g.

(c) 5-Cyanocyclopentyl-2-dodecyl-2H-tetrazole

The tetrazole (b) obtained above (11.0 g; 0.067 moles) was dissolved in acetonitrile (150 mL) containing one equivalent of triethylamine (6.8 g; 0.067 moles). The solution was heated to reflux followed by the addition of 1-bromo dodecane (16.8 g; 0.067 moles). Isolation of the 2-isomer was achieved employing the same conditions described for Example 11.

Yield: 7.5 g; colorless liquid.

$^1$H NMR (CDCl$_3$) δ4.6 (t, 2H), 2.5 (m, 4H), 2.0 (m, 6H), 1.3 (s, 18H), 0.9 (t, 3H) ppm.

(d) 2-Dodecyl-α,α-spirocyclopentyl-2H-tetrazole-5-acetic acid

The nitrile obtained in (c) above (7.5 g; 0.022 moles) was dissolved in absolute ethanol (150 mL) and treated with aqueous (50%) sodium hydroxide (18 g; 0.022 moles). The solution was refluxed for 4 hours, cooled to room temperature, and then concentration of the solvent in vacuo. The sodium salt was dissolved in H$_2$O, acidified to a pH of 1.0, and then the product was extracted with ethyl ether. The organic solution was dried over magnesium sulfate, filtered, and concentration of the solvent in vacuo leaving a viscous liquid which gradually solidified over several days. Yield: 5.8 g.

$^1$H NMR (CDCl$_3$) δ4.6 (t, 2H), 2.5 (m, 4H), 2.0 (m, 2H), 1.8 (m, 4H), 1.3 (s, 18H), 0.9 (t, 3H) ppm.

(e) 2-Dodecyl-α,α-spirocyclopentyl-N-(2,4,6-trimethoxyphenyl)-2H-tetrazole-5-acetamide The acid obtained in (d) above (1.5 g; 0.0042 moles) was dissolved in dichloromethane (50 mL), cooled to −10° C., and then treated with 2,4,6-trimethoxyaniline hydrochloride (0.94 g; 0.0042 moles). Soon after, triethylamine (0.43 g; 0.0042 moles) was added and then dicyclohexylcarbodiimide (0.88 g; 0.0042 moles) in one portion. This suspension gradually warmed to room temperature with stirring for overnight. The mixture was filtered and the filtrate was washed with aqueous HCl (1N), brine, dried over magnesium sulfate, and then filtered. Concentration of the solvent in vacuo afforded a viscous liquid that was dissolved in 50% ethyl acetate/50% hexane and purified by silica gel chromatography. Yield: 1.6 g colorless liquid.

$^1$H NMR (CDCl$_3$) δ7.3 (bs, 1H), 6.1 (s, 2H), 4.6 (t, 2H), 3.8 (d, 9H), 2.6 (m, 2H), 2.5 (m, 2H), 2.0 (m, 2H), 1.9 (m, 2H), 1.6 (m, 2H), 1.2 (s, 18H), 0.9 (t, 3H) ppm.

EXAMPLE 30

(±) N-(1,1-dimethylethyl )-2-dodecyl-α-phenyl-2H-tetrazole-5-acetamide

When in the procedure of Example 13(e) an appropriate amount of tert-butylamine was substituted for 2,4,6-trimethoxyaniline and the general procedure of Example 13(e) was followed, the title compound was obtained.

$^1$H NMR (CDCl$_3$) δ7.3 (m, 5H), 6.4 (bs, 1H), 5.1 (s, 1H), 4.6 (t, 2H), 2.0 (m, 2H), 1.3 (s, 18H), 1.2 (s, 9H), 0.9 (t, 3H) ppm.

EXAMPLE 31

(±)-2-Octyl-α-phenyl-N-(2,4,6-trimethoxyphenyl)-2H-tetrazole-5-acetamide

When in the procedure of Example 13(b) an appropriate amount of 1-bromooctane was substituted for 1-bromododecane and the general procedure of Example 13(b), (d), and (e) was followed, the title compound was obtained, mp 113°–116° C.

EXAMPLE 32

(±) 2-Hexadecyl-α-phenyl-N-(2,4,6-trimethoxyphenyl)-2H-tetrazole-5-acetamide

When in the procedure of Example 13(b) an appropriate amount of 1-bromohexadecane was substituted for 1-bromododecane and the general procedure of Example 13(b), (d), and (e) was followed, the title compound was obtained, mp 134°–135° C.

EXAMPLE 33

2-Tridecyl-α,α-dimethyl-N-(2,4,6-trimethoxyphenyl)-2H-tetrazole-5-acetamide

When in the procedure of Example 27(c) an appropriate amount of 1-bromotridecane was substituted for 1-bromododecane and the general procedure of Example 27(c), (d), and (e) was followed, the title compound was obtained.

$^1$H NMR (CDCl$_3$) δ7.5 (br.s, 1H), 6.05 (s, 2H), 4.6 (t, 2H), 3.8 (s, 3H), 3.75 (s, 6H), 1.8 (s, 6H), 1.2–1.4 (m, 22H), 0.9 (m, 3H) ppm.

EXAMPLE 34

2-Dodecyl-N-(2,4,6-trimethoxyphenyl)-2H-tetrazole-5-propanamide (a) A mixture of methyl 3-cyanopropanoate (27.3 g, 0.241 mol), NH$_4$Cl (11.5 g, 0.215 mol), and NaN$_3$ (13.9 g, 0.214 mol) in dimethylformamide (225 mL) was heated at 100° C. for 6 hours. The mixture was allowed to cool and filtered. The filtrate was concentrated in vacuo. The residue was dissolved in H$_2$O (200 mL). The solution was acidified with concentrated HCl (52 mL) and extracted with EtOAc (9×200 mL). The extracts were washed (saturated NaCl), dried (MgSO$_4$), and concentrated in vacuo to an oil; yield 29.2 g. The oil was dissolved in CH$_3$CN (590 mL) and Et$_3$N (29.5 mL, 0.21 mol). The solution was heated to 60° C. To this solution was added in one portion 1-bromododecane (49.5 mL, 0.21 mol), and the mixture was refluxed for 50 hours. The mixture was allowed to cool and filtered. The filtrate was concentrated in vacuo to a thick suspension, and the suspension was triturated with ether (500 mL). The ether was concentrated in vacuo to an oil, and the oil was chromatographed on silica gel (470 g, 70–230 mesh) using petroleum ether-EtOAc (15:1, 15×900 mL and 10:1, 20×900 mL) as eluent. A white solid was obtained; yield 12.0 g (15%) of methyl 2-dodecyl-2H-tetrazole-5-propanoate, mp 39°–42° C.

Chromatography gave a white solid; yield 8.64 g (11%) of methyl 1-dodecyl-1H-tetrazole-5-propanoate, mp 43°–45° C.

(b) To a stirred, room temperature solution of KOH (2.5 g) in absolute ethanol (210 mL) was added in one portion the 2-dodecyl-2H-tetrazole ester (11.5 g, 0.0354 mol), and the resulting solution was stirred for 3 days. The solution was concentrated in vacuo to a white solid. The solid was partitioned between 0.4M HCl (310 mL) and CH$_2$Cl$_2$. The CH$_2$Cl$_2$ layer was dried (MgSO$_4$) and concentrated in vacuo to a white solid; yield: 10.63 g (96.6%) of 2-dodecyl-2H-tetrazole-5-propanoic acid, mp 63°–65° C.

(c) To a stirred, room temperature solution of the 2-dodecyl-2H-tetrazole acid (1.60 g, 0.00515 mol) in tetrahydrofuran (50 mL) was added in one portion carbonyldiimidazole (0.93 g, 0.0057 mol), and the mixture was stirred for 2 hours. To the mixture was added a solution of 2,4,6-trimethoxyaniline (0.99 g, 0.0054 mol) in THF (50 mL), and the mixture was refluxed for 3 days. The mixture was concentrated in vacuo to a viscous liquid that was chromatographed on silica gel (400 g, 70–230 mesh) using petroleum ether-ETOAc (1:1, 11×500 mL; 2:3, 18×500 mL) as eluent. The product was rechromatographed on silica gel (300 g, 70–230 mesh) using petroleum ether-acetone (3:1, 13×500 mL) as eluent to give an off-white solid; yield: 1.2 g (49%) of N-(2,4,6-trimethoxy-phenyl)-2-dodecyl-2H-tetrazole-5-propanamide, mp 86°–88° C.

EXAMPLE 35

N-(2,6-Bis(1-methylethyl)phenyl)-2-dodecyl-2H-tetrazole-5-propanamide

In a manner similar to Example 34, 2-dodecyl-2H-tetrazole-5-propanoic acid was condensed with 2,6-bis(1-methylethyl)aniline to give the title compound, mp 41°–43° C.

EXAMPLE 36

N-(2,4-Difluorophenyl)-2-dodecyl-2H-tetrazole-5-propanamide

In a manner similar to Example 34, 2-dodecyl-2H-tetrazole-5-propanoic acid was condensed with 2,4-difluoroaniline to give the title compound, mp 86°–87° C.

EXAMPLE 37

1-Dodecyl-N-(2,4,6-trimethoxyphenyl)-1H-tetrazole-5-propanamide

In a manner similar to Example 34, methyl 1-dodecyl-1H-tetrazole-5-propanoate was saponified with KOH to give 1-dodecyl-1H-tetrazole-5-propanoic acid. The acid was condensed with 2,4,6-trimethoxyaniline to give the title compound, mp 57°–61° C.

EXAMPLE 38

(±)-2-Dodecyl-α-(2-pyridyl)-N-(2,4,6-trimethoxyphenyl)-2H-tetrazole-5-acetamide hydrochloride (a) 5-(2-Pyridylmethyl)-1H-tetrazole 2-Pyridylacetonitrile (10.0 g; 0.084 moles) was dissolved in p-dioxane (200 mL) and then treated with tributyltin azide (30.9 g; 0.093 moles) in one portion. The solution was refluxed for 20 hours, cooled to room temperature, and then concentrated in vacuo. The viscous syrup was taken up in ethyl ether and treated with gaseous HCl for over 15 minutes, affording a maroon-colored precipitate that was recrystallized from ethanol. Yield: 9.1 g (55%).

$^1$H NMR (DMSO): δ10.4 (bs, 1H), 8.9 (d, 1H), 8.4 (t, 1H), 7.9 (t, 2H), 4.8 (s, 2H) ppm.

(b) 4-(2-Pyridylmethyl)-2-dodecyl-2H-tetrazole

The tetrazole (a) (3.0 g; 0.015 moles) was taken up in acetonitrile (50 mL) containing two equivalents of triethylamine (3.0 g; 0.030 moles). The suspension was heated to reflux and then treated with 1-bromododecane (3.7 g; 0.015 moles) dropwise for several minutes. The solution was refluxed for 16 hours, cooled to room temperature, and the solvent removed in vacuo. The residue was triturated with ethyl acetate, filtered, and concentration of the filtrate in vacuo leaving a maroon-colored liquid. The 2-isomer was obtained by dissolving the crude product in 50% hexane/50% ethyl acetate and removing the impurities, including the 1-regioisomer, by silica gel chromatography. Yield: 2.0 g (41%).

$^1$H NMR (CDCl$_3$): δ8.5 (d, 1H), 7.7 (t, 1H), 7.3 (d, 1H), 7.2 (m, 1H), 4.5 (t, 2H), 4.4 (s, 2H), 1.9M, 2H), 1.3 (s, 18H), 0.9 (t, 3H) ppm.

(c) (±)-2-Dodecyl-α-(2-pyridyl)-N-(2,4,6-trimethoxyphenyl)-2H-tetrazole-5-acetamide-HCl Compound (b) (2.0 g; 6.0 mmoles) was dissolved in dry tetrahydrofuran (40 mL), cooled to –20° C., and then treated with n-butyllithium (4.0 mL; 6.0 mmoles) dropwise for over 5 minutes. The bright yellow solution was stirred at –20° C. for 10 minutes before adding 2,4,6-trimethoxyphenyl isocyanate (1.3 g; 6.5 mmoles) in one portion. The solution gradually warmed to room temperature for over 3 hours and was then quenched with water. The product was extracted with several portions of chloroform, which were combined, dried over MgSO$_4$, and filtered. The solution was concentrated in vacuo, leaving a viscous yellow syrup that was purified by silica gel chromatography employing a gradient elution composed of hexane/ethyl acetate. The purified product was dissolved in ethyl ether and added dropwise to an ethereal HCl solution. The ether was removed in vacuo leaving a tan-colored solid. Yield: 1.8 g (51).

$^1$H NMR (DMSO): δ9.4 (s, 1H), 8.7 (d, 1H), 8.3 (t, 1H), 7.9 (d, 1H), 7.7 (t, 1H), 6.2 (s, 2H), 5.9 (s, 1H), 4.7 (t, 2H), 3.7 (d, 9H), 1.9 (m, 2H), 1.2 (s, 18H), 0.9 (t, 3H) ppm.

EXAMPLE 39

4-Amino-1,3,5-trimethylpyrazole (a) (1,3,5-Trimethylpyrazole 2,4-Pentanedione (3.8 g; 0.038 moles) was dissolved in acetic acid (30 mL) and then treated with methyl hydrazine sulfate (5.9 g; 0.041 moles) and sodium acetate (3.36 g; 0.041 moles). The suspension was heated on a steam bath for 2 hours, cooled to room temperature, and then added dropwise to saturated aqueous potassium carbonate. The product was extracted with two portions of ethyl acetate and the extracts were combined, dried over magnesium sulfate, and filtered. The filtrate was concentrated in vacuo, leaving an orange liquid. Yield: 3.4 g (81%).

¹H NMR (CDCl₃) δ5.7 (s, 1H), 3.7 (s, 3H), 2.2 (s, 6H) ppm.

(b) 4-Nitro-1,3,5-trimethylpyrazole

The pyrazole from (a) above (3.1 g; 0.028, moles) was dissolved in cold sulfuric acid (15 mL), cooled to 0° C., and then treated with fuming nitric acid (12 mL). The acidic solution was heated on a steam bath for 2 hours, cooled to room temperature, and poured over ice. The solution was made basic (pH=12) and the precipitate was collected by filtration and washed with water. Yield: 2.3 g (53%), white solid.

¹H NMR (CDCl₃) δ3.7 (s, 3H), 2.6 (s, 3H), 2.5 (s, 3H) ppm.

(c) 4-Amino-1,3,5-trimethylpyrazole

The compounds from (b) above (2.3 g; 0.014 moles) was catalytically hydrogenated using Raney nickel (1 g) in methanolic ammonia (100 mL) under a hydrogen atmosphere at 50 psi. The catalyst was filtered and the solution concentrated in vacuo, leaving a residue that was triturated several times with ethyl ether. The decanted solvent was concentrated to dryness, leaving a pale red solid. Yield: 1.3 g (70%).

¹H NMR (CDCl₃) δ3.6 (s, 3H), 2.4 (bs, 2H), 2.1 (s, 6H) ppm.

EXAMPLE 40

Following the general procedure of Example 39 only substituting 2-pyridylhydrazine for methylhydrazine sulfate, the following compound was obtained:

2-[4-amino-3,5-dimethyl-1H-pyrazol-1-yl]pyridine.

¹H NMR (CDCl₃) δ8.4 (d, 1H), 7.7 (m, 2H), 7.2 (m, 1H), 2.4 (s, 3H), 2.2 (s, 3H), 2.0 (bs, 2H) ppm.

EXAMPLE 41

Following the general procedure of Example 13 only substituting the compound of Example 40 for 2,4,6-trimethoxyaniline in Step (e) of Example 13 the following compound was obtained:

(±) 2-dodecyl-α-phenyl-N-[[1-(2-pyridyl)-3,5-dimethyl] pyrazol-4-yl]-2H-tetrazole-5-acetamide.

¹H NMR (CDCl₃) δ8.3 (d, 1H), 7.8 (bs, 1H), 7.7 (d, 2H), 7.5 (d, 2H), 7.3 (m, 3H), 7.1 (t, 1H), 5.4 (s, 1H), 4.6 (5, 2H), 2.4 (s, 3H), 2.1 (s, 3H), 2.0 (m, 2H), 1.3 (s, 18H), 0.9 (t, 3H) ppm.

EXAMPLE 42

The following compound is prepared according to the procedure set forth in Chart VII:

2-dodecyl-N-(2,4,6-trimethoxyphenyl)-2H-tetrazole-5-(3,3-dimethylpropanamide).

EXAMPLE 43

Isolation of the pure enantiomers of (±) 2-dodecyl-α-phenyl-N-(2,4,6-trimethoxyphenyl)-2H-tetrazole-5-acetamide A chromatographic charge is prepared by completely dissolving 1.85 g of racemic 2-dodecyl-α-phenyl-N-(2,4,6-trimethoxyphenyl)-2H-tetrazole-5-acetamide, Example 13, in 45 mL of a solution of 80:20 2-propanol:hexane and warming to 65° C. Two milliliters of this solution is injected onto a 500×20.0 mm Chiralcel OG® preparative column (Diacel Chemical Industries, Tokyo, Japan). This charge is chromatographed over the support with 80:20 hexane:2-propanol at a flow rate of 8.0 mL/min. The column and injector are jacketed in an Advanced Air Oven (Kariba Instruments Cardiff, South Wales, UK) at a constant temperature of 40° C. The eluate is monitored by measuring its ultraviolet absorbance at 290 nm.

The first major ultraviolet absorbing fraction is the (−) enantiomer, (−)-2-dodecyl-α-phenyl-N-(2,4,6-trimethoxyphenyl)-2H-tetrazole-5-acetamide. The capacitance Factor k' for this enantiomer is approximately 5.6 (112 mL solution) and the solution is designated as "Solution A". The value for the capacitance Factor k' is given by the expression k'=(V_e−V_o)/V_o where V_o is the void volume, 90 mL, and V_e is the volume of mobile phase eluted at the maximum ultraviolet absorbance of the first (−) enantiomer, i.e., (−)-2-dodecyl-α-phenyl-N-(2,4,6-trimethoxyphenyl)-2H-tetrazole-5-acetamide. The second major ultraviolet absorbing fraction is the (+) enantiomer, (+)-2-dodecyl-α-phenyl-N-(2,4,6-trimethoxyphenyl)-2H-tetrazole-5-acetamide. This component elutes at a k' of 7.3 (208 mL solution) and is designated as "Solution B". An intermediate fraction eluting at a k' of 6.7 (48 mL solution), which corresponds to the ultraviolet minimum between the two enantiomers contains approximately equal parts of each enantiomer.

This preparative procedure is repeated an additional 19 times. All the "Solution A" fractions are combined and concentrated to a dried film in an open beaker. This film is scraped from the sides of the beaker. The solid is collected and weighed. The resulting 708 mg of (−)-2-dodecyl-α-phenyl-N-(2,4,6-trimethoxyphenyl)-2H-tetrazole-5-acetamide, is found to be 98% enantiomerically pure by high performance liquid chromatography using the conditions listed in Table A. The 20 fractions labeled "Solution B" are combined and dried as described for the "Solution A" fractions. The resulting 727 mg of solid, (+)-2-dodecyl-α-phenyl-N-(2,4,6-trimethoxyphenyl)-2H-tetrazole-5-acetamide, is found to be 96% enantiomerically pure by high performance liquid chromatography using the system described in Table A. The physical properties of (−)-2-dodecyl-α-phenyl-N-(2,4,6-trimethoxyphenyl)-2H-tetrazole-5-acetamide and (+)-2-dodecyl-α-phenyl-N-(2,4,6-trimethoxyphenyl)-2H-tetrazole-5-acetamide appear in Table B.

TABLE A

| | |
|---|---|
| Column: | Chiralcel OG 4.6 × 250 mm 10 μm spherical particles |
| Mobile Phase: | 80:20 hexane:2-propanol |
| Detection: | 214 nm |
| Temperature: | 40° C. |
| Injection Volume: | 20 μL |
| Charge Conc.: | 0.150 mg/mL in the mobile phase |

TABLE B

| | (−)-2-dodecyl-α-phenyl-N-(2,4,6-trimethoxyphenyl)-2H-tetrazole-5-acetamide | (+)-2-dodecyl-α-phenyl-N-(2,4,6-trimethoxyphenyl)-2H-tetrazole-5-acetamide |
|---|---|---|
| Optical Rotation | [å]_D = −58.0 (c. 1.00 MeOH) | [å]_D = +55.1 (c. 1.00 MeOH) |
| Retention Volume | 16.2 mL | 18.8 mL |

EXAMPLE 44

(±)-2-Dodecyl-α-methyl-α-phenyl-N-(2,4,6-trimethoxyphenyl)-2H-tetrazole-5-acetamide (a) (±)-2-Dodecyl-α-methyl-α-phenyl-2H-tetrazole-5-acetic acid To a THF solution (30 mL) of n-BuLi (0.0055 mol, 1.6M in hexanes) at −78° C. under $N_2$ with stirring was added 1.0 g (0.00027 mol) of (±)-2-dodecyl-α-phenyl-2H-tetrazole-5-acetic acid (Compound d, Example 13). The resulting yellow solution was stirred at −78° C. for 30 minutes before iodomethane (0.34 mL, 0.0055 mol) was added. This solution was stirred for 3 hours before quenching with 1N HCl (20 mL). The mixture was then partitioned between ethyl acetate and water. The organic phase was washed with water, brine, dried over $MgSO_4$, filtered, and concentrated in vacuo to yield 1.12 g of pure product.

$^1$H NMR ($CDCl_3$) δ9.9 (br.s, 1H), 7.3 (s, 5H), 4.6 (tr, 2H), 2.2 (s, 3H), 2.1 (tr, 2H), 1.4 (s, 18H), 0.9 (m, 3H) ppm.

(b) (±)-2-Dodecyl-α-methyl-α-phenyl-N-(2,4,6-trimethoxyphenyl)-2H-tetrazole-5-acetamide To a dichloromethane solution (90 mL) of compound in step (a) was added 2,4,6-trimethoxyaniline.HCl (0.64 g, 0.0029 mol) and triethylamine (0.4 mL, 0.0029 mol) at 0° C. under a nitrogen atmosphere with stirring. After 40 minutes, DCC (0.63 g, 0.003 mol) was added in one portion. After 10 minutes a precipitate resulted and the resulting suspension was allowed to warm to room temperature over 72 hours. The suspension was then filtered and the organic layers washed with 1N HCl, water, brine, dried over $MgSO_4$, filtered, and concentrated in vacuo. Flash chromatography (10%–20% EtOAc-Hex or eluant) on $SiO_2$ yielded 0.5 g of pure product.

$^1$H NMR ($CDCl_3$) δ8.1 (S, 1H), 7.2–7.4 (m, 5H), 6.05 (s, 2H), 4.6 (tr, 2H), 3.8 (s, 3H), 3.75 (s, 6H), 2.1 (s, 3H), 2.0 (tr, 2H), 1.4 (s, 18H), 0.9 (m, 3H) ppm.

EXAMPLE 45

(±)-2-Dodecyl-β-phenyl-N-(2,4–6-trimethoxyphenyl)-2H-tetrazole-5-propanamide and (±)-1-dodecyl-d-phenyl-N-(2,4,6-trimethoxyphenyl)-1H-tetrazole-5-acetamide (a) β-cyano-N-(2,4,6-trimethoxyphenyl)benzene propanamide To a dichloromethane (150 mL) solution of 3-cyano-3-phenylpropionic acid (5 g, 0.0286 mol) at 0° C. under a nitrogen atmosphere was added triethylamine (4 mL, 0.0286 mol) and 2,4,6-trimethoxyaniline. HCl (6.3 g, 0.0286 mol). To this solution was added DCC (6.2 g, 0.29 mol). The resulting mixture was allowed to warm to room temperature over 3 hours. This was then filtered and the filtrate partitioned between 1N HCl and dichloromethane. The organic layer was washed with brine, dried over $MgSO_4$, filtered, and concentrated in vacuo. The resulting solid (5.1 g) was recrystallized from dichloromethane/hexanes, mpt 157°–160° C.

(b) (±)-2-Dodecyl-β-phenyl-N-(2,4–6-trimethoxyphenyl)-2H-tetrazole-5-propanamide and (±)-1-dodecyl-β-phenyl-N-(2,4,6-trimethoxyphenyl)-1H-tetrazole-5-acetamide To a suspension of the material from step (a) (5.1 g, 0.016 mol) in dioxane (150 mL) at room temperature was added tri-n-butyltin azide (9.36 g, 0.016 mol) under $N_2$ with stirring. The resulting solution was heated to reflux for 24 hours. The solution was then cooled and concentrated in vacuo. The residue was redissolved in ether and HCl gas was then passed through the'solution for 30 minutes. This was then concentrated in vacuo to give β-(1H-tetrazol-5-yl)-N-(2,4,6-trimethoxyphenyl)benzene propanamide as a white solid (2.1 g) which was used without further purification.

This was dissolved in acetonitrile (50 mL) and triethylamine (0.006 mol) and then heated to reflux. 1-Bromodecane (1.3 mL, 0.0055 mol) was added and the resulting solution heated to reflux for 24 hours. This was then cooled to room temperature and concentrated in vacuo. The residue was treated with ethyl acetate and filtered. The filtrate was washed with brine, dried over $MgSO_4$, filtered, and concentrated in vacuo. Flash chromatography (90% EtOAc-Hex as eluant, $SiO_2$) gave 2.6 g of a 2:1 mixture of regioisomers of the title compounds.

$^1$H NMR ($CDCl_3$) δ7.3 (m, 10H, both regioisomers), 6.1 (s, 4H), both regioisomers), 5.0 (tr, 1H; regioisomer A), 4.8 (tr, 1H, regioisomer B), 4.5 (m, 2H, regioisomer A), 4.2 (m, 2H, regioisomer B), 3.8 (s, 18H, both regioisomers), 3.5 (m, 2H, regioisomer A), 3.1 (m, 2H, regioisomer B), 2.0 (tr, 4H, both regioisomers), 1.3 (s, 36H, both regioisomers), 0.9 (m, 6H, both regioisomers) ppm.

EXAMPLE 46

N-[2,6-Bis(1-methylethyl)phenyl]-2-dodecyl-α,α-diphenyl-2H-tetrazole-5-acetamide (a) 5-(Diphenylmethyl-1H-tetrazole To a dioxan solution (500 mL) of diphenyl-acetonitrile (25.0 g, 0.129 mol) at room temperature under a nitrogen atmosphere was added tri-n-butyltin azide. The resulting solution was heated to reflux for 8 hours. This was then concentrated in vacuo. The residue was redissolved in ether (500 mL) and then treated with HCl gas for 30 minutes. This solution was then concentrated in vacuo and the resulting white solid triturated with hexane. This was then dried in vacuo to yield 15 g (50%) of the title compound, mp 154°–156° C.

(b) 5-(Diphenylmethyl-2-dodecyl-2H-tetrazole

To a solution of (a) (14.8 g, 0.063 mol) in acetonitrile (250 mL) was added triethylamine (9.6 mL, 0.069 mol) at room temperature under $N_2$ with stirring. This solution was then heated to reflux and 1-bromododecane (15.1 mL, 0.063 mol) was added and the resulting solution was heated to reflux for 24 hours. The solution was then concentrated in vacuo and the residue redissolved in ethyl acetate. This was then washed with water, brine, dried over $MgSO_4$, filtered, and concentrated in vacuo to yield a mixture of both regioisomers.

These were then separated using silica gel flash chromatography (hexane as eluant) to yield 7.7 g of the title compound as a clear oil and 5.43 g of 5-(diphenylmethyl-1-dodecyl-1H-tetrazole, mp 81°–84° C.

$^1$H NMR ($CDCl_3$) δ7.2 (s, 10H), 5.8 (s, 1H), 4.5 (tr, 2H), 1.9 (tr, 2H), 1.3 (s, 18H), 0.9 (m, 3H) ppm.

(c) N-[2,6-Bis(1-methylethyl)phenyl]-2-dodecyl-α,α-diphenyl-2H-tetrazole-5-acetamide To a THF solution (30 mL) of 5-(diphenylmethyl)-2-dodecyl-2H-tetrazole (1.0 g, 0.0025 mol) at −30° C. under a nitrogen atmosphere with stirring was added n-BuLi (1.62 mL, 1.6M in hexanes, 0.0026 mol). The resulting deep-red solution was stirred for 30 minutes before a THF solution (10 mL) of 2,6-diisopropyl-phenylisocyanate (0.53 mL, 0.0024 mol) was added dropwise over 10 minutes. The resulting yellow solution was allowed to warm to room temperature over 24 hours. Water (10 mL) was then added and the solution partitioned between ethyl acetate and water. The organic extract was washed with water, brine, dried over $MgSO_4$, filtered, and concentrated in vacuo to yield a yellow oil which was flash chromatographed (5% EtOAc-Hex as eluant, $SiO_2$) to yield 1.16 g of the title product as a clear oil.

$^1$H NMR ($CDCl_3$) δ9.3 (s, 1H), 7.0–7.5 (m, 13H), 4.6 (tr, 2H), 2.9 (heptet, 2H), 2.0 (tr, 2H), 1.4 (s, 18H), 1.0 (s, 6H), 1.1 (s, 6H), 0.9 (m, 3H) ppm.

The following compounds were prepared by methods described previously and referred to as a reference example:

| Example | Reference Example | Product |
|---|---|---|
| 47 | 34 | 2-tetradecyl-N-(2,4,6-trimethoxyphenyl)-2H-tetrazole-5-propanamide, mp 88–91° C. |
| 48 | 1 | 1-dodecyl-N-(2,4,6-trimethoxyphenyl)-1H-tetrazole-5-acetamide, mp 108–109.5° C. |
| 49 | 1 | 2-tetradecyl-N-(2,4,6-trimethoxyphenyl)-2H-tetrazole-5-acetamide, mp 113–115.5° C. |
| 50 | 1 | 1-tetradecyl-N-(2,4,6-trimethoxyphenyl)-1H-tetrazole-5-acetamide, mp 109–110° C. |
| 51 | 38 | (±)-α-[4-dimethylamino)phenyl]-2-dodecyl-N-(2,4,6-trimethoxyphenyl)-2H-tetrazole-5-acetamide, NMR (CDCl₃): δ 7.4 (bs, 3H), 6.7 (bs, 2H), 6.1 (s, 2H), 5.3 (s, 1H), 4.5 (tr, 2H), 3.8 (d, 9H), 2.9 (s, 6H), 2.0 (m, 2H), 1.3 (s, 20H), 0.9 (tr, 3H) ppm. |
| 52 | 38 | (±)-2-Dodecyl-α-(4-fluorophenyl)-N-(2,4,6-trimethoxyphenyl)-2H-tetrazole-5-acetamide NMR (CDCl₃): δ 7.4 (bs, 3H), 6.7 (bs, 2H), 6.1 (s, 2H), 5.3 (s, 1H), 4.5 (t, 2H), 3.8 (d, 9H), 2.9 (s, 6H), 2.0 (m, 2H), 1.3 (s, 20H), 0.9 (t, 3H) ppm. |
| 53 | 38 | (±)-2-Dodecyl-α-2-naphthalenyl-N-(2,4,6-trimethoxyphenyl)-2H-tetrazole-5-acetamide NMR (CDCl₃): δ 8.0 (s, 1H), 7.8 (m, 4H), 7.4 (bs, 3H), 6.1 (s, 2H), 5.6 (s, 1H), 3.8 (d, 9H), 2.0 (m, 2H), 1.2 (s, 20H), 0.9 (t, 3H) ppm. |
| 54 | 38 | (±)-α-([1,1'-biphenyl]-4-yl)-2-dodecyl-N-(2,4,6-trimethoxyphenyl)-2H-tetrazole-5-acetamide NMR (CDCl₃): δ 7.7–7.2 (m, 10H), 6.1 (s, 2H), 5.5 (s, 1H), 4.5 (t, 2H), 3.7 (d, 9H), 2.0 (m, 2H), 1.6 (bs, 2H), 1.2 (s, 18H), 0.9 (t, 3H) ppm. |
| 55 | 38 | (±)-N-[2,6-Bis(1-methylethyl)phenyl]-2-dodecyl-α-2-pyridinyl-2H-tetrazole-5-acetamide NMR (CDCl₃): δ 9.2 (s, 1H), 8.6 (d, 1H), 7.8 (t, 1H), 7.6 (d, 1H), 7.3 (m, 2H), 7.1 (d, 2H), 5.6 (s, 1H), 4.6 (t, 2H), 2.9 (bs, 2H), 2.0 (m, 2H), 1.3 (s, 20H), 1.1 (d, 12H), 0.7 (t, 3H) ppm. |
| 56 | 38 | (±)-2-Dodecyl-α-(4-methoxyphenyl)-N-(2,4,6-trimethoxyphenyl)-2H-tetrazole-5-acetamide |
| 57 | 38 | (±)-2-Dodecyl-α-(4-methylphenyl)-N-(2,4,6-trimethoxyphenyl)-2H-tetrazole-5-acetamide |
| 58 | 13 | (±)-2-Dodecyl-α-(methyl)-N-(2,4,6-trimethoxy-phenyl)-2H-tetrazole-5-acetamide NMR (CDCl₃): δ 7.4 (bs, 1H), 6.1 (s, 2H), 4.5 (t, 2H), 4.2 (q, 1H), 3.8 (d, 9H), 2.0 (m, 2H), 1.7 (d, 3H), 1.3 (s, 18H), 0.8 (tr, 3H) ppm. |
| 59 | 13 | (±)-2-Dodecyl-α-(phenylmethyl)-N-(2,4,6-trimethoxyphenyl)-2H-tetrazole-5-acetamide NMR (CDCl₃): δ 7.4 (bs, 1H), 7.2 (s, 5H), 6.1 (s, 2H), 4.6 (t, 2H), 4.4 (t, 1H), 3.7 (d, 9H), 3.5 (m, 2H), 1.9 (m, 2H), 1.3 (s, 18H), 0.8 (t, 3H) ppm. |

Compounds of Formula (I) containing cycloalkyl groups having from 3 to 8 carbon atoms can also be prepared employing this previously described methodology.

Alternatively, Example 13e can be catalytically hydrogenated to give the corresponding cyclohexyl analog ($R_2$=cyclohexyl, $R_3$=hydrogen).

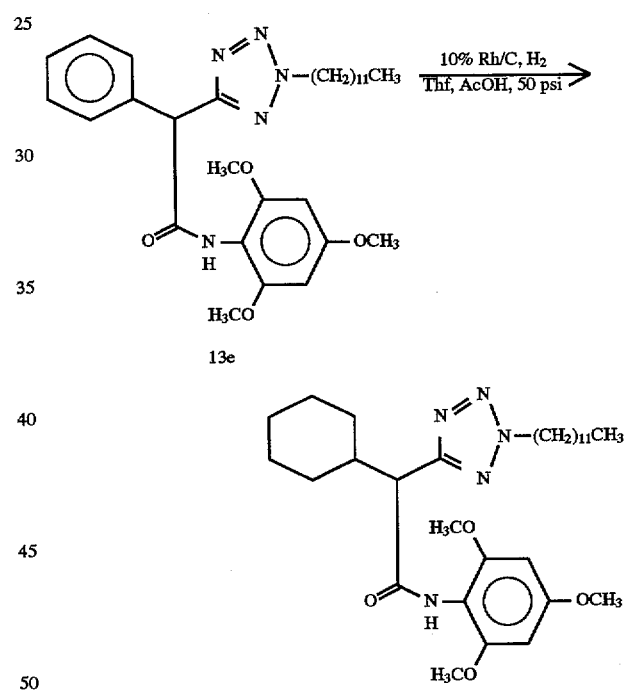

| Example | Product |
|---|---|
| 60 | (±)-2-Dodecyl-α-(cyclohexyl)-N-(2,4,6-trimethoxy-phenyl)-2H-tetrazole-5-acetamide NMR (CDCl₃): δ 7.7 (s, 1H), 6.1 (s, 2H), 4.6 (t, 2H), 3.7 (d, 9H), 3.8 (d, 1H), 2.2 (m, 1H), 2.0 (m, 3H), 1.6 (m, 6H), 1.2 (s, 20H), 1.1 (m, 3H), 0.9 (t, 3H) ppm. |

The following chiral analogs of Formula 13e have also been isolated.

| Example | Product |
|---------|---------|
| 61 | (−)-2-Dodecyl-α-phenyl-N-(2,4,6-trimethoxy-phenyl)-2H-tetrazole-5-acetamide [α]$_D$ = 58° (1% in CH$_3$OH); mp 101–102° C. |
| 62 | (+)-2-Dodecyl-α-phenyl-N-(2,4,6-trimethoxy-phenyl)-2H-tetrazole-5-acetamide [α]$_D$ = 55.1° (1% in CH$_3$OH); mp 100–101° C. |

Vinylic amides (11,12) are prepared from Compound 5 in Chart I as follows:

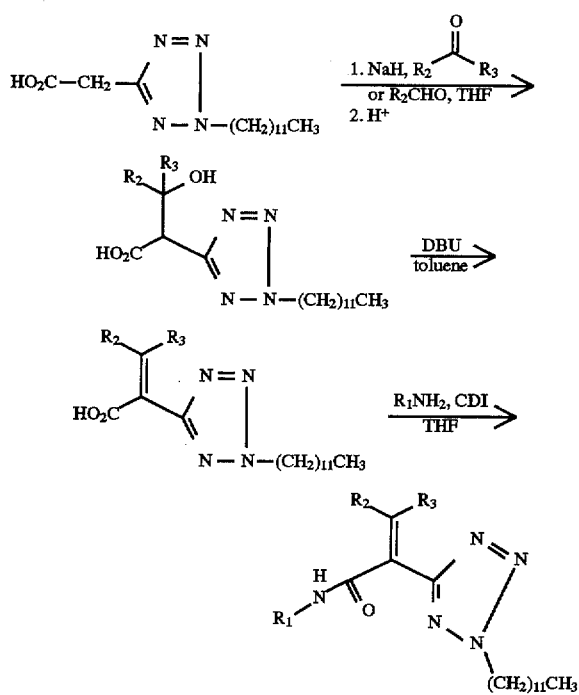

where R$_1$, R$_2$, and R$_3$ have been previously defined in Formula I.
Several examples are:

EXAMPLE 63

2-Dodecyl-α-(phenylmethylene)-N-(2,4,6-trimethoxyphenyl)-2H-tetrazole-5-acetamide

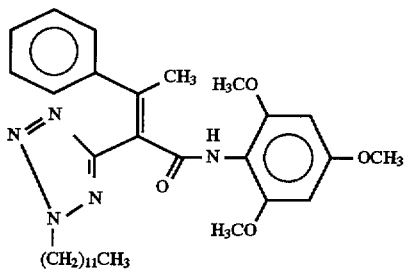

EXAMPLE 64

2-Dodecyl-α-(1-methylethylidene)-N-(2,4,6-trimethoxyphenyl)-2H-tetrazole-5-acetamide

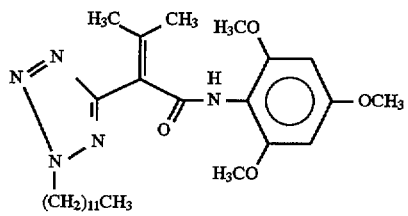

EXAMPLE 65

(±)-N-[2,6-Bis(1-methylethyl)phenyl]-2-dodecyl-α-fluoro-α-phenyl-2H-tetrazole-5-acetamide (a) 2-Dodecyl-α-hydroxy-α-phenyl-2H-tetrazole-5-acetic acid, ethyl ester n-Butyllithium (6.9 mL of a 1.6M hexanes solution, Aldrich) was added dropwise to a −78° C. solution of tetramethylethylenediamine (1.66 mL, 11 mmole, distilled from CaH$_2$) in 10 mL of anhydrous THF (distilled from Na-benzophene) under dry nitrogen. The mixture was stirred for 15 minutes, then 2-dodecyltetrazole (2.38 g, 10 mole) in anhydrous THF (5 mL) was added dropwise. The mixture was stirred for 3 hours at −78° C., then ethyl phenyl glyoxylate (1.75 mL, 11 mole) was added dropwise. The mixture was stirred a further 2 hours, then quenched by dropwise addition of dilute HCl (pH 1). The mixture was allowed to warm to room temperature, then partitioned between ethyl acetate (200 mL) and brine (50 mL). The organic layer was dried, filtered, and concentrated to afford an oil which was flash chromatographed (silica gel, 15:1 heptane-ethyl acetate). This provided 1.55 g (37%) of the title compound as an oil. Anal. Calcd. for C$_{23}$H$_{36}$N$_4$O$_3$: C, 66.32; H, 8.71; N, 13.45. Found; C, 66.47; H, 8.52; N, 12.32.

250 MHz NMR (CDCl$_3$): δ0.88 (t, 3H, J=7 Hz), 1.26 (m, 23H), 2.02 (m, 2H), 4.30 (m, 2H), 4.60 (t, 2H, J=7 Hz), 7.38 (m, 3H), 7.66 (m, 2H), IR (film) 2928, 2856, 1735, 1449, 1256, 697 cm$^{-1}$.

(b) 2-Dodecyl-α-fluoro-α-phenyl-2H-tetrazole-5-acetic acid, ethyl ester

A solution of 2-dodecyl-α-hydroxy-α-phenyl-2H-tetrazole-5-acetic acid, ethyl ester (0.45 g, 1.08 mole) in CH$_2$Cl$_2$ (2 mL) was added dropwise to a −78° C. solution of diethyl amino sulfur trifluoride (DAST, J. Org. Chem. 1975;(40):574:578, 0.15 mL, 1.1 mole) in CH$_2$Cl$_2$ (1 mL) under dry nitrogen. The mixture was stirred for 60 minutes at −78° C. before the cooling bath was removed and the solution allowed to warm to room temperature, where it was stirred an additional 3 hours. The mixture was poured into ice water and extracted with ethyl acetate (2×100 mL). The combined ethyl acetate extracts were washed with brine (50 mL) and dried. Filtration and concentration produced an oil which was flash chromatographed (silica gel, 7:1 hexane-ethyl acetate) to afford 0.3 g (66%) of the title compound as an oil.

Anal. Calcd. for C$_{23}$H$_{35}$FN$_4$O$_2$: C, 66.00; H, 8.43; N, 13.39. Found; C, 66.37; H, 8.60; N, 13.20.

IR (film) 2928, 2856, 1760, 1466, 1266, 695, 406 cm$^{-1}$.

(c) 2-Dodecyl-α-fluoro-α-phenyl-2H-tetrazole-5-acetic acid

NaOH (0.12 g, 3 mole) was added in one portion to a stirred solution of 2-dodecyl-α-fluoro-α-phenyl-2H-tetrazole-5-acetic acid, ethyl ester (0.59 g, 1.4 mole) dissolved in 6 mL of 5:1 CH$_3$OH—H$_2$O at room temperature. After stirring for 3 hours, the mixture was concentrated, diluted with H$_2$O, acidified with 6N HCl (pH 1) and extracted with ethyl acetate (2×150 mL). The combined ethyl acetate extracts were washed with brine (50 mL) and dried. Filtration and concentration afforded 0.5 g (91%) of the title compound as an oil.

(d) (±)-N-[2,6-Bis(1-methylethyl)phenyl]-2-dodecyl-α-fluoro-α-phenyl-2H-tetrazole-5-acetamide Oxalyl chloride (0.08 mL, 0.92 mole) was added to a stirred solution of 2-dodecyl-α-fluoro-α-phenyl-2H-tetrazole-5-acetic acid (0.24 g, 0.61 mole) in 5 mL of CH$_2$Cl$_2$ at room temperature. The mixture was stirred 60 minutes, the one drop of DMF was added (immediate gas evolution). The solution was stirred overnight, concentrated (rotovap), toluene was added, and the solution concentrated again. The residue was dissolved in CH$_2$Cl$_2$ (3 mL) and added to a stirred solution of 2,6-diisopropylaniline (0.12 mL, 0.61 mole) and Et$_3$N (0.14 mL, 1.0 mole) in CH$_2$Cl$_2$ (2 mL) cooled to 0° C. under dry nitrogen. After 20 minutes, the ice bath was removed and the solution allowed to warm to room temperature and stirred for 3 days. The mixture was then diluted with ethyl acetate (150 mL) and washed with dilute HCl (50 mL), bicarbonate (50 mL), brine (50 mL), and dried. Filtration and concentration afforded an oil which was flash chromatographed (silica gel, 10:1 hexanes-ethyl acetate) to produce 150 mg of the title compound as an oil which solidified on standing.

$^1$H NMR (200 MHz) 7.97 (m, 1H), 7.76 (m, 2H), 7.46 (m, 2H), 7.10 (m, 3H) 4.63 (t, 2H, J=7 Hz), 3.03 (m, 2H), 2.05 (m, 2H), 1.25 (m, 18H), 1.10 (m, 12H), 0.88 (m, 3H) ppm.

When in the procedure of Example 65(d) an appropriate amount of 2,4,6-trimethoxyaniline was substituted for 2,6-diisopropylaniline the following Example 66 was obtained.

EXAMPLE 66

(±)-2-Dodecyl-α-fluoro-α-phenyl-N-(2,4,6-trimethoxyphenyl)-2H- tetrazole-5-acetamide $^1$H NMR 7.75 (m, 3H), 7.44 (m, 2H), 6.13 (s, 2H), 4.62 (t, 2H, J=7.5 Hz), 3.80 (s, 3H), 3.76 (s, 6H), 2.04 (m, 2H), 1.25 (m, 18H), 0.88 (m, 3H) ppm, mp 82° C.–83° C.

EXAMPLE 67

Synthesis of 5-decyl-1H-tetrazole

A mixture of n-cyanodecane (20.0 g, 0.12 mol), sodium azide (8.57 g, 0.132 mol), and ammonium chloride (12.8 g, 0.24 mol) in 100 mL DMF was heated to 90° C. for 72 hours. Concentrated in vacuo to one-half original volume and acidified to pH 3.0 with 1N HCl. Concentrated again and partitioned the resulting oily white solid between ethyl acetate and water. The organic layer was dried over magnesium sulfate, filtered, and concentrated in vacuo to give an oily solid. Triturated with ice-cold hexanes to give the title compound (15.53 g, 69%), mp 57–59° C.

EXAMPLE 68

Synthesis of 5-dodecyl-1H-tetrazole

When in the general procedure of Example 67 an appropriate amount of n-cyanododecane was substituted for n-cyanodecane, the title compound was obtained, mp 68°–70° C.

EXAMPLE 69

Synthesis of 5-(diphenylmethyl)-1H-tetrazole

Tributyltin azide (51.55 g, 0.155 mol) and diphenyl acetonitrile (20.0 g, 0.103 mol) were mixed in 400 mL dioxane and heated to reflux for 20 hours. Concentrated in vacuo and redissolved the residue in ether. HCl(g) was bubbled through the solution for 1 hour and the resulting precipitate was collected and washed with hexanes to give the HCl salt of the title compound (15.88 g, 58%), mp 156°–160° C.

EXAMPLE 70

Synthesis of 5-(dodecylthio)-1H-tetrazole

When in the general procedure of Example 69 an appropriate amount of n-dodecylthiocyanate was substituted for diphenyl acetonitrile, the title compound was obtained, mp 85°–87° C.

EXAMPLE 71

Synthesis of ethyl (±)-5-decyl-α-phenyl-2H-tetrazole-2-acetate

The 5-decyl-1H-tetrazole, (4.0 g, 0.019 mol), triethylamine (2.9 mL, 0.021 mol) and ethyl 2-bromophenylacetate (5.09 g, 0.021 mol) were dissolved in 200 mL acetonitrile and heated to reflux for 2 hours. Cooled and concentrated in vacuo to give a yellow oil. Chromatography-to separate the regioisomers gave ethyl (±)-5-decyl-α-phenyl-2H-tetrazole-2-acetate as a clear oil (2.40 g, 34%).

$^1$H NMR (CDCl$_3$): δ7.44–7.28 (m, 5H), 6.43 (s, 1H), 4.37–4.30 (q, 2H), 2.82–2.69 (m, 1H), 2.62–2.49 (m, 1H), 1.73–1.48 (m, 2H), 1.32–1.21 (m, 14H), and 0.90–0.85 (t, 3H) ppm.

EXAMPLE 72

Synthesis of ethyl 5-decyl-2H-tetrazole-2-acetate and ethyl 4-decyl-1H - tetrazole-1-acetate When in the general procedure of Example 71 an appropriate amount of ethyl bromoacetate was substituted for ethyl 2-bromophenylacetate, ethyl 5-decyl-2H-tetrazole-2-acetate was obtained.

$^1$H NMR (CDCl$_3$): δ5.37 (s, 2H), 4.31–4.23 (q, 2H), 2.94–2.88 (t, 2H), 1.82–1.74 (m, 2H), 1.40–1.22 (m, 14H), and 0.90–0.85 (t, 3H) ppm.

Also isolated the 1,5-regioisomer ethyl 5-decyl-1H-tetrazole-1-acetate.

$^1$H NMR (CDCl$_3$): δ5.10 (s, 2H), 4.32–4.23 (q, 2H), 2.82–2.76 (t, 2H), 1.90–1.78 (m, 2H): 1.42–1.19 (m, 14H), and 0.90–0.85 (t, 3H) ppm.

EXAMPLE 73

Synthesis of ethyl (±)-5-(dodecylthio)-α-phenyl-2H-tetrazole-2-acetate

When in the general procedure of Example 71 an appropriate amount of 5-(dodecylthio)-1H-tetrazole was substituted for 5-decyl-1H-tetrazole, the title compound was obtained.

$^1$H NMR (CDCl$_3$): δ7.57–7.42 (m, 5H), 6.57 (s, 1H), 4.34–4.23 (q, 2H), 3.20–3.14 (t, 2H): 1.78–1.66 (m, 2H), 1.43–1.22 (m, 14H), 0.90–0.85 (t, 3H) ppm.

EXAMPLE 74

Synthesis of ethyl(±)-5-(diphenylmethyl)-α-phenyl-2H-tetrazole-2-acetate

When in the general procedure of Example 71 an appropriate amount of 5-(diphenylmethyl)-1H-tetrazole was substituted for 5-decyl-1H-tetrazole, the title compound was obtained.

$^1$H NMR (CDCl$_3$): δ7.57–7.20 (m, 15H), 6.61 (s, 1H), 5.83 (s, 1H), 4.34–4.15 (m, 2H), 1.22–1.16 (t, 3H) ppm.

EXAMPLE 75

Synthesis of ethyl (±)-5-dodecyl-α-phenyl-2H-tetrazole-2-acetate

When in the general procedure of Example 71 an appropriate amount of 5-dodecyl-1H-tetrazole was substituted for 5-decyl-1H-tetrazole, the title compound was obtained.

$^1$H NMR (CDCl$_3$): δ7.58–7.24 (m, 5H), 6.59 (s, 1H), 4.34–4.21 (m, 2H), 2.91–2.85 (t, 2H), 1.82–1.66 (m, 2H), 1.31–1.21 (m, 18H), 0.90–0.85 (t, 3H) ppm.

EXAMPLE 76

Synthesis of ethyl 5-dodecyl-2H-tetrazole-2-acetate

When in the general procedure of Example 71 an appropriate amount of 5-dodecyl-1H-tetrazole was substituted for 5-decyl-1H-tetrazole and an appropriate amount of ethyl bromoacetate was substituted for ethyl 2-bromophenylacetate, the title compound was obtained, mp 38°–40° C.

EXAMPLE 77

Synthesis of ethyl (±)-5-dodecyl-α-pentyl-2H-tetrazole-2-acetate

When in the general procedure of Example 71 an appropriate amount of 5-dodecyl-1H-tetrazole was substituted for 5-decyl-1H-tetrazole and an appropriate amount of ethyl-2-bromoheptanoate was substituted for ethyl 2-bromophenylacetate, the title compound was obtained.

$^1$H NMR (CDCl$_3$): δ5.48–5.30 (t, 1H), 4.29–4.04 (q, 2H), 2.95–2.79 (t, 2H), 2.52–2.20 (m, 2H), 1.90–1.60 (m, 2H), 1.42–0.70 (m, 33H) ppm.

EXAMPLE 78

Synthesis of ethyl (±)-5-dodecyl-α,α-dimethyl-2H-tetrazole-2-acetate

When in the general procedure of Example 71 an appropriate amount of 5-dodecyl-1H-tetrazole was substituted for 5-decyl-1H-tetrazole and an appropriate amount of ethyl-2-bromoisobutyrate was substituted for ethyl 2-bromophenylacetate, the title compound was obtained.

$^1$H NMR (CDCl$_3$): δ4.22–4.13 (q, 2H), 2.92–2.86 (t, 2H), 2.01 (s, 6H), 1.81–1.72 (m, 2H), 1.32–1.15 (m, 18H), 0.90–0.85 (t, 3H) ppm.

EXAMPLE 79

Synthesis of (±)-5-decyl-β-phenyl-2H-tetrazole-2-acetic acid

Solid NaOH (0.33 g, 0.0084 mol) was added to a solution of ethyl (±)-5-decyl-α-phenyl-2H-tetrazole-2-acetate in 50 mL ethanol (90%). The resulting solution was stirred for 1 hour and concentrated in vacuo. The residue was partitioned between diethyl ether and water and the aqueous layer was acidified with 1N HCl. The acidified aqueous layer was extracted with diethyl ether and this ether layer was dried over MgSO$_4$, filtered, and evaporated to give the title compound (1.78 g, 92%), mp 62°–64° C.

EXAMPLE 80

Synthesis of 5-decyl-2H-tetrazole-2-acetic acid

When in the general procedure of Example 79 an appropriate amount of ethyl 5-decyl-2H-tetrazole-2-acetate was substituted for ethyl (±)-5-decyl-α-phenyl-2H-tetrazole-2-acetate, the title compound was obtained, mp 83°–86° C.

EXAMPLE 81

Synthesis of 5-decyl-1H-tetrazole-1-acetic acid

When in the general procedure of Example 79 an appropriate amount of ethyl 5-decyl-1H-tetrazole-1-acetate was substituted for ethyl (±)-5-decyl-α-phenyl-2H-tetrazole-2-acetate, the title compound was obtained, mp 104°–106° C.

EXAMPLE 82

Synthesis of (±)-5-(diphenylmethyl)-α-phenyl-2H-tetrazole-2-acetic acid

When in the general procedure of Example 79 an appropriate amount of ethyl (±)-5-(diphenylmethyl)-α-phenyl-2H-tetrazole-2-acetate was substituted for ethyl (±)-5-decyl-α-phenyl-2H-tetrazole-2-acetate, the title compound was obtained, mp 158°–161° C.

EXAMPLE 83

Synthesis of 5-dodecyl-2H-tetrazole-2-acetic acid

When in the general procedure of Example 79 an appropriate amount of ethyl 5-dodecyl-2H-tetrazole-2-acetate was substituted for ethyl (±)-5-decyl-α-phenyl-2H-tetrazole-2-acetate, the title compound was obtained, mp 89°–91° C.

EXAMPLE 84

Synthesis of (±)-5-dodecyl-α-phenyl-2H-tetrazole-2-acetic acid

When in the general procedure of Example 79 an appropriate amount of ethyl (±)-5-dodecyl-α-phenyl-2H-tetrazole-2-acetate was substituted for ethyl (±)-5-decyl-α-phenyl-2H-tetrazole-2-acetate, the title compound was obtained, mp 76°–78° C.

EXAMPLE 85

Synthesis of (±)-5-dodecyl-α-pentyl-2H-tetrazole-2-acetic acid

When in the general procedure of Example 79 an appropriate amount of ethyl (±)-5-dodecyl-α-pentyl-2H-tetrazole-2-acetate was substituted for ethyl (±)-5-decyl-α-phenyl-2H-tetrazole-2-acetate, the title compound was obtained.

$^1$H NMR (CDCl$_3$): δ9.24 (bs, 1H), 5.54–5.48 (t, 1H), 2.94–2.88 (t, 2H), 2.54–2.30 (m, 2H), 1.81–1.75 (m, 2H), 1.30–1.25 (m, 24H), 0.90–0.86 (t, 6H) ppm.

EXAMPLE 86

Synthesis of 5-dodecyl-α,α-dimethyl-2H-tetrazole-2-acetic acid

When in the general procedure of Example 79 an appropriate amount of ethyl (±)-5-dodecyl-α,α-dimethyl-2H-tetrazole-2-acetate was substituted for ethyl (±)-5-decyl-α-phenyl-2H-tetrazole-2-acetate, the title compound was obtained, mp 68°–71° C.

EXAMPLE 87

Synthesis of (±)-5-(dodecylthio)-α-phenyl-2H-tetrazole-2-acetic acid

When in the general procedure of Example 79 an appropriate amount of ethyl (±)-5-(dodecylthio)-α-phenyl-2H-tetrazole-2-acetate was substituted for ethyl (±)-5-decyl-α-phenyl-2H-tetrazole-2-acetate, the title compound was obtained, mp 64°–67° C.

EXAMPLE 88

Synthesis of N-[2,6-bis(1-methylethyl)phenyl]-5-decyl-2H-tetrazole-2-acetamide

A solution of 2,6-diisopropyl aniline (0.97 g, 0.006 mol) and 5-decyl-2H-tetrazole-2-acetic acid (1.47 g, 0.006 mol) in 100 mL dichloromethane was cooled to 0° C. under an atmosphere of nitrogen. Solid DCC (1.19 g, 0.006 mol) was added in one portion and the resulting suspension was

EXAMPLE 89

Synthesis of N-[2,6-bis(1-methylethyl)phenyl]-5-decyl-1H-tetrazole-1-acetamide

When in the general procedure of Example 88 an appropriate amount of 5-decyl-1H-tetrazole-1-acetic acid was substituted for 5-decyl-2H-tetrazole-2-acetic acid, the title compound was obtained, mp 71°–73° C.

EXAMPLE 90

Synthesis of (±)-N-[2,6-bis(1-methylethyl)phenyl]-5-(diphenylmethyl)-α-phenyl-2H-tetrazole-2-acetamide When in the general procedure of Example 88 an appropriate amount of (±)-5-(diphenyl-methyl)-α-phenyl-2H-tetrazole-2-acetic acid was substituted for 5-decyl-2H-tetrazole-2-acetic acid, the title compound was obtained, mp 180°–183° C.

EXAMPLE 91

Synthesis of N-[2,6-bis(1-methylethyl)phenyl-5-dodecyl-2H-tetrazole-2-acetamide

When in the general procedure of Example 88 an appropriate amount of 5-dodecyl-2H-tetrazole-2-acetic acid was substituted for 5-decyl-2H-tetrazole-2-acetic acid, the title compound was obtained, mp 91°–93° C.

EXAMPLE 92

Synthesis of (±)-N-[2,6-bis(1-methylethyl)phenyl]-5-dodecyl-α-phenyl-2H-tetrazole-2-acetamide When in the general procedure of Example 88 an appropriate amount of (±)-5-dodecyl-α-phenyl-2H-tetrazole-2-acetic acid was substituted for 5-decyl-2H-tetrazole-2-acetic acid, the title compound was obtained, mp 93°–95° C.

EXAMPLE 93

Synthesis of (±)-N-[2,6-bis(1-methylethyl)phenyl]-5-dodecyl-α-pentyl-2H-tetrazole-2-acetamide When in the general procedure of Example 88 an appropriate amount of (±)-5-dodecyl-α-pentyl-2H-tetrazole-2-acetic acid was substituted for 5-decyl-2H-tetrazole-2-acetic acid, the title compound was obtained.

$^1$H NMR (CDCl$_3$): δ7.53 (bs, 1H), 7.33–7.05 (m, 3H), 5.64–5.57 (t, 1H), 2.98–2.92 (t, 2H), 2.47–2.42 (m, 2H), 1.87–1.75 (m, 2H), 1.33–1.09 (m, 24H), 0.90–0.85 (t, 6H) ppm.

EXAMPLE 94

Synthesis of (±)-N-[2,6-bis(1-methylethyl)phenyl]-5-(dodecylthio)-α-phenyl-2H-tetrazole-2-acetamide When in the general procedure of Example 88 an appropriate amount of (±)-5-(dodecylthio)-α-phenyl-2H-tetrazole-2-acetic acid was substituted for 5-decyl-2H-tetrazole-2-acetic acid, the title compound was obtained, mp 102°–105° C.

EXAMPLE 95

Synthesis of (±)-5-decyl-α-phenyl-N-(2,4,6-trimethoxyphenyl)-2H-tetrazole-2-acetamide When in the general procedure of Example 88 an appropriate amount of (±)-5-decyl-α-phenyl-2H-tetrazol-2-acetic acid was substituted for 5-decyl-2H-tetrazole-2-acetic acid and 2,4,6-trimethoxyaniline was substituted for 2,6-diisopropylaniline, the title compound was obtained, mp 145°–147° C.

EXAMPLE 96

Synthesis of (±)-5-(diphenylmethyl)-α-phenyl-N-(2,4,6-trimethoxyphenyl)-2H-tetrazole-2-acetamide When in the general procedure of Example 88 an appropriate amount of (±)-5-(diphenylmethyl)-α-phenyl-2H-tetrazole-2-acetic acid was substituted for 5-decyl-2H-tetrazole-2-acetic acid and 2,4,6-tri-methoxyaniline was substituted for 2,6-diisopropyl-aniline, the title compound was obtained, mp 114°–117° C.

EXAMPLE 97

Synthesis of 5-dodecyl-N-(2,4,6-trimethoxyphenyl)-2H-tetrazole-2-acetamide

When in the general procedure of Example 88 an appropriate amount of 5-dodecyl-2H-tetrazole-2-acetic acid was substituted for 5-decyl-2H-tetrazole-2-acetic acid and 2,4,6-trimethoxyaniline was substituted for 2,6-diisopropylaniline, the title compound was obtained, mp 144°–146° C.

EXAMPLE 98

Synthesis of (±)-5-dodecyl-α-phenyl-N-(2,4,6-trimethoxyphenyl)-2H-tetrazole-2-acetamide When in the general procedure of Example 88 an appropriate amount of (±)-5-dodecyl-α-phenyl-2H-tetrazole-2-acetic acid was substituted for 5-decyl-2H-tetrazole-2-acetic acid and 2,4,6-trimethoxyaniline was substituted for 2,6-diisopropylaniline, the title compound was obtained, mp 141°–145° C.

EXAMPLE 99

Synthesis of (±)-5-dodecyl-α-pentyl-N-(2,4,6-trimethoxyphenyl)-2H-tetrazole-2-acetamide When in the general procedure of Example 88 an appropriate amount of (±)-5-dodecyl-α-pentyl-2H-tetrazole-2-acetic acid was substituted for 5-decyl-2H-tetrazole-2-acetic acid and 2,4,6-trimethoxyaniline was substituted for 2,6-diisopropylaniline, the title compound was obtained, mp 152°–155° C.

EXAMPLE 100

Synthesis of (±)-N-(2,4-difluorophenyl-5-dodecyl-α-phenyl-2H-tetrazole-2-acetamide When in the general procedure of Example 88 an appropriate amount of (±)-5-dodecyl-α-phenyl-2H-tetrazole-2-acetic acid was substituted for 5-decyl-2H-tetrazole-2-acetic acid and 2,4-difluoroaniline was substituted for 2,6-diisopropylaniline, the title compound was obtained, mp 62°–64° C.

EXAMPLE 101

Synthesis of N-(2,4-difluorophenyl)-5-dodecyl-2H tetrazole-2-acetamide

When in the general procedure of Example 88 an appropriate amount of 5-dodecyl-2H-tetrazole-2-acetic acid was substituted for 5-decyl-2H-tetrazole-2-acetic acid and 2,4- difluoroaniline was substituted for 2,6-diisopropylaniline, the title compound was obtained, mp 103°–106° C.

EXAMPLE 102

Synthesis of 5-dodecyl-α,α-dimethyl-N-(2,4,6-trimethoxyphenyl)-2H-tetrazole-2-acetamide When in the general procedure of Example 88 an appropriate amount of 5-dodecyl-α,α-dimethyl-2H-tetrazole-2-acetic acid was substituted for 5-decyl-2H-tetrazole-2-acetic acid and 2,4,6-trimethoxyaniline was substituted for 2,6-diisopropylaniline, the title compound was obtained.

$^1$H NMR (CDCl$_3$): δ6.78 (bs, 1H), 6.09 (s, 2H), 3.78 (s, 3H), 3.73 (s, 6H), 2.97–2.91 (t, 2H), 2.11 (s, 6H), 1.90–1.75 (m, 2H), 1.34–1.24 (m, 18H), 0.90–0.85 (t, 3H) ppm.

EXAMPLE 103

Synthesis of (±)-5-(dodecylthio)-α-phenyl-N-(2,4,6-trimethoxyphenyl)-2H-tetrazole-2-acetamide When in the general procedure of Example 88 an appropriate amount of (±)-5-(dodecylthio)-α-phenyl-2H-tetrazole-2-acetic acid was substituted for 5-decyl-2H-tetrazole-2-acetic acid and 2,4,6-trimethoxyaniline was substituted for 2,6-diisopropylaniline, the title compound was obtained, mp 141°–143° C.

EXAMPLE 104

Synthesis of (±)-5-(dodecylsulfinyl)-α-phenyl-N-(2,4,6)-trimethoxyphenyl)-2H-tetrazole-2-acetamide Solid m-chloroperbenzoic acid (0.5 g, 0.002 mol) was added in one portion to a solution of (±)-5-(dodecylthio)-α-phenyl-N-(2,4,6-trimethoxyphenyl)-2H-tetrazole-2-acetamide (1.15 g, 0.002 mol) in 125 mL dichloromethane at 0° C. under a nitrogen atmosphere. Stirred for 3 hours and then washed with aqueous Na$_2$CO$_3$ solution, dried over MgSO$_4$, filtered, and concentrated to give a cream colored solid. Washed with solid with boiling hexanes to give the title compound (0.87 g, 74%), mp 140°–143° C.

EXAMPLE 105

Synthesis of ethyl (±)-5-dodecyl-α-dodecyl-2H-tetrazole-2-acetate

When in the general procedure of Example 71 an appropriate amount of 5-dodecyl-1H-tetrazole was substituted for 5-decyl-1H-tetrazole and an appropriate amount of ethyl-2-bromomyristate was substituted for ethyl 2-bromophenylacetate, the title compound was obtained. $^1$H NMR (CDCl$_3$): δ5.47–5.41 (m, 1H); 4.25–4.17 (q, 2H); 2.94–2.88 (t, 2H); 2.45–2.26 (m, 2H); 1.82–1.65 (m, 2H); 1.33–1.20 (m, 41H); and 0.90–0.85 (t, 6H) ppm.

EXAMPLE 106

Synthesis of ethyl (±)-5-dodecyl-α-(1-methylethyl)-2H-tetrazole-2-acetate

When in the general procedure of Example 71 an appropriate amount of 5-dodecyl-1H-tetrazole was substituted for 5-decyl-1H-tetrazole and an appropriate amount of ethyl-2-bromo-3-methylbutyrate was substituted for ethyl 2-bromophenylacetate, the title compound was obtained. $^1$H NMR (CDCl$_3$): δ5.26–5.23 (d, 1H); 4.29–4.19 (q, 2H); 2.94–2.77 (m, 3H); 1.82–1.70 (m, 2H); 1.31–1.20 (m, 21H); 1.08–1.05 (d, 3H); 0.97–0.95 (d, 3H) and 0.90–0.85 (t, 3H) ppm.

EXAMPLE 107

Synthesis of (±)-5-dodecyl-α-dodecyl-2H-tetrazole-2-acetic acid

When in the general procedure of Example 79 an appropriate amount of ethyl (±)-5-dodecyl-α-dodecyl-2H-tetrazole-2-acetate was substituted for ethyl (±)-5-decyl-α-phenyl-2H-tetrazole-2-acetate, the title compound was obtained, mp 57°–59° C.

EXAMPLE 108

Synthesis of 5-dodecyl-α-(1-methylethyl)-2H-tetrazole-2-acetic acid

When in the general procedure of Example 79 an appropriate amount of ethyl (±)-5-dodecyl-α-(1-methylethyl)-2H-tetrazole-2-acetate was substituted for ethyl (±)-5-decyl-α-phenyl-2H-tetrazole-2-acetate, the title compound was obtained, mp 39°–42° C.

EXAMPLE 109

Synthesis of (±)-5-dodecyl-α-dodecyl-N-(2,4,6-trimethoxyphenyl)-2H-tetrazole-2-acetamide When in the general procedure of Example 88 an appropriate amount of (±)-5-dodecyl-α-dodecyl-2H-tetrazole-2-acetic acid was substituted for 5-decyl-2H-tetrazole-2-acetic acid and 2,4,6-trimethoxyaniline was substituted for 2,6-diisopropylaniline, the title compound was obtained, mp 138°–140° C.

EXAMPLE 110

Synthesis of 5-dodecyl-α-(1-methylethyl)-N-(2,4,6-trimethoxyphenyl)-2H-tetrazole-2-acetamide When in the general procedure of Example 88 an appropriate amount of 5-dodecyl-α-(1-methylethyl)-2H-tetrazole-2-acetic acid was substituted for 5-decyl-2H-tetrazole-2-acetic acid and 2,4,6-trimethoxyaniline was substituted for 2,6-diisopropylaniline, the title compound was obtained, mp 135°–137° C.

EXAMPLE 111

Synthesis of (±)-N-(2,4,6-trimethoxyphenyl)-5-dodecyl-α-methyl-2H-tetrazole-2-acetamide When in the general procedure of Example 88 an appropriate amount of (±)-5-dodecyl-α-methyl-2H-tetrazole-2-acetic acid was substituted for 5-decyl-2H-tetrazole-2-acetic acid, the title compound was obtained, mp 155°–157° C.

EXAMPLE 112

Synthesis of (±)-N-(2,4,6-trimethoxyphenyl)-5-dodecyl-α-butyl-2H-tetrazole-2-acetamide When in the general procedure of Example 88 an appropriate amount of (±)-5-dodecyl-α-butyl-2H-tetrazole-2-acetic acid was substituted for 5-decyl-2H-tetrazole-2-acetic acid, the title compound was obtained, mp 152°–154° C.

EXAMPLE 113

Synthesis of (±)-N-(2,4,6,-trimethoxyphenyl)-5-dodecyl-α-ethylphenyl-2H-tetrazole-2-acetamide When in the general procedure of Example 88 an appropriate amount of (±)-5-dodecyl-α-ethylphenyl-2H-tetrazole-2-acetic acid was substituted for 5-decyl-2H-tetrazole-2-acetic acid, the title compound was obtained, mp 158°–160° C.

EXAMPLE 114

Synthesis of (±)-N-(2,4,6-trimethoxyphenyl)-5-dodecyl-α-propyl-2H-tetrazole-2-acetamide When in the general procedure of Example 88 an appropriate amount of (±)-5-dodecyl-α-propyl-2H-tetrazole-2-acetic acid was substituted for 5-decyl-2H-tetrazole-2-acetic acid, the title compound was obtained, mp 146°–148° C.

EXAMPLE 115

(±)-2-((S)-citronellyl)-α-phenyl-N-(2,4,6-trimethoxyphenyl)-2H-tetrazole-5-acetamide When in the procedure of Example 13 (b) and appropriate amount of (S)-citronellyl bromide was substituted for 1-bromododecane and the general procedure of Example 13 (b), (d), and (e) was followed, the title compound was obtained. NMR (CDCl$_3$): δ7.6 (m, 3H), 7.3 (m, 4H), 6.1 (s, 2H), 5.4 (s, 1H), 5.0 (t, 1H), 4.6 (t, 2H), 3.7 (d, 9H), 2.0 (m, 6H), 1.6 (d, 4H), 1.4 (m, 2H), 0.9 (d, 3H) ppm.

EXAMPLE 116

(±)-2-geranyl-α-phenyl-N-(2,4,6-trimethoxyphenyl)-2H-tetrazole-5-acetamide

When in the procedure of Example 13 (b) an appropriate amount of geranyl bromide was substituted for 1-bromododecane and the general procedure of Example 13(b), (d), and (e) was followed, the title compound was obtained. NMR (CDCl$_3$): δ7.7 (s, 1H), 7.6 (d, 2H), 7.3 (m, 4H), 6.1 (s, 2H), 5.5 (m, 2H), 5.1 (d, 2H), 5.0 (bs, 1H), 3.7 (d, 9H), 2.1 (s, 4H), 1.8 (d, 3H), 1.6 (d, 6H) ppm.

EXAMPLE 117

(±)-2-undecenyl-α-phenyl-N-(2,4,6-trimethoxyphenyl)-2H-tetrazole-5-acetamide

When in the procedure of Example 13(b) and appropriate amount of the methanesulfonic ester of undecylenyl alcohol was substituted for 1-bromododecane and the general procedure for Example 13(b), (d), and (e) was followed, the title compound was obtained. NMR (CDCl$_3$): δ7.6 (m, 3H), 7.3 (m, 3H), 6.1 (s, 2H), 5.8 (m, 1H), 5.4 (s, 1H), 4.9 (t, 2H), 4.5 (t, 2H), 3.7 (d, 9H), 2.0 (m, 4H), 1.2 (bs, 12H) ppm.

EXAMPLE 118

(±)-2-dodecyl-α-fluoro-N-(2,4,6-trimethoxyphenyl)-2H-tetrazole-5-acetamide

Following the general procedure of Example 27 only substituting one equivalent of N-fluorobenzene-sulfonimide for iodomethane in 27(a), and also following the procedure of Example 13a through 13e, the title compound was obtained. NMR (CDCl$_3$): δ7.6 (bs, 1H), 6.4–6.2 (d, 1H), 6.2 (s, 2H), 4.7 (t, 2H), 3.8 (s, 9H), 2.0 (m, 2H), 1.3 (s, 18H), 0.9 (t, 3H) ppm.

EXAMPLE 119

2-dodecyl-α,α'-difluoro-N-(2,4,6-trimethoxyphenyl)-2H-tetrazole-5-acetamide

Following the general procedure of Example 27, only substituting two equivalents of N-fluorobenzene-sulfonimide for iodomethane in 27(a) and following the general procedure of Example 13(a) through 13(e), the title compound was obtained. NMR (CDCl$_3$): δ7.7 (s, 1H), 6.2 (s, 2H), 4.7 (t, 2H), 3.8 (s, 9H), 2.0 (m, 2H), 1.3 (s, 18H), 0.9 (t, 3H) ppm.

EXAMPLE 120

(±)-(2,4,6-trimethoxyphenyl)-1-dodecyl-α-phenyl-1H-tetrazole-5-acetamide

When in the procedure of Example 25(b) an appropriate amount of 2,4,6-trimethoxyphenyl isocyanate was substituted for 2,4-difluorophenyl isocyanate and the general procedure of 25(b) was followed, the title compound was obtained. NMR (CDCl$_3$): δ8.1 (bs,1H), 7.5 (d, 2H), 7.3 (m, 3H), 6.1 (s, 2H), 5.3 (s, 1H), 4.2 (t, 2H), 3.7 (d, 9H), 1.6 (m, 2H), 1.2 (d, 18H), 0.9 (t, 3H) ppm.

EXAMPLE 121

(±)-N-[2,6,-bis(1-methylethyl)phenyl]-2-dodecyl-α-(4-fluorophenyl)-2H-tetrazole-5-acetamide The title compound was prepared by the procedure in Example 38. NMR (CDCl$_3$): δ8.7 (s, 1H), 7.6 (m, 2H), 7.2 (m, 2H), 7.1 (m, 3H), 5.5 (s, 1H), 4.6 (t, 2H), 2.9 (m, 2H), 2.0 (m, 2H), 1.3 (s, 18H), 1.0 (d, 12H), 0.8 (t, 3H) ppm.

EXAMPLE 122

(±)-4-(1-Dodecenyl)-α-phenyl-N-(2,4,6-trimethoxyphenyl)-1H-pyrazole-1-acetamide (a) Ethyl (±)-α-phenyl-1H-pyrazole-1-acetate A solution of pyrazole (2.80 g, 41 mmol) in 75 mL THF was added dropwise to a suspension of NaH (1.65 g, 41 mmol) in 100 mL THF at −15° C. under an atmosphere of N$_2$. The cloudy solution was warmed to room temperature for 15 minutes, resulting in a clear solution. Cooled to −15° C. and added a solution of ethyl-α-bromo phenyl acetate (7.2 mL, 41 mmol) in 50 mL THF. The resulting yellow suspension was warmed to room temperature for 16 hours and then concentrated in vacuo. The residue was partitioned between water and dichloromethane. The organic layer was dried over MgSO$_4$, filtered, and concentrated to give a light green oil. Chromatography (10% EtOAc/hexanes on silica) gave 5.54 g (58%) of the title compound as a clear oil.

$^1$H NMR (CDCl$_3$): δ7.58 (s, 1H); 7.41 (s, 6H); 6.27 (s, 1H); 6.23 (s, 1H); 4.31–4.24 (m, 2H); 1.30–1.24 (t, 3H) ppm.

(b) Ethyl (±)-4-formyl-α-phenyl-1H-pyrazole-1-acetate

Phosphorous oxychloride (7.0 mL, 75 mmol) was added dropwise to 14 mL DMF at 0° C. under an atmosphere of N$_2$. The resulting solution was stirred for 0.5 hour and then a solution of ethyl (±)-α-phenyl-1H-pyrazole-1-acetate (5.76 g, 25 mmol) in 5 mL DMF was added dropwise. The resulting orange solution was warmed to 70° C. for 16 hours. The reaction mixture was cooled to 0° C. and carefully quenched with saturated Na$_2$CO$_3$ solution. The reaction mixture was partitioned between water and ether and the ether layer was dried over MgSO$_4$, filtered, and concentrated to give an orange oil. Chromatography (15% EtOAc/hexanes on silica) gave 5.73 g (89%) of the title compound as a yellow/green oil which solidified upon standing; mp 68°–70° C.

(c) Ethyl (±)-4-(1-dodecenyl)-α-phenyl-1H-pyrazole-1-acetate

A solution of n-BuLi (127 mL, 254 mmol, 2.0M in hexanes) was added dropwise to a suspension of n-undecyl-triphenylphosphonium bromide (121.6 g, 244 mmol, obtained from triphenylphosphine and undecylbromide) in 500 mL THF at −78° C. under an atmosphere of N$_2$. The resulting orange solution was stirred for 1 hour before a solution of ethyl (±)-4-formyl-α-phenyl-1H-pyrazole-1-acetate in 250 mL THF was added dropwise. Warmed to room temperature and stirred for 16 hours. Quenched by adding 150 mL water and concentrating in vacuo. The residue was partitioned between water and dichloromethane. The organic layer was dried over MgSO$_4$, filtered, and concentrated to give an oily tan solid. Triturated with boiling hexanes and filtered to remove triphenylphosphine oxide. The filtrate was concentrated and chromatographed (10% EtOAc/hexanes on silica) to give the title compound as a yellow oil, a 1:2 E/Z mixture (44.4 g, 50%).

$^1$H NMR (CDCl$_3$): δ7.59 (s, 1H); 7.40–7.26 (m, 6H); 6.17 (s, 1H); 6.16–6.10 (m, 1H); 5.96–5.84 (dt, 1/3 H); 5.53–5.43 (dt, 2/3 H); 4.34–4.22 (m, 2H); 2.26–2.04 (m, 2H); 1.42–1.26 (m, 19H); 0.90–0.85 (t, 3H) ppm.

(d) (±)-4-(1-Dodecenyl)-α-phenyl-1H -pyrazole-1-acetic acid

Solid NaOH (6.72 g, 168 mmol) was added to a solution of ethyl (±)-4-(1-dodecenyl)-α-phenyl-1H-pyrazole-1-acetate (44.41 g, 112 mmol) in 500 mL 95% ethanol. The resulting yellow solution was stirred for 1 hour and then concentrated in vacuo. The residue was partitioned between water and ether, the aqueous layer was acidified with concentrated HCl and extracted with ethyl acetate. The ethyl acetate layer was dried over MgSO$_4$, filtered, and concentrated to give a yellow oil (43.4 g) used without further purification.

(e) (±)-4-(1-Dodecenyl)-α-phenyl-N-(2,4,6-trimethoxyphenyl)-1H-pyrazole-1-acetamide Triethylamine (18 mL, 130 mmol) was added to a suspension of 2,4,6-trimethoxyaniline hydrochloride (28.48 g, 130 mmol) in 500 mL THF and stirred for 1 hour before filtering to remove triethylamine hydrochloride. The filtrate was concentrated and redissolved in 500 mL dichloromethane along with (±)-4-(1-dodecenyl)-α-phenyl-1H-pyrazole-1-acetic acid (43.43 g, 118 mmol) at −15° C. Dicyclohexylcarbodiimide (25.53 g, 124 mmol) was added in one portion and the resulting suspension was warmed to room temperature and stirred for 16 hours. Filtered to remove a white solid and partitioned the filtrate between dichloromethane and 1N HCl. The organic layer was dried over MgSO$_4$, filtered, and concentrated to give an oily tan solid. Recrystallized from hexanes to give the title compound as a tan solid (45.43 g, 72%); mp 82°–85° C.

EXAMPLE 123

(±)-4-Dodecyl-α-phenyl-N-(2,4,6-trimethoxyphenyl)-1H-pyrazole-1-acetamide

In addition to the procedures followed in Example 122, (±)-4-(1-dodecenyl)-α-phenyl-N-(2,4,6-trimethoxyphenyl)-1H-pyrazole-1-acetamide (0.46 g, 0.9 mmol) was dissolved in 75 mL THF and 5% Pd/C (0.1 g) was added. Hydrogen gas (50 psi) was added and the reaction mixture was stirred at room temperature for 2 hours. Filtered to remove the catalyst and concentrated the filtrate to give an oil. Triturated with hexanes to give the title compound as a cream-colored solid (0.45 g, 97%); mp 77°–79° C.

EXAMPLE 124

Synthesis of (±)-N-[2,6-bis(1-methylethyl)phenyl]-4-(1-dodecenyl)-α-phenyl-1H-pyrazole-1-acetamide When in the general procedure of Example 5 an appropriate amount of 2,6-bis(1-methylethyl)aniline was substituted for 2,4,6-trimethoxyaniline, the title compound was obtained, mp 158° C.

EXAMPLE 125

(±)-4-Dodecyl-α-phenyl-N-(2,4,6-trimethoxyphenyl)-1H-imidazole-1-acetamide (a) 4-(1-Dodecenyl)-1-(triphenylmethyl) imidazole A solution of n-BuLi (4.1 mL, 6.5 mmol, 1.6M in hexanes) was added dropwise to a suspension of n-undecyl-triphenylphosphonium bromide (3.09 g, 6.2 mmol, obtained from triphenylphosphine and undecylbromide) in 100 mL THF at −78° C. under an atmosphere of N$_2$. The resulting orange solution was stirred for 45 minutes before a solution of 1-(triphenylmethyl)-4-imidazolecarboxaldehyde (2.0 g, 5.9 mmol, Ref: Kelly J. L., Miller C. A., and McLean E. W., *J. Med. Chem.* 1977; 20:721) in 75 mL THF was added dropwise. Warmed to room temperature and stirred for 16 hours. Quenched by adding 50 mL saturated NH$_4$Cl solution and concentrating in vacuo. The residue was partitioned between water and dichloromethane. The organic layer was dried over MgSO$_4$, filtered, and concentrated to give a yellow oil. Chromatography (10% EtOAc/hexanes on silica) gave the title compound (1.8 g, 64%) as a clear oil.

$^1$H NMR (CDCl$_3$): δ7.46 (s, 1H); 7.35–7.12 (m, 15H); 6.75 (s, 1H); 6.29–6.25 (d, 1H); 5.62–5.52 (dt, 1H); 2.33–2.24 (m, 2H); 1.38–1.23 (m, 16H); 0.90–0.85 (t, 3H) ppm.

(b) 4-Dodecylimidazole

Twenty percent Pd/C (1 g) was added to a solution of 4-(1-dodecynyl)-1-(triphenylmethyl) imidazole (2.39 g, 5 mmol) in glacial acetic acid (100 mL), along with 50 psi of hydrogen gas. Stirred for 16 hours and concentrated in vacuo. The residue was made basic with saturated Na$_2$CO$_3$, neutralized with 1N HCl, and extracted with ether. The ether layer was dried over MgSO$_4$, filtered, and concentrated to give an oily white solid. Recrystallized from hexanes to give the title compound as a white solid (1.06 g, 90%); mp 69°–71° C.

(c) Ethyl (±)-4-dodecyl-α-phenyl-1H-imidazole-1-acetate

A solution of ethyl-α-bromo phenyl acetate (5.14 g, 21 mmol) in 50 mL DMF was added dropwise to a suspension of 4-dodecylimidazole (5.0 g, 21 mmol) and triethylamine (3.0 mL, 21 mmol) in 100 mL DMF. Stirred for 16 hours at room temperature and concentrated in vacuo. The residue was partitioned between ethyl acetate and water and the organic layer was dried over MgSO$_4$, filtered, and concentrated to give an orange oil. Chromatography (10% EtOAc/hexanes on silica) gave 4.57 g (54%) of the title compound as an orange oil.

$^1$H NMR (CDCl$_3$): δ7.52 (s, 1H); 7.41–7.25 (m, 5H); 6.73 (s, 1H); 5.83 (s, 1H); 4.32–4.24 (q, 2H); 2.57–2.50 (t, 2H); 1.64–1.56 (m, 2H); 1.31–1.25 (m, 21H); 0.90–0.85 (t, 3H) ppm.

(d) (±)-4-Dodecyl-α-phenyl-1H-imidazole-1-acetic acid

Solid NaOH (0.9 g, 22.6 mmol) was added to a solution of ethyl (±)-4-dodecyl-e-phenyl-1H-imidazole-1-acetate (4.5 g, 11.3 mmol) in 150 mL 95% ethanol. The resulting solution was stirred for 2 hours and then concentrated in vacuo. The residue was partitioned between water and ether, the aqueous layer was acidified with concentrated HCl, and extracted with dichloromethane. The dichloromethane solution was dried over MgSO$_4$, filtered, and concentrated to give a white solid (2.53 g, 55%); mp 110°–118° C.

(e) (±)-4-Dodecyl-α-phenyl-N-(2,4,6-trimethoxyphenyl)-1-imidazole-1-acetamide

Excess triethylamine (2 mL) was added to a suspension of 2,4,6-trimethoxyaniline hydrochloride (1.6 g, 7.3 mmol) in 500 mL THF and stirred for 1 hour before filtering to remove triethylamine hydrochloride. The filtrate was concentrated and redissolved in 500 mL dichloromethane along with (±)-4-dodecyl-α-phenyl-1H-imidazole-1-acetic acid (2.45 g, 6.6 mmol) at 0° C. Dicyclohexylcarbodiimide (1.43 g, 6.9 mmol) was added in one portion and the resulting suspension was warmed to room temperature and stirred for 16 hours. Filtered to remove a white solid and partitioned the filtrate between dichloromethane and 1N HCl. The organic layer was washed with 1N NaOH, dried over MgSO$_4$,

EXAMPLE 126

(±)-4-Dodecyl-α-phenyl-N-(2,4,6-trimethoxyphenyl)-2H-1,2,3-triazole-2-acetamide (a) 4-Dodecyl-1,2,3-triazole A mixture of 1-tetradecyne (6.6 g, 34 mmol) and trimethylsilyl azide (4.1 g, 35 mmol) was autoclaved at 135° C. for 14 hours and then at 150° C. for 14 hours. The resulting mixture was rinsed with ether and the ether solution was washed with water, dried over $MgSO_4$, filtered, and concentrated to give a brown oil. Triturated with cold hexanes to give the title compound as a tan solid (4.02 g, 50%); mp 64°–67° C.

(b) Ethyl (±)-4-dodecyl-α-phenyl-2H-1,2,3-triazole-2-acetate

A solution of 4-dodecyl-1,2,3-triazole (0.99 g, 4.2 mmol) in 50 mL THF was added dropwise to a suspension of sodium hydride (0.18 g, 4.6 mmol, 60% dispersion in mineral oil) in 50 mL THF at 0° C. The resulting foamy tan suspension was warmed to room temperature and stirred for 1 hour and then cooled to 0° C. A solution of ethyl-α-bromo phenyl acetate (1.01 g, 4.2 mmol) in 50 mL THF was added dropwise and the reaction mixture was stirred at room temperature for 16 hours. Concentrated in vacuo and partitioned between water and ethyl acetate. The organic layer was dried over $MgSO_4$, filtered, and concentrated to give a clear oil. Chromatography (10% EtOAc/hexanes on silica) gave the title compound as a white solid (0.61 g, 36%); mp 68°–70° C.

(c) (±)-4-Dodecyl-α-phenyl-2H-1,2,3-triazole-2-acetic acid

Solid NaOH (0.44 g, 11 mmol) was added to a solution of ethyl (±)-4-dodecyl-α-phenyl-2H-1,2,3-triazole-2-acetate (2.92 g, 7.3 mmol) in 100 mL 95% ethanol. The resulting yellow solution was stirred for 1 hour and then concentrated in vacuo. The residue was partitioned between water and ether, the aqueous layer was acidified with concentrated HCl and extracted with ethyl acetate. The ethyl acetate solution was dried over $MgSO_4$, filtered, and concentrated to give an off-white solid (2.75 g, quant.); mp 94°–98° C.

(d) (±)-4-Dodecyl-α-phenyl-N-(2,4,6-trimethoxyphenyl)-2H-1,2,3-triazole-2-acetamide Triethylamine (1.2 mL, 8.4 mmol) was added to a suspension of 2,4,6-trimethoxyaniline hydrochloride (1.68 g, 7.7 mmol) in 100 mL THF and stirred for 1 hour before filtering to remove triethylamine hydrochloride. The filtrate was concentrated and redissolved in 100 mL dichloromethane along with (±)-4-dodecyl-α-phenyl-2H-1,2,3-triazole-2-acetic acid (2.59 g, 7.0 mmol) at 0° C. Dicyclohexylcarbodiimide (1.51 g, 7.3 mmol) was added in one portion and the resulting suspension was warmed to room temperature and stirred for 16 hours. Filtered to remove a white solid and partitioned the filtrate between chloroform and 1N HCl. The organic layer was dried over $MgSO_4$, filtered, and concentrated to give a pale lavender solid. Recrystallization from ethyl acetate/hexanes (4:1) gave the title compound as a white solid (2.80 g, 75%); mp 123°–125° C.

EXAMPLE 127

3-Dodecyl-N-(2,4,6-trimethoxyphenyl)-5-isoxazole acetamide (a) Hexadecanoic acid, 2,4-dioxo-, ethylester, monosodium salt To a cool (+5° C.), stirred volume of absolute ethanol (260 mL) under nitrogen was added portionwise sodium metal (4.3 g, 0.19 mol) over 45 minutes, and the mixture was allowed to warm to room temp and stirred until the sodium had dissolved (1.5 hours). To the mixture was added a suspension of 2-tetradecanone (39.1 g, 0.184 mol) in diethyloxalate (25.0 mL, 0.184 mol). The mixture was heated to 60° C., stirred for 5 hours, and allowed to cool. A solid precipitated. The suspension was chilled (+3° C.), filtered off, and washed with cold ethanol. The solids were recrystallized from ethanol to give a pale yellow solid, yield 25.94 g (39%).

$^1$H NMR (DMSO) δ5.4 (s. br., 1H), 4.0 (q, 2H), 2.2 (m, 2H), 1.4 (m, 2H), 1.2 (m, 21H), 0.85 (t, 3H) ppm.

(b) 3-Dodecyl-5-isoxazole carboxylic acid

To a stirred, warm (55° C.) solution of hexadecanoic acid, 2,4-dioxo, ethyl ester, monosodium salt (15.50 g, 0.046 mol) in glacial acetic acid (125 mL) was added dropwise a solution of hydroxylamine hydrochloride (6.45 g, 0.093 mol) in water (32 mL) over 10 minutes, and the mixture was stirred at 60° C. for 25 hours. The mixture was allowed to cool and partitioned between $H_2O$ (250 mL) and chloroform (400 mL). The organic layer was washed (saturated NaCl), dried ($MgSO_4$), and rotoevaporated. The residue was dissolved (toluene), rotoevaporated, and the solid recrystallized from toluene to give a white solid, yield 5.62 g (43%), mp 119°–122° C.

The filtrate from the $CHCl_3$ crystallization was chromatographed on silica gel (400 g, 70–230 mesh) using petroleum ether-ethyl acetate (29:1, 7×800 mL) eluent. Fractions containing product were rotoevaporated, dissolved ($CH_2Cl_2$), and rotoevaporated to an oil, which was dried in vacuo. The oil crystallized upon standing. The solid was recrystallized from methanol to give 5-dodecyl-3-isoxazole carboxylic acid, ethyl ester; yield 4.36 g, (30%), mp 34°–36° C.

(c) 3-Dodecyl-5-isoxazole methanol

To a stirred, chilled (+3° C.) solution of 3-dodecyl-5-isoxazole carboxylic acid (24.27 g, 0.08625 mol) and triethylamine (12.0 mL, 0.0861 mol) in dry tetrahydrofuran (600 mL) under nitrogen was added in one portion a chilled (+3° C.) solution of ethyl chloroformate (8.25 mL, 0.0863 mol) in dry tetrahydrofuran (30 mL). A white precipitate formed immediately. The suspension was stirred for 1.25 hours before sodium borohydride (6.54 g, 0.173 mol) was added in portions over 10 minutes. The mixture was stirred for 1.5 hours while warming to room temperature. The mixture was rechilled and carefully quenched with water (350 mL). The organic layer was diluted with dichloromethane. The aqueous layer was washed with THF-$CH_2Cl_2$. The organic solutions were combined, dried ($Na_2SO_4$), and rotoevaporated. The residue was chromatographed on silica gel (1.5 kg, 70–230 mesh) using petroleum ether-acetone (9:2, 20×1 L) eluent. Fractions 10 to 14 were rotoevaporated from dichloromethane and dried in vacuo to give a white solid; yield 11.1 g (48%); mp 57°–59° C.

(d) 5-(Bromomethyl)-3-dodecylisoxazole

To a stirred, chilled (+3° C.) solution of 3-dodecyl-5-isoxazole methanol (1.0 g, 0.0037 mol) in dichloromethane (20 mL) was added in one portion phosphorous tribromide (0.13 mL, 0.0014 mol), and the solution was stirred at +3° C. for 1.5 hours, then at room temperature for 3 days. The mixture was washed carefully with saturated sodium bisulfite, saturated sodium bicarbonate, and saturated sodium chloride. The organic layer was dried ($MgSO_4$) and rotoevaporated to a yellow oil which solidified upon standing; yield 1.12 g (93%); mp 31.5°–35° C.

(e) 3-Dodecyl-5-methylisoxazole

A suspension of 5-(bromomethyl)-3-dodecylisoxazole (9.99 g, 0.0302 mol) in dimethylsulfoxide (100 mL) was warmed to give a cloudy solution and allowed to cool. When the temperature reached +35° C., sodium borohydride (1.2 g, 0.032 mol) was added in one portion, and the mixture was stirred for 3 days under nitrogen at room temperature. The mixture was poured into 0.1M HCl (900 mL) and extracted with ether. The organic layer was washed (saturated NaCl), dried (MgSO$_4$), and rotoevaporated. The residue was chromatographed on silica gel (160 g, 70–230 mesh) using petroleum ether-acetone (29:1, 10×200 mL) as eluent. Fraction 6 was rotoevaporated and dried in vacuo to give a white solid; yield 3.96 g (52%); mp 35°–38° C.

(f) 3-Dodecyl-5-isoxazole acetic acid

To a cold (−75° C.), stirred suspension of 3-dodecyl-5-methylisoxazole (3.40 g, 0.0135 mol) in dry tetrahydrofuran (900 mL) was added in one portion a 1.6M solution (8.5 mL, 0.014 mol) of n-butyl lithium in hexanes, and the mixture was stirred for 1.5 hours. The mixture was poured onto freshly crushed dry ice and allowed to warm overnight. The mixture was rotoevaporated, and the residue was partitioned between petroleum ether and 0.5M NaOH. The aqueous layer was washed (petroleum ether), acidified with concentrated hydrochloric acid to pH ~1–2, and extracted (CHCl$_3$). The extract was dried (MgSO$_4$) and rotoevaporated to a waxy solid. The solid was recrystallized from toluene to give a white solid; yield 0.65 g (16%); mp 79°–80° C.

(g) 3-Dodecyl-N-(2,4,6-trimethoxyphenyl)-5-isoxazole acetamide

To a stirred, room temperature solution of 3-dodecyl-5-isoxazole acetic acid (0.64 g, 0.0022 mol) in dry tetrahydrofuran (20 mL) under nitrogen was added in one portion, 1,1-carbonyldiimidazole (0.38 g, 0.0024 mol), and the mixture was stirred for 2 hours. To this solution was added 2,4,6-trimethoxyaniline hydrochloride (0.48 g, 0.0022 mol) and triethylamine (0.33 mL, 0.0024 mol) in THF (30 mL). The mixture was stirred for 2 days and allowed to cool. The solution was rotoevaporated and the residue dissolved in dichloromethane. The solid was filtered through silica gel (77 g, 70–230 mesh) using petroleum ether-acetone (4:1, 35×75 mL) and the filtrate rotoevaporated to an oil. The oil was dried in vacuo. The oil crystallized to give a pale yellow waxy solid; yield 0.96 g (96%); mp 107°–109° C.

EXAMPLE 128

(±)-3-Dodecyl-α-phenyl-N-(2,4,6-trimethoxyphenyl)-5-isoxazole acetamide (a) 2-[(Trimethylsilyl)oxy]-1-tetradecene To a stirred, room temperature solution of diisopropylamine (49 mL, 0.35 mol) in dry THF (500 mL) was added a 2.06M solution (170 mL, 0.35 mol) of n-butyl lithium in hexanes in one portion. The solution was cooled to −78° C. To the stirred solution was added neat trimethylsilylchloride (213 mL, 1.68 mol) over 6 minutes. Stirred for 6 minutes. To this solution was added a solution of 2-tetradecanone (71.40 g, 0.3362 mol) in dry THF (710 mL) over 33 minutes. Stirred 5 minutes. To the mixture was added triethylamine (375 mL, 2.7 mol) over 6 minutes followed by a saturated sodium bicarbonate solution (780 mL). The mixture was allowed to warm. When the temperature reached 0° C., petroleum ether (1.7 L) was added, and the organic layer was washed with chilled H$_2$O (2×1.4 L), chilled 0.1M citric acid (3×2 L) and saturated NaCl. The organic layer was dried (Na$_2$SO$_4$) and rotoevaporated and dried in vacuo to give a yellow oil; yield 97.6 g (102%).

$^1$H NMR (CDCl$_3$): δ4.0 (s, 2H); 2.0 (t, 2H); 1.3 (m, 20H); 0.88 (t, 3H); 0.20 (s, 9H).

(b) (±)-2-Hydroxy-1-phenyl-4-hexadecanone

To a stirred, cold (−78° C.) volume of dichloromethane (1.8 L) was added in one portion under nitrogen phenylacetaldehyde (92.6 g, 0.771 mol) followed by a dropwise addition of neat titanium tetrachloride (84 mL, 0.77 mol) over 3 minutes. Stirred 2 minutes. To the resulting orange suspension was added over 35 minutes a solution of 2-[(trimethylsilyl)oxy]-1-tetradecene (187.0 g, 0.6572 mol) in CH$_2$Cl$_2$ (1.5 L). Stirred 1.2 hours. The mixture was quenched with water (800 mL) and allowed to warm. When the temperature reached 0° C., saturated sodium bicarbonate (1.5 L) was carefully added followed by enough 50% wt/wt sodium hydroxide to raise the pH to 10. The organic layer was washed (saturated NaCl), dried (Na$_2$SO$_4$), and rotoevaporated to an oil. The oil was crystallized from acetonitrile twice and once from petroleum ether to give an off-white solid; yield 77.8 g (35.6%); mp 40°–43° C.

(c) 1-Phenyl-2,4-hexadecanedione

To a cold (−60° C.), stirred solution of oxalyl chloride (32 mL, 0.37 mol) in dichloromethane (980 mL) was added over 10 minutes a solution of dimethylsulfoxide (52 mL, 0.73 mol) in CH$_2$Cl$_2$ (450 mL). Stirred 2 minutes. To the mixture was added a solution of (±)-2-hydroxy-1-phenyl-4-hexadecanone (105.6 g, 0.3176 mol) in CH$_2$Cl$_2$ (900 mL) over 17 minutes. Stirred 20 minutes. To the mixture was added triethylamine (230 mL, 1.65 mol) over 5 minutes. Stirred 5 minutes. The mixture was allowed to warm to −20° C. and water (1 L) was added. Stirred 30 minutes. The organic layer was washed (1M HCl and saturated NaCl), dried (Na$_2$SO$_4$), and rotoevaporated to an oil. The oil was chromatographed on silica gel using petroleum ether-acetone (45:1) to give a pale yellow oil; yield 67.6 g (64.5%).

$^1$H NMR (CDCl$_3$): δ15.4 (s, 1H); 7.3 (m, 5H); 5.4 (s, 1H); 3.6 (s, 2H); 2.2 (t, 2H); 1.6 (m, 2H); 1.3 (s, 18H); 0.89 (t, 3H).

(d) 3-Dodecyl-5-(phenylmethyl)isoxazole

A mixture of 1-phenyl-2,4-hexanedione (66.5 g, 0.201 mol), hydroxylamine hydrochloride (27.9 g, 0.402 mol), and 1M sodium hydroxide (201 mL, 0.201 mol) in glacial acetic acid (1.5 L) was stirred at 65° C. under nitrogen for 23 hours. The solution was allowed to cool, and the resulting suspension was filtered off and washed with CH$_3$CO$_2$H—H$_2$O (9:1). The filtercake was washed separately with H$_2$O and dried under house vacuum/air stream to give a white crystalline solid containing the title compound and 5-dodecyl-3-(phenylmethyl)isoxazole; yield 41.8 g (64%); mp 41°–43° C. Additional product was obtained by reheating the CH$_3$CO$_2$H filtrate and washings to 60° C.; adding H$_2$O (150 mL) dropwise until cloudy, and following the previous procedure; yield 15.2 g (23%).

(e) (±)-3-Dodecyl-α-phenyl-5-isoxazole acetic acid

To a cold (−78° C.), stirred suspension of 3-dodecyl-5-(phenylmethyl)isoxazole and 5-dodecyl-3-(phenylmethyl)isoxazole (1.64 g, 0.00500 mol) in dry tetrahydrofuran (150 mL) was added dropwise over 3 minutes a 2.06M solution (5.0 mL, 0.010 mol) of n-butyl lithium in hexanes, and the mixture was stirred for 80 minutes under nitrogen. The resulting orange solution was poured into freshly crushed dry ice (−300 g), the mixture was covered with parafilm with a small hole to allow CO$_2$ (g) to escape, and allowed to warm to room temperature over 3 hours. The residue was partitioned between ether and 0.1M HCl. The organic layer was washed (saturated NaCl), dried (MgSO$_4$), and rotoevaporated to a yellow oil. The oil was dissolved in petroleum ether (50 mL). A solid crystallized. It was filtered off and dried in vacuo to give a white solid containing the title compound and 5-dodecyl-α-phenyl-3-isoxazole acetic acid; yield 1.70 g (91%); mp 88°–97° C.

(f) (±)-3-Dodecyl-α-phenyl-N-(2,4,6-trimethoxyphenyl)-5-isoxazole acetamide

To a room temperature, stirred solution of 3-dodecyl-α-phenyl-5-isoxazole acetic acid and 5-dodecyl-α-phenyl-3-isoxazole acetic acid (48.42 g, 0.1303 mol) in dry tetrahydrofuran (1.4 L) was added in one portion 1,1'-carbonyldiimidazole (22.5 g, 0.139 mol), and the solution was stirred for 1.9 hours under nitrogen. To the mixture was added 2,4,6-trimethoxyaniline hydrochloride (28.5 g, 0.130 mol) and triethylamine (19 mL, 0.14 mol), and the mixture was stirred for 1.8 days under nitrogen. The mixture was rotoevaporated and partitioned between ethyl acetate and 1M HCl. The organic layer was washed (1M HCl; saturated NaCl), dried (MgSO₄), and rotoevaporated to a tar. The tar was dissolved (THF) and repeatedly chromatographed on silica gel (230–400 mesh) using Heptane-ether-triethylamine-methanol (20:40:6:1) as eluent. Fractions containing pure compound were combined, rotoevaporated, dissolved in toluene, and reevaporated. The residue was crystallized from diisopropyl ether to give pure title compound; yield 17.6 g (25%); mp 107°–108° C.

Also obtained was pure (±)-5-dodecyl-α-phenyl-N-(2,4,6-trimethoxyphenyl)-3-isoxazole acetamide; yield 13.8 g (20%); mp 90°–91° C.

In a preferred embodiment Example 128 is obtained as follows:

(±)-3-Dodecyl-α-phenyl-N-(2,4,6-trimethoxyphenyl)-5-isoxazole acetamide (a) 2,4,6-Trimethoxyphenyl isocyanate A suspension of 2,4,6-trimethoxyaniline (71 g, 0.324 mol) in a 12.5% wt/wt solution (540 mL) of phosgene in toluene was heated on a steam bath with periodic swirling for 3 hours. Additional phosgene in toluene solution (2×270 mL) was added after 1 and hours. The suspension was allowed to cool, placed under house vacuum, and stirred for 2.5 days. The mixture was rotoevaporated to a dark purple solid. The residue was dissolved in ether (450 mL), filtered, rotoevaporated, and dried in vacuo to give a purple amorphous solid; yield 66.9 g (98.7%), mp 67°–70° C.

(b) 1-Nitrotridecane

To a stirred, room temperature suspension of sodium nitrite (227 g, 3.29 mol) in dimethylformamide (3.8 L) was added 1-bromotridecane (514.51 g, 1.95435 mol), and the mixture was stirred for 6 hours. The mixture was poured into cold water (8 L) and extracted with petroleum ether (2×2 L). The organic layer was washed with water (2 n), saturated sodium chloride, dried (MgSO₄), and rotoevaporated to a yellow oil. The oil was distilled in vacuo to give another oil; yield 171.9 g, bp 101°–120° C. (0.2 mm Hg). The oil was chromatographed on silica gel (3.0 kg, 230–400 mesh) using ether/ethyl acetate (100:1, 4×2 L; 80:1, 4×2 L; 50:1, 7×2 L) to give a clear colorless oil; yield 109.8 g (24.5%).

¹H NMR (CDCl₃): 4.4 (t, 2H), 2.0 (m, 2H), 1.3–1.7 (m, 20H), 0.88 (t, 3H) ppm.

(c) 3-Dodecyl-5-(phenylmethyl)isoxazole

To a room temperature, stirred solution of 3-phenyl-1-propyne (54.86 g, 0.4723 mol) and phenyl isocyanate (104 mL, 0.957 mol) in benzene (800 mL) under nitrogen was added dropwise over 30 minutes a solution of 1-nitrotridecane (109.14 g, 0.47583 mol) and triethylamine (6.7 mL, 0.048 mol) in benzene (400 mL), and the mixture was stirred for 1 hour. The mixture was refluxed for 6 hours, allowed to cool, and chilled. The solids were filtered off and the filtrate rotoevaporated to an oil. The oil was chromatographed on silica gel (1.4 kg, 230–400 mesh) using petroleum ether-ether (25:1, 15×1 L), and product fractions rotoevaporated to give an off-white solid; yield 96.1 g (62%), mp 45°–47° C.

(d) (±)-3-Dodecyl-α-phenyl-N-(2,4,6-trimethoxyphenyl)-5-isoxazole acetamide

A stirred room temperature solution of 3-dodecyl-5-(phenylmethyl)isoxazole (38.3 g, 0.117 mol) in tetrahydrofuran (600 mL) was cooled to –78° C. under nitrogen. To the resulting precipitate was added dropwise a 2.01M solution (58 mL, 0.12 mol) in n-butyl lithium in hexanes over 10 minutes. The mixture was stirred for 1.25 hours before a solution of 2,4,6-trimethoxyphenyl isocyanate (24.43 g, 0.1168 mol) in tetrahydrofuran (350 mL) was added dropwise over 30 minutes. The mixture was stirred for 45 minutes then quenched with a dropwise addition of 1M HCl (235 mL, 0.235 mol) followed by ether (500 mL). The mixture was allowed to warm to room temperature. The organic layer was washed with 0.2M HCl, water, saturated sodium bicarbonate, and saturated sodium chloride, dried (MgSO₄), and rotoevaporated to a solid. The material was recrystallized twice from diisopropyl ether and chromatographed on silica gel (830 g, 230–400 mesh) using petroleum ether-ethyl acetate (2:1, 20×900 mL) to give a white solid; yield 40.7 g (65%), mp 106°–107° C.

EXAMPLE 129

(±)-5-Dodecyl-α-phenyl-N-(2,4,6-trimethoxyphenyl)-3-isoxazole acetamide

As described in Example 128, except the compound was prepared from 5-dodecyl-3-(phenylmethyl)isoxazole as follows:

5-Dodecyl-3-(phenylmethyl)isoxazole (a) 2-Phenylnitroethane

A mixture of (trans)-β-Nitrostyrene (50.0 g, 0.335 mol), tris(triphenylphosphine)rhodium(I) chloride (10.7 g) and benzene (500 mL) at 50° C. was shaken under hydrogen at 50 psi for 14 hours and allowed to cool. The solution was rotoevaporated, suspended in petroleum ether-ether (9:1), and gravity filtered through a plug of fluorisil (80 g)/silica gel (300 g). The filtrate was rotoevaporated to a pale yellow oil; yield (49.5 g, 98%).

¹H NMR (CDCl₃): δ7.2–7.4 (m, 5H), 4.6 (t, 2H), 3.3 (t, 2H) ppm.

(b) 5-Dodecyl-3-(phenylmethyl) isoxazole

To a room temperature stirred solution of 1-tetradecyne (29.9 g, 0.154 mol) and phenyl isocyanate (33.4 mL, 0.307 mol) in benzene (450 mL) was added dropwise a solution of 2-phenylnitroethane (35.22 g, 0.1536 mol) and triethylamine (2.15 mL, 0.0154 mol) in benzene (150 mL) over 10 minutes under nitrogen. The mixture was stirred for 1 hour then refluxed for 10 hours. The mixture was filtered and the filtrate rotoevaporated. The residue was chromatographed on silica gel (1.4 kg, 230–400 mesh) using petroleum ether-ethyl acetate (50:1, 12×1 L) to give a yellow crystalline solid; yield 20.6 g (41%), mp 41°–45° C.

The title compound was obtained; mp 90°–91° C.

EXAMPLE 130

(±)-3-Dodecyl-α-phenyl-N-(2,6-bis(1-methylethyl)phenyl)-5-isoxazole acetamide

In a manner similar to Example 128, a mixture of 3-dodecyl-α-phenyl-5-isoxazole acetic acid and 5-dodecyl-α-phenyl-3-isoxazole acetic acid was condensed with 2,6-bis(1-methylethyl)aniline to give after chromatography pure title compound; mp 115°–117° C.

Also obtained was pure (±)-5-dodecyl-α-phenyl-N-(2,6-bis(1-methylethyl)phenyl)-3-isoxazole acetamide; mp 107°–108° C.

EXAMPLE 131

(±)-5-Dodecyl-α-phenyl-N-(2,6-bis(1-methylethyl)phenyl)-5-isoxazole acetamide

As described in Example 130, the title compound was obtained; mp 107°–108° C.

EXAMPLE 132

(±)-N-(2,4,-difluorophenyl)-3-dodecyl-α-phenyl-5-isoxazole acetamide

In a manner similar to Example 128, a mixture of 3-dodecyl-α-phenyl-5-isoxazole acetic acid and 5-dodecyl-α-phenyl-3-isoxazole acetic acid was condensed with 2,4-difluoroaniline to give, after chromatography, pure title compound; mp 68°–70° C.

Also obtained was pure (±)-N-(2,4,-difluorophenyl)-3-dodecyl-α-phenyl-5-isoxazole acetamide; mp 54°–57° C.

EXAMPLE 133

(±)-N-(2,4,-difluorophenyl)-3-dodecyl-α-phenyl-5-isoxazole acetamide

As described in Example 132, the title compound was obtained; mp 54°–57° C.

EXAMPLE 134

(±)-5-Dodecyl-α-phenyl-N-(2,4,6-trimethoxyphenyl)-1,3,4-oxadiazole-2-acetamide (a) 2,4,6-Trimethoxyphenyl isocyanate A suspension of 2,4,6-trimethoxyaniline hydrochloride (71.1 g, 0.324 mol) in a 12.5% wt/wt. solution (540 mL) of phosgene in toluene was heated (95° C.) for 3 hours. Additional phosgene solution (2×270 mL) was added every hour. The mixture was allowed to cool and stirred under house vacuum for 2 days. The mixture was rotoevaporated to a solid. The solid was triturated with ether (450 mL), filtered, and the filtrate rotoevaporated to give a purple amorphous solid; yield 66.9 g (99%); mp 67°–70° C.

(b) α-[[(2,4,6-trimethoxyphenyl)amino]carbonyl]benzene acetic acid ethyl ester

To a stirred, room temperature solution of diisopropylamine (43.4 mL, 0.310 mol) in dry THF (1.2 L) was added a 2.5M solution (124 mL, 0.31 mol) of n-butyl lithium in hexanes in one portion, and the mixture was cooled to −78° C. To the solution was added under nitrogen a solution of phenylacetic acid, ethyl ester (50.8 g, 0.309 mol) in THF (500 mL) over 15 minutes. Stirred 2 minutes. To the mixture was added a solution of 2,4,6-trimethoxyphenyl isocyanate (64.9 g, 0.310 mol) in THF (500 mL) over 10 minutes. Stirred 1.5 hours. The reaction was quenched with 1M HCl (310 mL, 0.310 mol) and allowed to warm to room temperature. The mixture was rotoevaporated to remove THF and partitioned between water and chloroform. The organic layer was washed (1M HCl ; saturated NaCl), dried ($Na_2SO_4$), and rotoevaporated. The residue was chromatographed on silica gel (1.4 kg, 230–400 mesh) using petroleum ether-ethyl acetate (1:1). Fractions containing product were rotoevaporated, and the residue crystallized from ethanol-ether to give a white solid; yield 46.9 g (41%); mp 109°–111° C.

(c) α-[[(2,4,6-trimethoxyphenyl)amino]carbonyl]-benzene acetic acid

To a stirred solution of KOH (10.70 g, 0.191 mol) in absolute ethanol (1.1 L) was added α-[[(2,4,6-trimethoxyphenyl)amino]carbonyl] benzene acetic acid ethyl ester (55.28 g, 0.1480 mol), and the mixture was stirred for 41 hours. The resulting suspension was diluted with $H_2O$ (~900 mL) and rotoevaporated to remove ethanol. The solution was washed (ethyl acetate) and acidified with dropwise addition of 1M HCl (265 mL). The resulting precipitate was filtered off, washed ($H_2O$), and dried in vacuo to give an off-white solid; yield 48.4 g (100%); 111°–113° C. (gas evolution).

(d) Tridecanoic acid hydrazide

A solution of tridecanoic acid, methyl ester (24.63 g, 0.1078 mol), and anhydrous hydrazine (3.40 mL, 0.108 mol) in absolute ethanol (150 mL) was stirred at room temperature for 24 hours, then refluxed 2 days. The solution was allowed to cool, and the solid that crystallized was filtered off, washed, and dried in vacuo; yield 18.6 g (75%); mp 101°–104° C.

(e) 2-[2-oxo-1-phenyl-2-[(2,4,6-trimethoxyphenyl)amino] ethyl]tridecanoic acid hydrazide A solution of α-[[(2,4,6-trimethoxyphenyl)amino] carbonyl]-benzene acetic acid (46.73 g, 0.1353 mol), and 1,1'-carbonyldiimidazole (24.7 g, 0.152 mol) in dry THF (1.0 L) was stirred at room temperature under nitrogen for 2 hours. A white solid precipitated. To the suspension was added tridecanoic acid hydrazide (30.90 g, 0.1353 mol), and the mixture was stirred at room temperature for 17 hours, then at 40° C. for 21 hours. The mixture was chilled (+5° C.) and filtered. The filtercake was washed (THF, ether, water) and dried under house vacuum/air stream; yield 54.36 g (72%); mp 175°–180° C.

(f) (±)-5-Dodecyl-α-phenyl-N-(2,4,6-trimethoxyphenyl)-1,3,4-oxadiazole-2-acetamide To a flask charged with granular phosphorous pentoxide (470.3 g, 3.313 mol) was added dropwise over 30 minutes absolute ethanol (260 mL, 4.43 mol) under nitrogen. The mixture was stirred while heated on a steam bath (95° C.) for 3 hours, and allowed to cool. To the mixture was added 2-[2-oxo-1-phenyl-2-[(2,4,6-trimethoxyphenyl)amino] ethyl]tridecanoic acid hydrazine (53.58 g, 0.09642 mol) and dimethylformamide (700 mL), and the mixture was stirred at 95° C. for 12 hours. The resulting solution was allowed to cool, poured into water (5 L), and extracted with dichloromethane (2×1.5 L). The organic layer was washed ($H_2O$; saturated NaCl), dried ($MgSO_4$), and rotoevaporated in vacuo. The residue was dissolved ($CHCl_3$), and chromatographed on silica gel (1.5 kg, 230–400 mesh) using petroleum ether-acetone (4:1). Fractions containing pure product were rotoevaporated, and the residue crystallized from ethanol-water. The crystals were filtered off, washed, and dried in vacuo; yield 7.37 g (14%); mp 120°–121° C.

EXAMPLE 135

(f)-5-Dodecyl-α-phenyl-N-(2,6-bis (1-methylethyl)phenyl) 1,3,4-oxodiazole-2-acetamide (a) α-[[[2,6,-bis(1-methylethyl)phenyl]amino]carbonyl] benzene acetic acid ethyl ester In a manner similar to Example 134, phenylacetic acid, ethyl ester was condensed with 2,6-bis (1-methylethyl) phenyl isocyanate to give the title compound, mp 168°–170° C.

(b) α-[[[2,6-bis (1-methylethyl)phenyl)amino]carbonyl] benzene acetic acid

In a manner similar to Example 134, α-[[[2,6-bis(1-methylethyl)phenyl]amino]carbonyl]-benzene acetic acid ethyl ester was saponified with KOH in ethanol to give the title compound.

$^1$H NMR(DMSO): δ12.7 (br.s, 1H); 9.6 (s, 1H); 7.1–7.5 (m, 8H); 4.9 (s, 1H); 3.2 (br.m, 1H); 2.6 (br.m, 1H), 0.8–1.3 (m, 12H).

(c) 2-[2-oxo-1-phenyl-2-[[2,6-bis(1-methylethyl)phenyl] amino]ethyl]tridecanoic acid hydrazine In a manner similar to Example 134, α-[[[2,6-bis (1-methylethyl)phenyl]amino]carbonyl]-benzene acetic acid was condensed with tridecanoic hydrazide to give the title compound; mp 182°–184° C.

(d) (+)-5-Dodecyl-α-phenyl-N-(2,6-bis (1-methylethyl) phenyl)-1,3,4-oxadiazole-2-acetamide In a manner similar to Example 134, 2-[2-oxo-1-phenyl-2-[[2,6-bis(1-methylethyl)phenyl]amino]ethyl]tridecanoic acid hydrazine was cyclodehydrated to give the title compound; mp 82°–84° C.

EXAMPLE 136

2-Tridecyl-N-(2,4,6-trimethoxyphenyl)-4-thiazoleacetamide (a) Tetradecanamide

Ammonia was bubbled continuously into a 50° C. solution of benzene (100 mL). Myristoyl chloride (10 mL) in benzene (50 mL) was added dropwise. After addition was complete, ammonia was bubbled in for 5 minutes. The mixture was allowed to cool to room temperature, and filtered to yield a white solid (8.7 g, 96%).

$^1$H NMR 90 MHz: δ7.4 ppm (s, 2H); 2.1 (t, 2H); 1.3 (s, 20H); 0.9 (t, 3H).

(b) Tetradecanethioamide

Phosphorus pentasulfide (9.8 g, 0.044 mol) was added to a mixture of tetradecanamide (8.6 g, 0.04 mol) in dry THF (250 mL) and the mixture refluxed overnight, concentrated in vacuo, and heated with methanol (200 mL), filtered, and the filtrate concentrated in vacuo to yield a pale yellow solid (10.28 g, 99%) used without further purification.

$^1$H NMR 90 MHz: δ9.0 ppm (s br, 2H); 2.3 (t, 2H); 1.5 (m, 2H); 1.1 (s, 18H); 0.7 (t, 3H).

(c) Ethyl 2-tridecyl-4-thiazole acetate

A mixture of tetradecanethioamide (4.0 g, 17.4 mmol), ethylchloroacetoacetate (4.7 mL, 35.0 mmol) and ethanol (100 mL) was refluxed for 2 hours. The mixture was then concentrated, diluted with water (100 mL) and triethylamine (5 mL) extracted with ethyl acetate (200 mL), washed with brine, dried (MgSO$_4$), filtered concentrated, and columned on silica gel eluting with 5% ethyl acetate in hexanes to yield 2.2 g, 36% of ester.

$^1$H NMR 250 MHz: δ7.04 (s, 1H); 2.32 (q, 2H); 3.81 (s, 2H); 2.99 (t, 2H); 1.77 (m, 2H); 1.25 (m, 23H); 0.88 (t, 3H).

(d) 2-tridecyl-4-thiazole acetic acid

Ethyl-2-tridecyl-thiazole acetate (2.13 g, 6.35 mmol) and potassium hydroxide (0.39 g, 6.98 mmol) were refluxed overnight in ethanol (200 mL). The mixture was then acidified with 1M HCl and the precipitate filtered to give a solid which was dissolved in ethyl acetate and washed with brine, dried (MgSO$_4$), filtered concentrated, and triturated with hexanes. The solid was filtered and air dried to yield 0.75 g, 37%. % C,H,N(found): C, 66.16; H, 9.50; N 3.99.

(e) 2-tridecyl-N-(2,4,6-trimethoxyphenyl)-4-thiazole acetamide

Carbonyl dimidazole (0.38 g, 2.35 mmol) was added to a solution of 2-tridecyl-4-thiazole acetic acid (0.71 g, 2.28 mmol) in dry THF (50 mL), and the resulting mixture was stirred at room temperature for 1.5 hours, then 2,4,6-trimethoxyaniline made in situ [2,4,6-trimethoxyaniline.HCl (0.05 g, 2.28 mmol) and triethylamine (0.32 mL, 2.28 mmol) were stirred together at room temperature for 0.5 hour] was added and the solution stirred for 3 days at room temperature, then filtered, and the filtrate stirred with 3:1 chloroform/water (200 mL) for 1 hour. She organic layer was separated, washed with brine, dried over Na$_2$SO$_4$, filtered, concentrated, and triturated with hexanes to yield a grey solid (0.93 g, 82%) which was air dried.

$^1$H NMR 250 MHz: δ7.86 ppm (s, 1H); 7.09 (s, 1H); 6.14 (s, 2H); 3.85 (d, 2H); 3.80 (s, 3H); 3.77 (s, 6H); 3.00 (t, 2H); 1.79 (m, 2H); 1.25 (s, 20H); 0.88 (t, 3H).

EXAMPLE 137

(±)-5-Dodecyl-α-phenyl-N-(2,4,6-trimethoxyphenyl)-1,2,4-oxadiazide-3-acetamide (a) α-cyano-N-(2,4,6-trimethoxyphenyl)-benzene acetamide Phenylacetonitrile (2.64 mL, 22.8 mol) was added dropwise to an ice-cooled solution of sodium hydride (0.91 g, 22.8 mmol) in dimethyl formamide (50 mL), and the mixture stirred for 15 minutes while allowing to warm to room temperature. 2,4,6-Trimethoxyphenyl-isocyanate (4.78 g, 22.8 mmol) was added portionwise over 2 minutes, and then the mixture was stirred vigorously for 0.5 hour and poured into water (200 mL). The solid obtained was washed with water (100 mL) and taken up in chloroform (1 n). The organic layer was separated and dried with MgSO$_4$, filtered, and concentrated to yield a pale purple solid (6.13 g, 82%). % (found): C, 65.94; H, 5.56; N, 8.10.

(b) α-[(hydroxyamino)iminomethyl]-N-(2,4,6-trimethoxyphenyl)-benzeneacetamide

Hydroxylamine hydrochloride (11.95 g, 0.17 mol) was added to a solution of triethylamine (23.9 mL, 0.17 mol) in 50% ethanol/water (40 mL), and the mixture was stirred with ice, cooling until the NH$_2$OH.HCl dissolved (0.5 hour). The mixture was then diluted with ethanol (300 mL) and α-cyano-N-(2,4,6-trimethoxyphenyl)-benzene acetamide (44.9 g, 0.138 mol) added in one portion and the mixture refluxed for 8 hours, allowed to cool, and poured into water (2 L) to yield a 2-phase oil/water mixture. The aqueous phase was concentrated in vacuo and the precipitate collected. The oil phase was triturated with chloroform to yield a white solid which was combined with the previous lot to yield 33.6 g, 68%, % (found): C, 60.35; H, 6.11; N, 11.60.

(c) (±)-5-Dodecyl-α-phenyl-N-(2,4,6-trimethoxyphenyl)-1,2,4-oxadiazole-3-acetamide Tridecanoyl chloride (15.08 g, 0.061 mol) was added to a mixture of α-[(hydroxyamino) iminomethyl]-N-(2,4,6-trimethoxyphenyl)-benzene acetamide (19.8 g, 0.055 mol), Hunig's base (10.6 mL, 0.061 mol), and THF (200 mL). The mixture was stirred in THF at room temperature for 2 hours, then concentrated in vacuo and dissolved in glacial acetic acid (50 mL) and refluxed for 2 hours, then concentrated in vacuo, azeotroped with toluene (2×250 mL), and columned on silica gel eluting with 35% ethyl acetate in hexanes to yield a white solid (12.1 g, 62%). % (found): C, 68.93; H, 7.96; N, 7.54.

EXAMPLE 138

(±)-3-Dodecyl-α-phenyl-N-(2,4,6-trimethoxyphenyl)-1,2,4-oxadiazole-5-acetamide (a) N-hydroxy-tridecaneimidamide Hydroxylamine hydrochloride (0.90 g, 12.9 mmol) was added to a solution of triethylamine (1.79 mL, 12.9 mmol) in 50% ethanol/water (4 mL) and the mixture was stirred for 2 minutes. Tridecane nitrile (2.02 g, 10.4 mmol) in ethanol (10 mL) was added and the mixture refluxed for 2 hours, allowed to cool, and poured into water (50 mL). The precipitate was collected, stirred with hexanes, and filtered to yield a white solid (0.63 g, 26%). EI$^+$ 229, 196, 85, 74.

(b) (±)-3-Dodecyl-α-phenyl-N-(2,4,6-trimethoxyphenyl)-1,2,4-oxadiazole-5-acetamide Carbonyl dimidazole (0.28 g, 1.71 mmol) was added to a solution of α-[[(2,4,6-trimethoxyphenyl)amino]carbonyl]- benzene acetic acid (0.56 g, 1.63 mmol) in dry THF (20 mL), and the resulting mixture was stirred at room temperature for 1 hour, then N-hydroxy-tridecane imidamide (0.37 g, 1.63 mmol) was added, and the mixture stirred for 1.5 hours, concentrated in vacuo, dissolved in glacial acetic acid, and refluxed for 1.5 hours. The solution was concentrated and azeotroped with benzene (2×25 mL), dissolved in ethyl acetate, and washed with NaHCO$_3$, water, brine, dried with MgSO$_4$, and recrystallized from ethanol/water to yield a white solid (0.093 g, 11%). (found): C, 69.25; H, 8.08; N, 7.68.

CHART I (n = 0 and R$_2$ = R$_3$ = H, R$_1$ and R$_4$ as defined in Formula I)

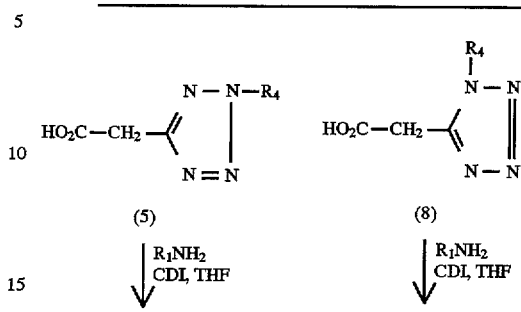

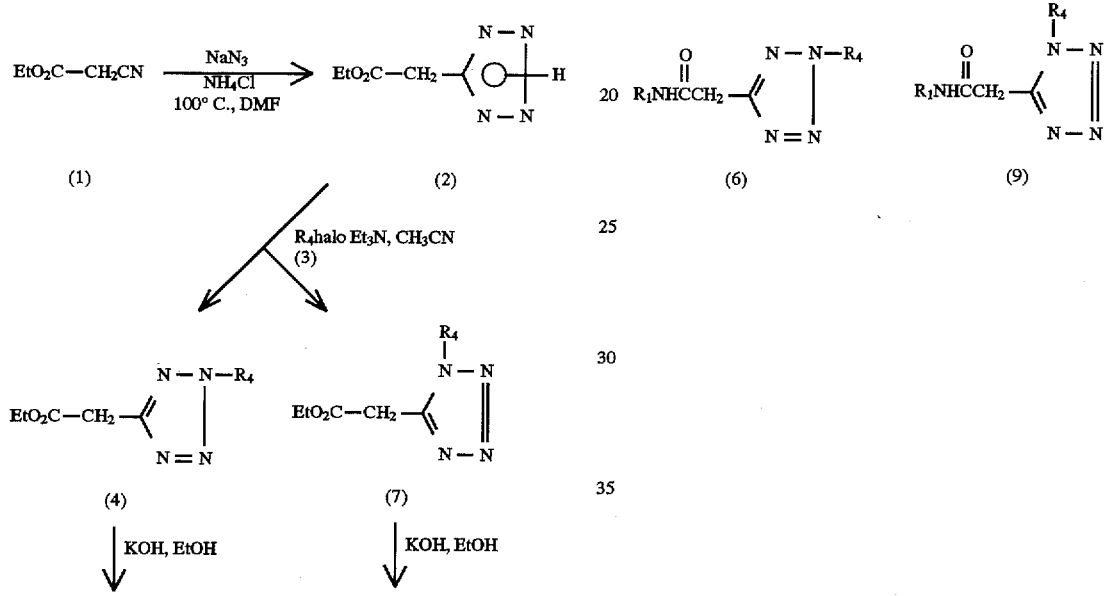

CHART II (n = 0, R$_1$, R$_2$, R$_3$, and R$_4$ as defined in Formula I.

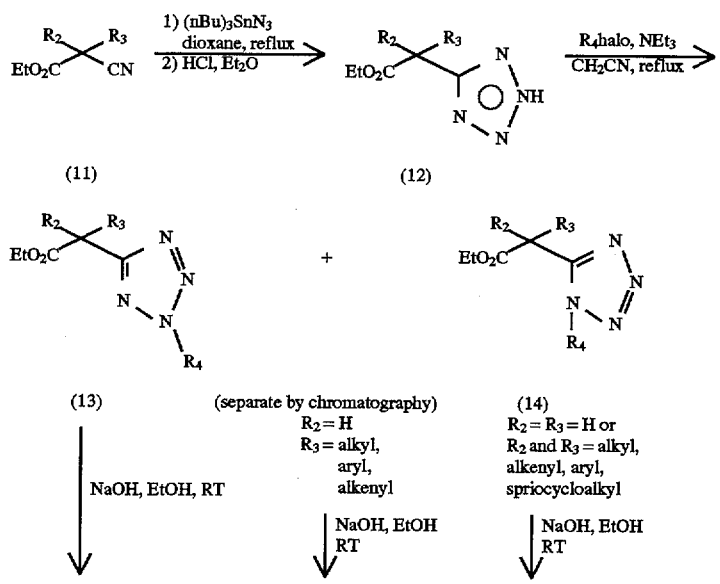

-continued
CHART II
(n = 0, $R_1$, $R_2$, $R_3$, and $R_4$ as defined in Formula I.

(15), (17), (19) → (16), (18)

Reagents: $R_1NH_2$, CDI, THF, RT; n-BuLi, THF, -20° C. $R_1$NCO; $R_1NH_2$, CDI, THF, RT

CHART II(a)
($R_2$ = H, $R_3$ as defined in Formula I, except for aryl or heteroaryl)

(15) → 1. nBuLi/THF -78° C. 2. $R_2X$ → intermediate → $R_1NH_2$/CDI/THF → product

CHART III
(n = 1 or 2, $R_2 = R_3$ = H, $R_1$ and $R_4$ as defined in Formula I)

(20) $CH_3OCCH_2(CH_2)_nCN$ → $NaN_3$, $NH_4Cl$/DMF → (20-A)

↓ $R_4$ halo / $CH_3CN$, $Et_3N$ (21), (22)

↓ KOH, EtOH

CHART III (continued)
(n = 1 or 2, $R_2 = R_3$ = H, $R_1$ and $R_4$ as defined in Formula I)

(23), (24) → $R_1NH_2$/CDI → (25), (26)

CHART IV
(n = 1, $R_2$ = H, $R_3$ = phenyl, subt. phenyl, alkyl, alkenyl, heteroaryl and $R_1$ and $R_4$ as defined in Formula I)

(27) $R_3$—CH—$CH_2$COOH with CN → $R_1NH_2$/DCC/$CH_2Cl_2$ → (28) $R_3$—CH—$CH_2$—C(=O)—$NHR_1$ with CN 1) $(nBu)_3SnN_3$ dioxane
2) HCl, $Et_2O$

CHART IV
(n = 1, $R_2$ = H, $R_3$ = phenyl, subt. phenyl,
alkyl, alkenyl, heteroaryl and $R_1$ and $R_4$ as defined in Formula I)
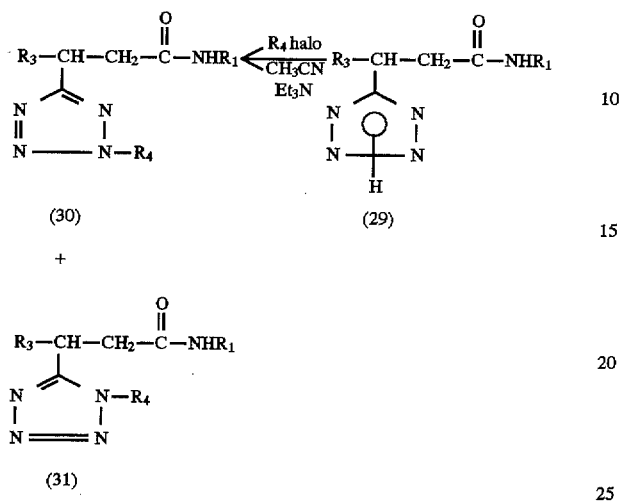
CHART V
(n = 2, $R_2$ = H, $R_3$ = phenyl or substituted phenyl,
$R_1$ and $R_4$ as defined in Formula I)
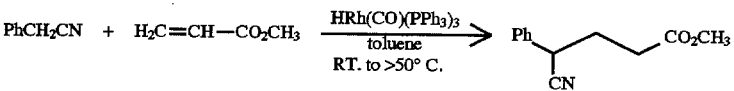
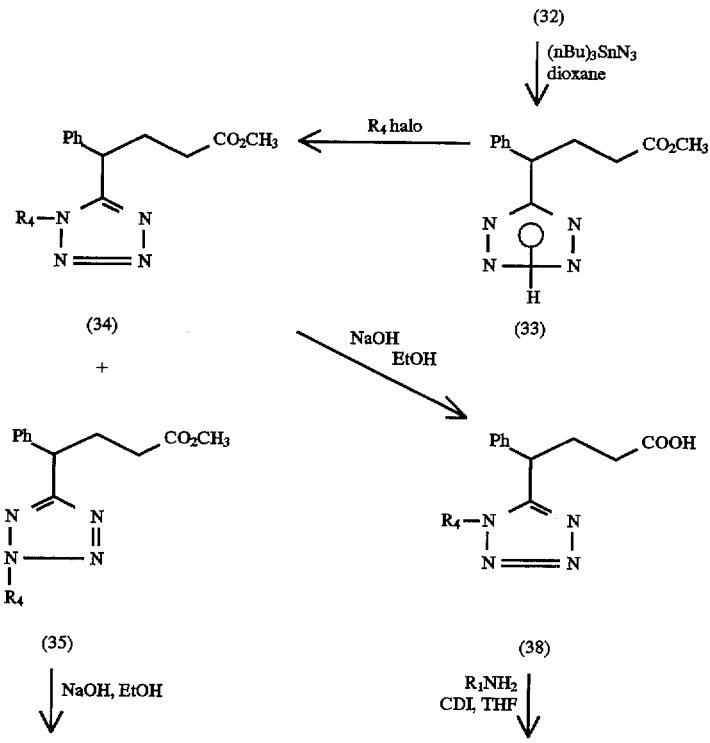

CHART V
(n = 2, R₂ = H, R₃ = phenyl or substituted phenyl, R₁ and R₄ as defined in Formula I)
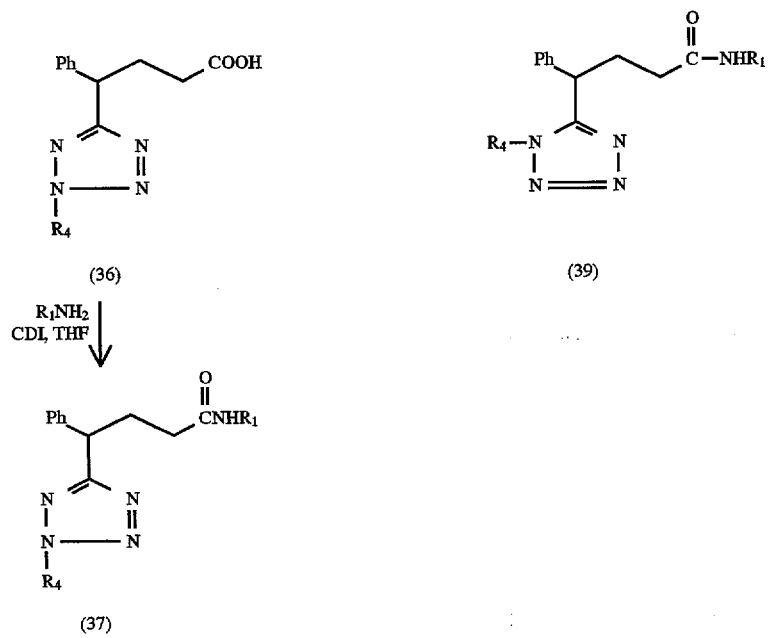
CHART VI
(n = 0, R₃ is heteroaryl, 1- or 2-naphthyl, substituted phenyl, and R₁ and R₄ are as defined in Formula I)
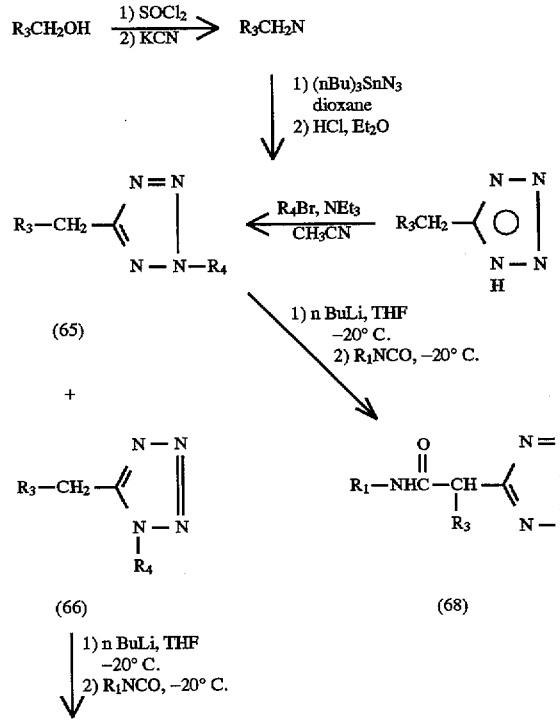
(67)
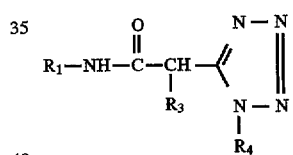
CHART VII
(n = 1, R₁, R₂, R₃, and R₄ are as defined in Formula I)
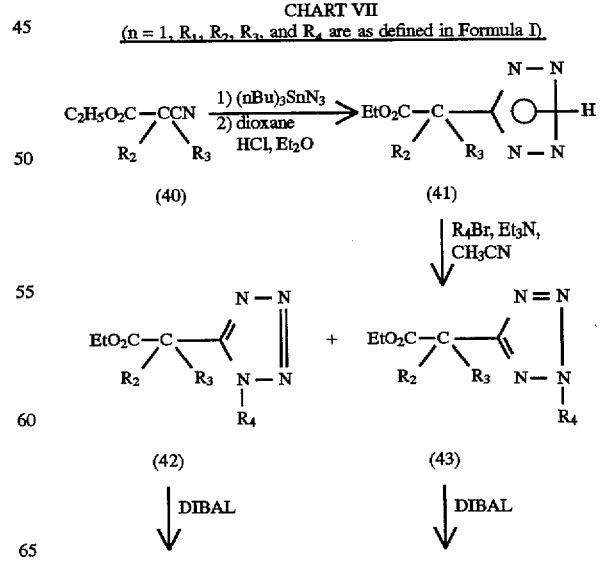

CHART VII
(n = 1, R₁, R₂, R₃, and R₄ are as defined in Formula I)
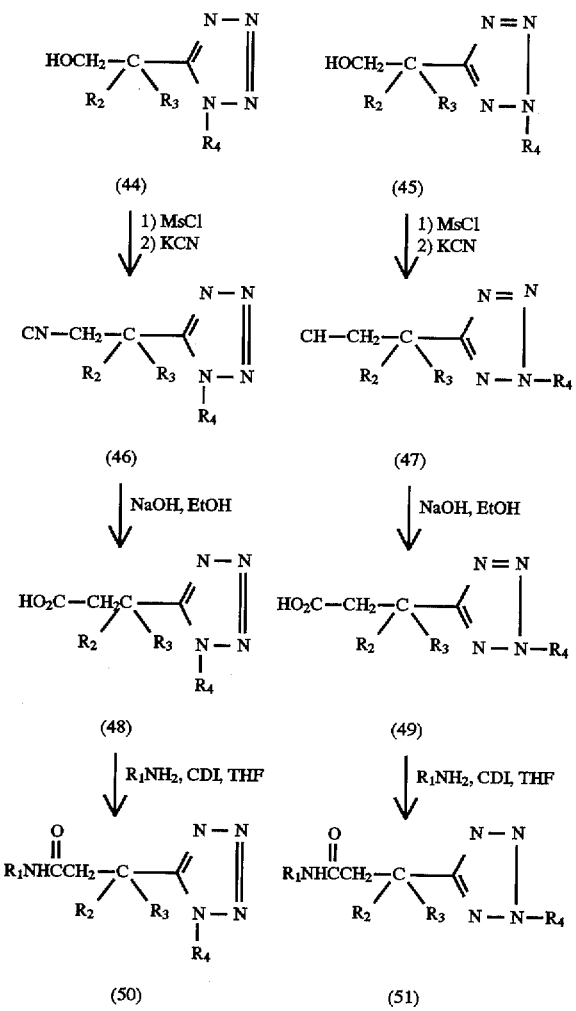
CHART VIII
(n = 1, R₃ is heteroaryl and R₁, R₂, and R₄ are as defined in Formula I)
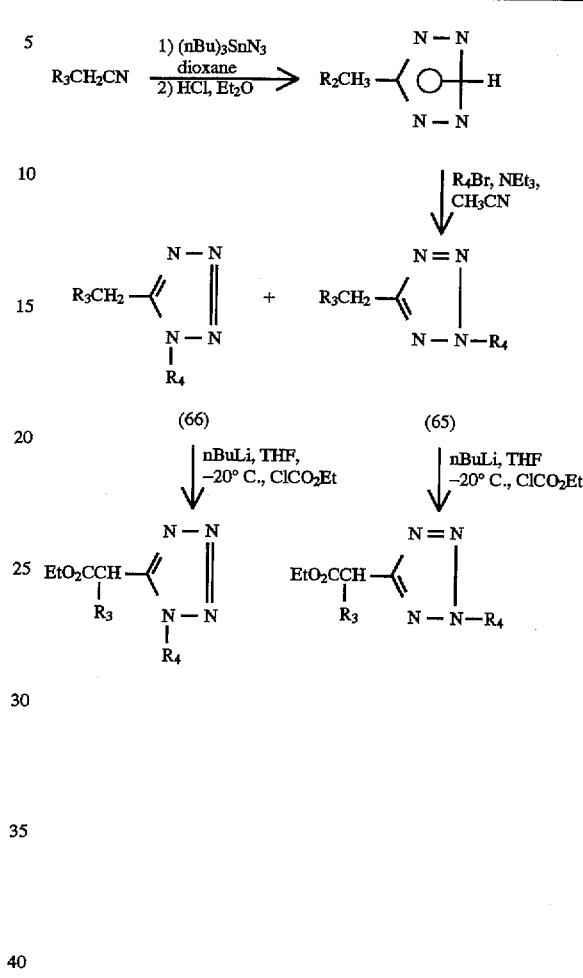
CHART IX
(n = 2, R₂ and R₃ are as defined in Formula I only at least one is other than hydrogen and R₁ and R₄ are as defined in Formula I)
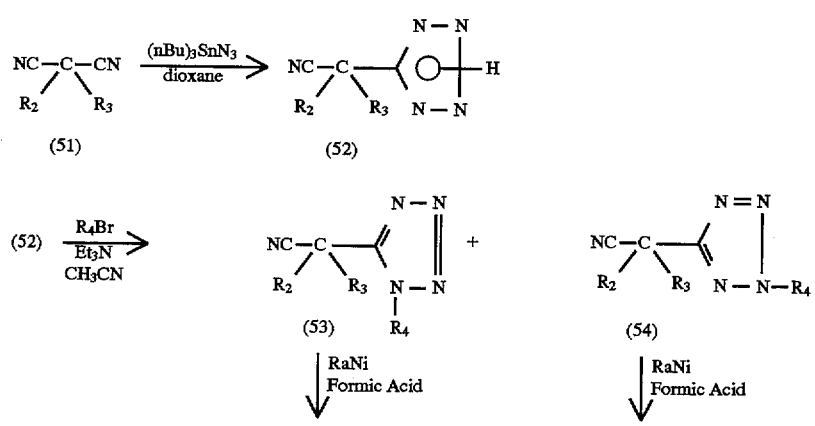

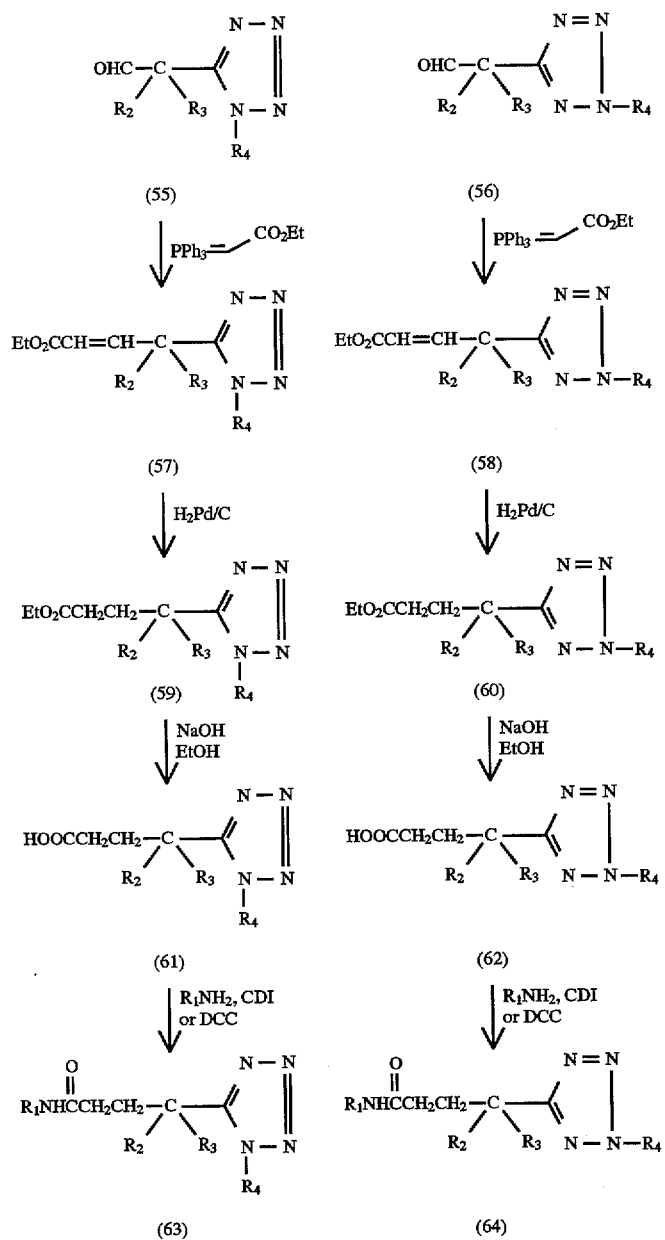

CHART X
(R$_8$, R$_9$, R$_{10}$ as defined in Formula I)
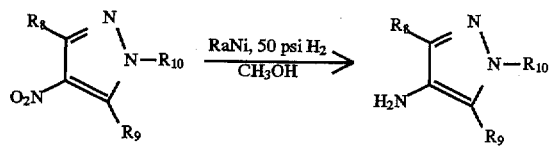
CHART XI
(n = 0, R$_2$, R$_3$ = alkyl, aryl, R$_1$, R$_4$ as defined in Formula I)
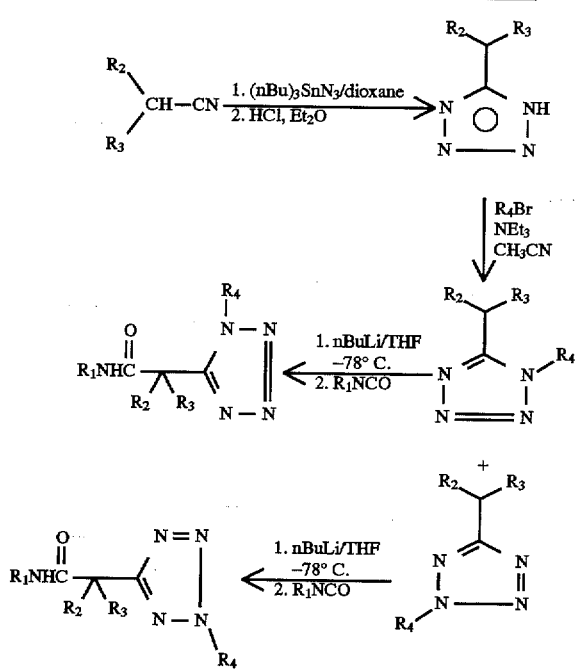
CHART XII
(R$_1$, R$_2$, and R$_4$ as defined in Formula I; and/or R$_3$ is F or OH, n is 0)
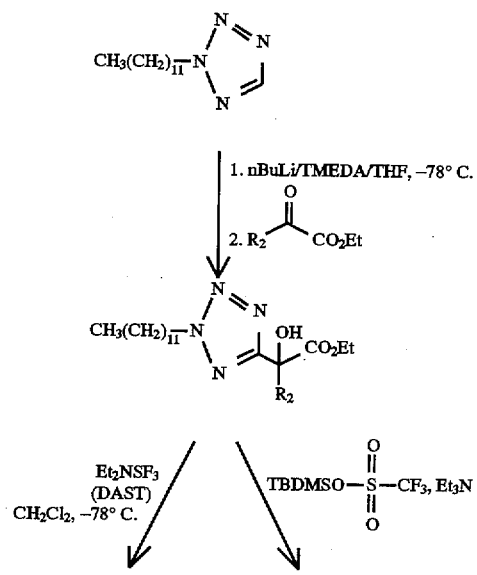
CHART XII -continued
(R$_1$, R$_2$, and R$_4$ as defined in Formula I; and/or R$_3$ is F or OH, n is 0)
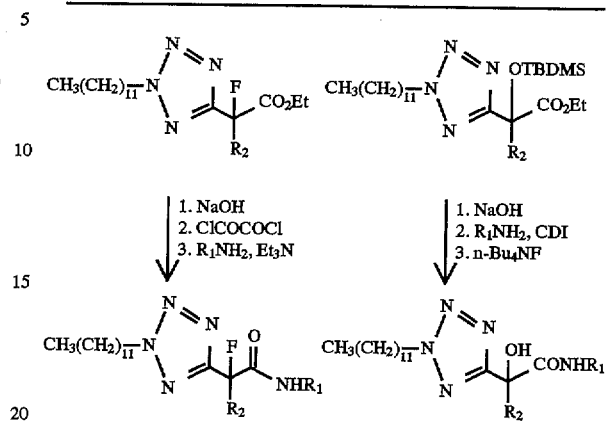
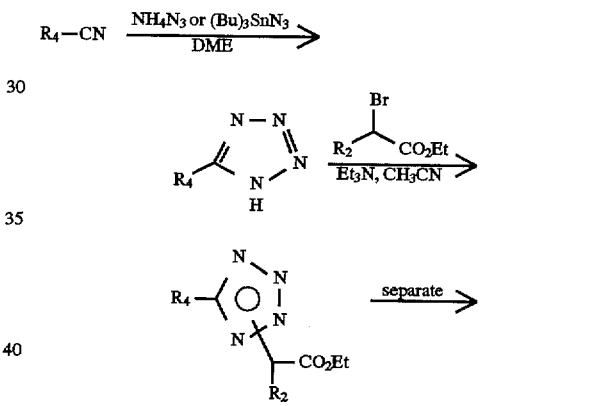
CHART XIII
(compounds of Formula I where side chain is attached to a nitrogen atom of the tetrazole ring)
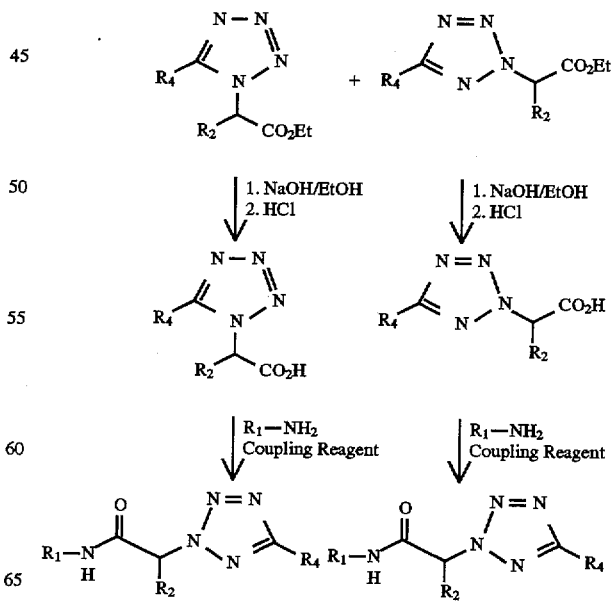

CHART XIV
(n = 0, X is pyrazole, and $R_1$, $R_2$, $R_3$, and $R_4$ are as defined in Formula I)
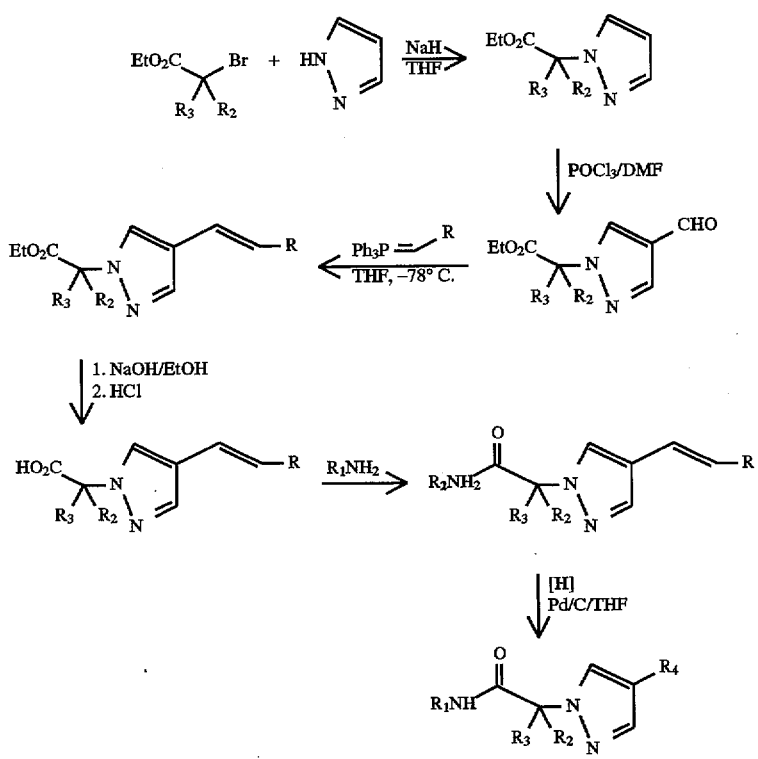
CHART XV
(n = 0, X is imidazole, and $R_1$, $R_2$, $R_3$, and $R_4$ are as defined in Formula I)
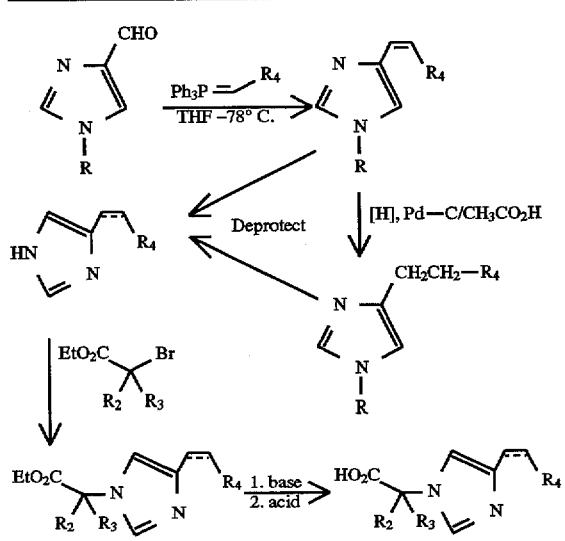
CHART XVI
(n = 0, X is 1,2,3-triazole, and $R_1$, $R_2$, $R_4$ are as defined in Formula I)
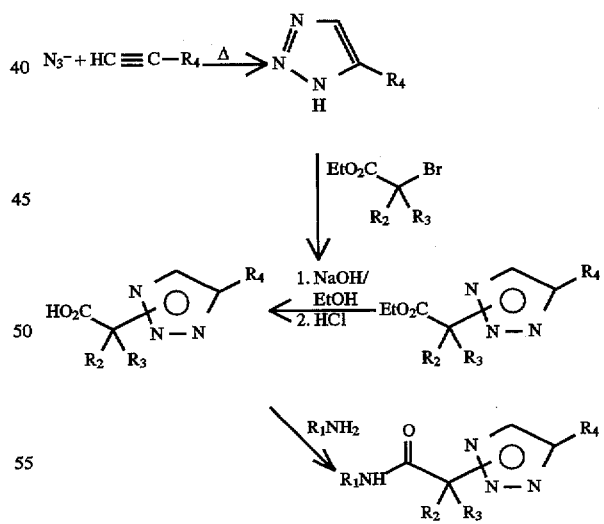
CHART XVII
(n = 0, X is isoxazole, $R_2$ and $R_3$ are hydrogen, and $R_1$ and $R_4$ are as defined in Formula I)

-continued
CHART XVII
(n = 0, X is isoxazole, $R_2$ and $R_3$ are hydrogen,
and $R_1$ and $R_4$ are as defined in Formula I)
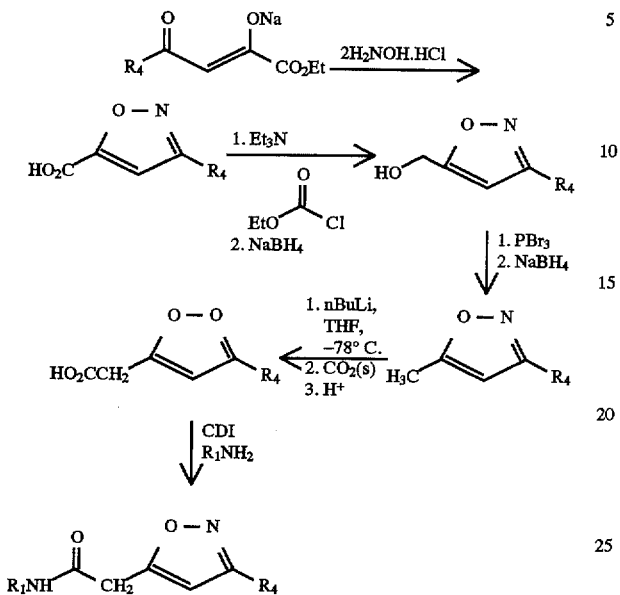
CHART XVIII
(n = 0, X is isoxazole, $R_3$ is hydrogen, and $R_1$,
and $R_2$, and $R_4$ are as defined in Formula I)
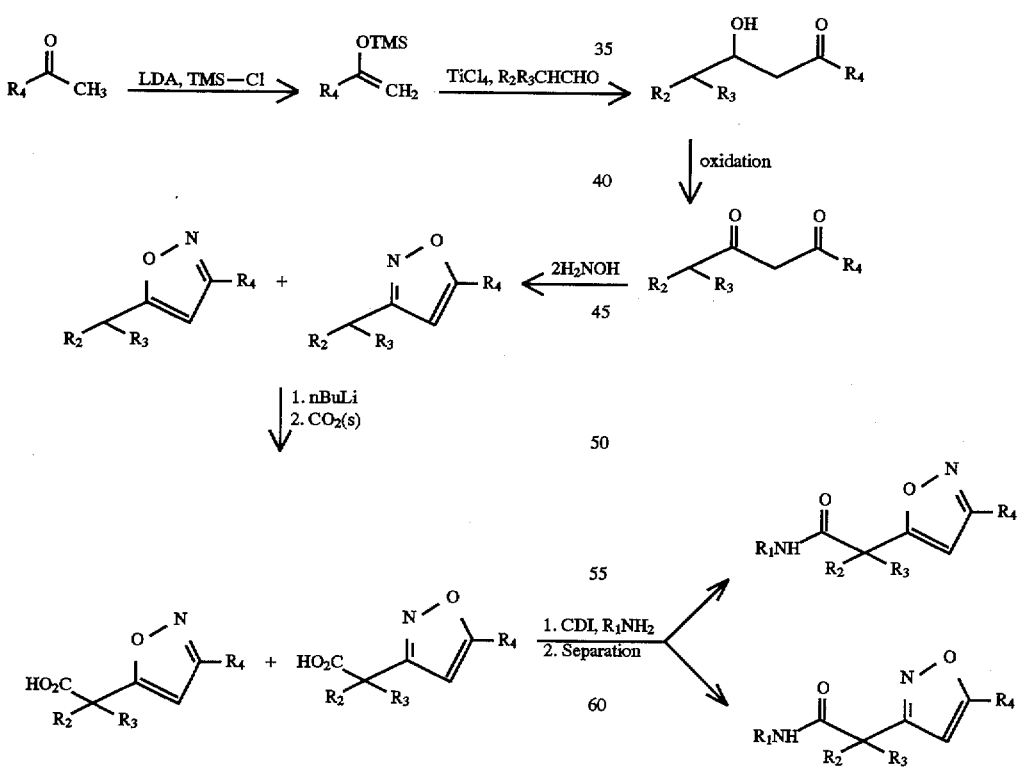

CHART XVIIIa
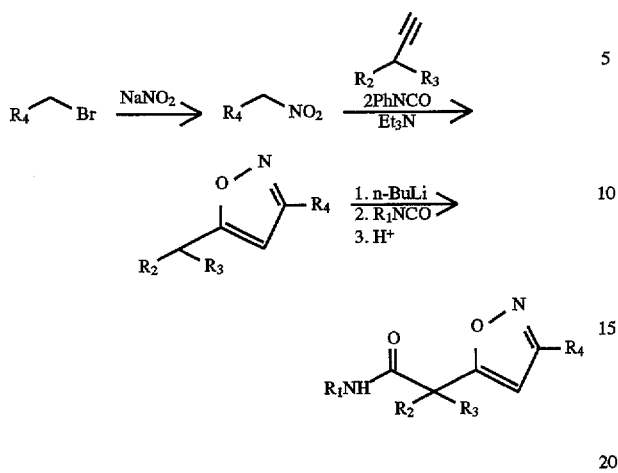
CHART XVIIIb
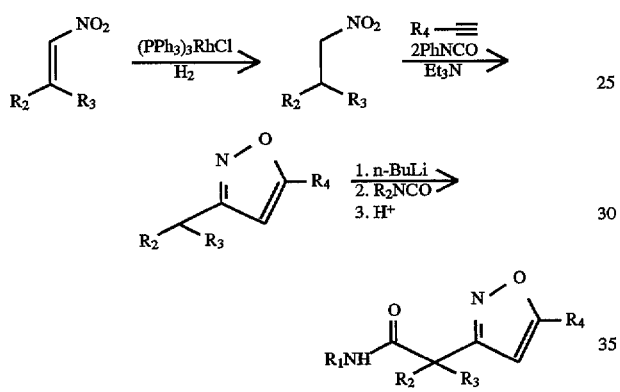
CHART XIX
(n = 0, X is 1,3,4-oxadiazole, $R_3$ is hydrogen, and $R_1$, $R_2$, and $R_4$ are as defined in Formula I)
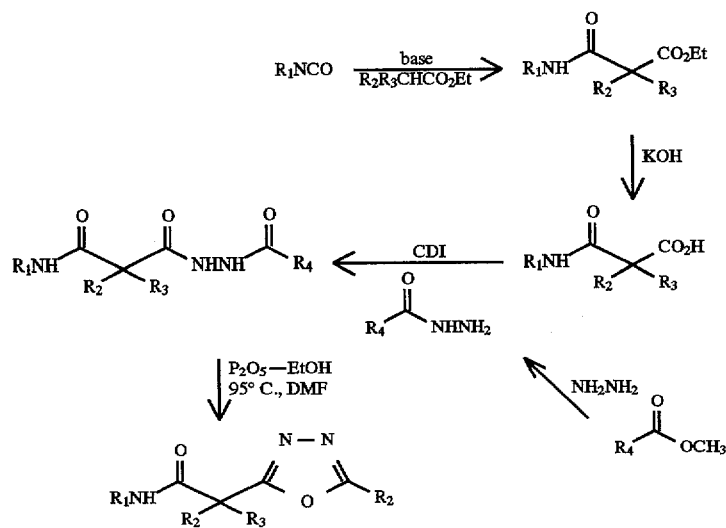

CHART XX
(n = 0, X is thiazole, $R_2$ and $R_3$ are hydrogen, and $R_1$ and $R_4$ are as defined in Formula I)

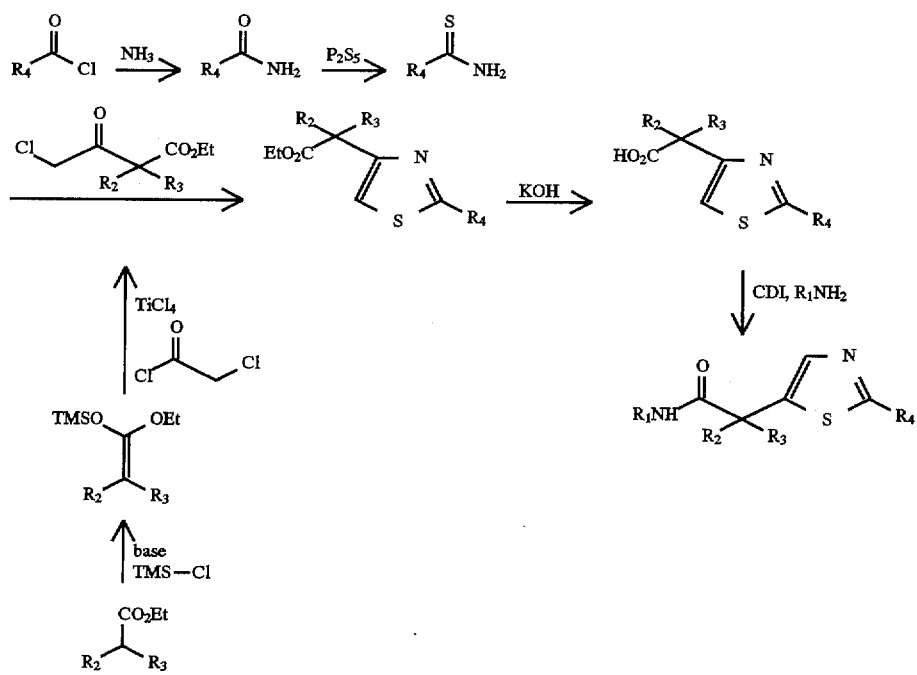

CHART XXIa
(n = 0, X is 1,2,4-oxadiazole, $R_3$ is hydrogen, and $R_1$, $R_2$, and $R_4$ are as defined in Formula I)

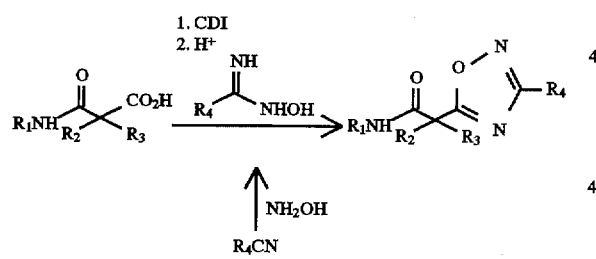

CHART XXIb
(n = 0, X is 1,2,4-oxadiazole, $R_3$ is hydrogen, and $R_1$, $R_2$, and $R_4$ are as defined in Formula I)

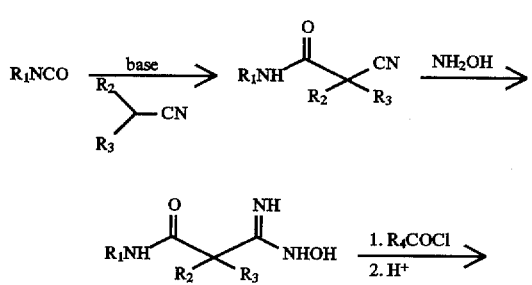

-continued
CHART XXIb
(n = 0, X is 1,2,4-oxadiazole, $R_3$ is hydrogen, and $R_1$, $R_2$, and $R_4$ are as defined in Formula I)

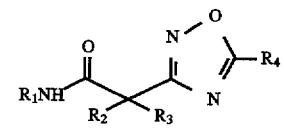

CHART XXII
(n = 0, X is imidazole, $R_2$ and $R_3$ are hydrogen, and $R_1$ and $R_4$ are as defined in Formula I)

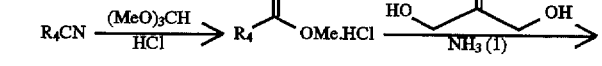
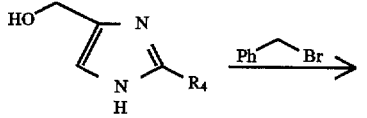
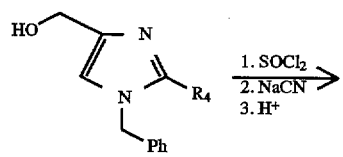

CHART XXII (n = 0, X is imidazole, $R_2$ and $R_3$ are hydrogen, and $R_1$ and $R_4$ are as defined in Formula I)

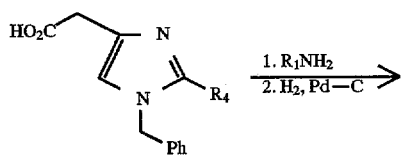
$\xrightarrow[\text{2. H}_2, \text{Pd—C}]{\text{1. R}_1\text{NH}_2}$

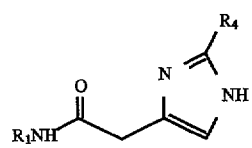

CHART XXIII (n = 0, X is imidazole, $R_3$ is hydrogen, and $R_1$, $R_2$, and $R_4$ are as defined in Formula I)

$R_4CN \xrightarrow[\text{HCl}]{\text{(MeO)}_3\text{CH}}$ 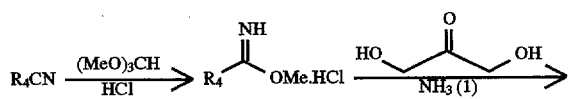 $\xrightarrow[\text{NH}_3(l)]{}$

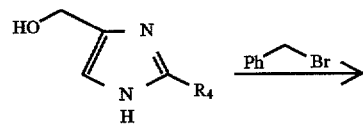 $\xrightarrow{\text{Ph}\frown\text{Br}}$

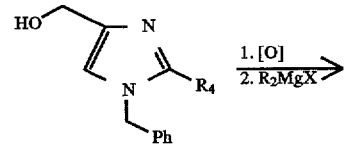 $\xrightarrow[\text{2. R}_2\text{MgX}]{\text{1. [O]}}$

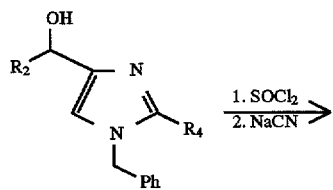 $\xrightarrow[\text{2. NaCN}]{\text{1. SOCl}_2}$

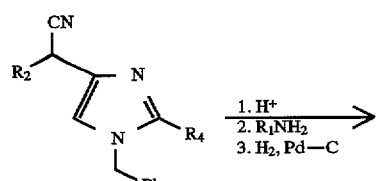 $\xrightarrow[\substack{\text{2. R}_1\text{NH}_2 \\ \text{3. H}_2, \text{Pd—C}}]{\text{1. H}^+}$

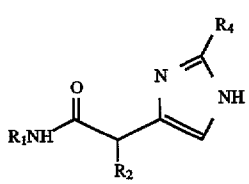

CHART XXIV (n = 0, X is oxazole, $R_3$ is hydrogen, and $R_1$, $R_2$, and $R_4$ are as defined in Formula I)

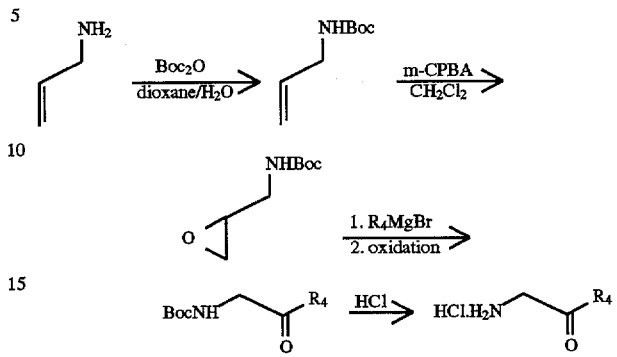

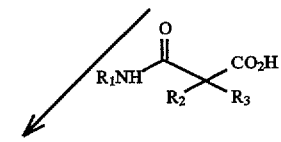 $\xrightarrow[\text{2. oxidation}]{\text{1. R}_4\text{MgBr}}$

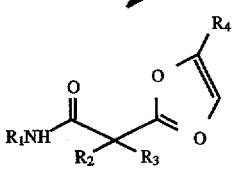 $\xrightarrow{\text{HCl}}$ (HCl·H₂N-CH₂-C(O)-R₄)

$\downarrow$

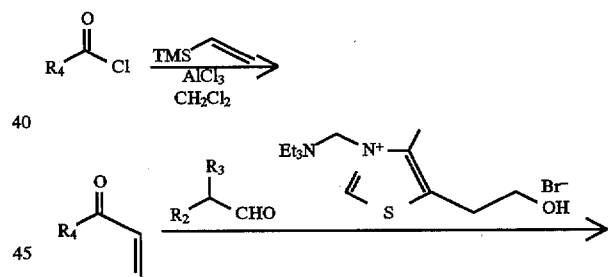

CHART XXV (n = 0, X is thiophene, $R_3$ is hydrogen, and $R_1$, $R_2$, and $R_4$ are as defined in Formula I)

$R_4\text{COCl} \xrightarrow[\text{CH}_2\text{Cl}_2]{\substack{\text{TMS} \\ \text{AlCl}_3}}$

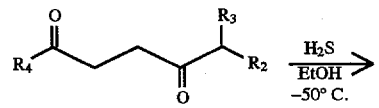 $\xrightarrow[\substack{\text{EtOH} \\ -50°\text{C.}}]{\text{H}_2\text{S}}$

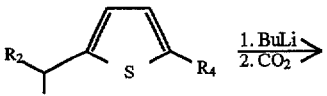 $\xrightarrow[\text{2. CO}_2]{\text{1. BuLi}}$

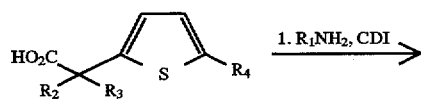 $\xrightarrow{\text{1. R}_1\text{NH}_2, \text{CDI}}$

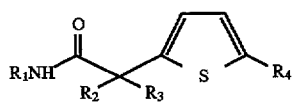

CHART XXVI (n = 0, X is pyrrole, $R_3$ is hydrogen, and $R_1$, $R_2$, and $R_4$ are as defined in Formula I)

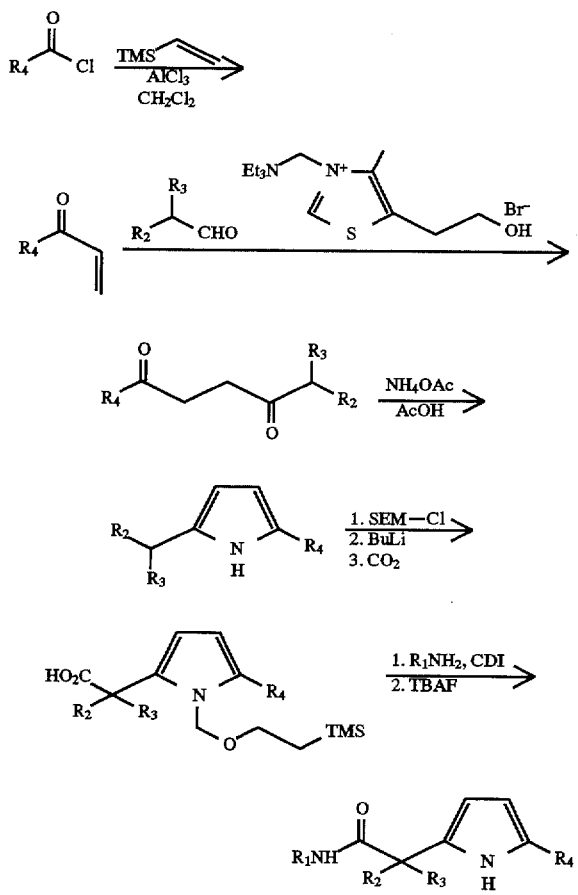

CHART XXVII (n = 0, X is furan, $R_3$ is hydrogen, and $R_1$, $R_2$, and $R_4$ are as defined in Formula I)

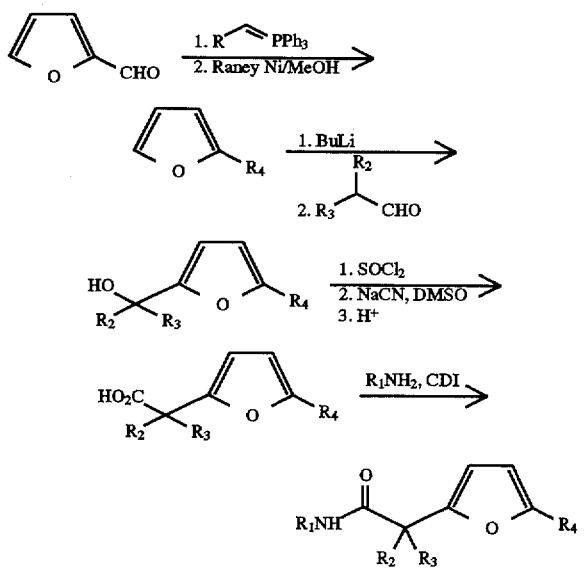

CHART XXVIII (n = 0, X is 1,3,4-thiadiazoles, $R_3$ is hydrogen, and $R_1$, $R_2$, and $R_4$ are as defined in Formula I)

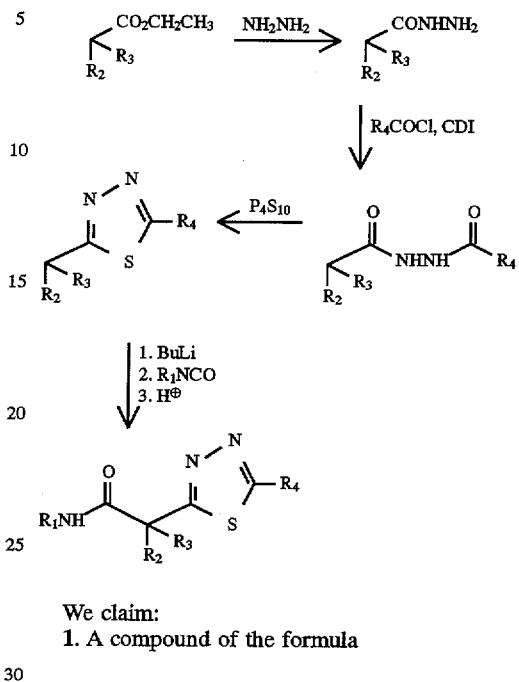

We claim:
1. A compound of the formula

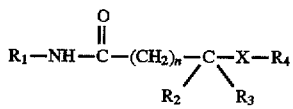

wherein n is 0, 1, or 2;
wherein $R_1$ is selected from
  (a) phenyl which is substituted with from one to three substituents selected from:
    alkyl having from one to four carbon atoms and which is straight or branched,
    alkoxy having from one to three carbon atoms and which is straight or branched,
    alkylthio having from one to three carbon atoms and which is straight or branched,
    hydroxy,
    phenyl,
    fluorine,
    chlorine,
    bromine,
    nitro,
    cyano,
    trifluoromethyl,
    —COOH,
    —COOalkyl wherein alkyl has from one to four carbon atoms and which is straight or branched,
    —$(CH_2)_m NR_5 R_6$ wherein m is 0 or 1, and each of $R_5$ and $R_6$ is hydrogen or a straight or branched alkyl group having one to four carbon atoms;
  (b) 1- or 2-naphthyl which is unsubstituted or substituted with one to three substituents selected from:
    alkyl having from one to four carbon atoms and which is straight or branched,
    alkoxy having from one to three carbon atoms and which is straight or branched,
    hydroxy,
    fluorine, chlorine,
bromine,
nitro,
cyano,
trifluoromethyl,
—COOH,
—COOalkyl wherein alkyl has from one to four carbon atoms and is straight or branched,
—$(CH_2)_m NR_5 R_6$ wherein m, $R_5$, and $R_6$ have the meanings defined above;

(c) a straight or branched hydrocarbon group having from one to 18 carbon atoms which is saturated or is unsaturated containing one double bond or two nonadjacent double bonds; or (d) a cycloalkyl group having from three to eight carbon atoms;

$R_2$ is hydrogen;

$R_3$ is a heteroaryl selected from a 5- or 6-membered monocyclic or fused bicyclic heterocyclic group containing at least one to four heteroatoms in at least one ring, said heteroatoms being nitrogen, oxygen, or sulfur and combinations thereof, said heterocyclic group being unsubstituted or substituted with an alkyl group having from one to four carbon atoms and the N-oxides thereof;

wherein x is tetrazole;

wherein $R_4$ is a straight or branched hydrocarbon chain having from 12 to 20 carbon atoms and is saturated or is unsaturated and has one double bond or has two nonadjacent double bonds or is alkyl substituted with trifluoromethyl; and $R_4$ is in the two position of the tetrazole ring and the side chain,

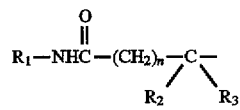

is attached to the carbon atom of the tetrazole ring or a pharmaceutically acceptable salt or individual enantiomeric isomer thereof.

2. A compound of claim 1 wherein n is 0.

3. A compound of claim 1 wherein n is 1 or 2.

4. A compound of claim 1 wherein $R_4$ is a saturated hydrocarbon chain and has from 12 to 18 carbon atoms.

5. A compound of claim 4 wherein $R_1$ is substituted phenyl.

6. A compound of claim 1 wherein $R_3$ is 2-, 3-, or 4-pyridyl.

7. A compound of claim 1 wherein $R_1$ is 2,6-(1-methylethyl)phenyl or 2,4,6-trimethoxyphenyl.

8. A compound of claim 1 which is (±)-2-dodecyl-α-(2-pyridyl)-N-(2,4,6-trimethoxyphenyl)-2H-tetrazole-5-acetamide, or (±)-N-[2,6-Bis(1-methylethyl)phenyl]-2-dodecyl-α-2-pyridinyl-2H-tetrazole-5-acetamide.

9. A pharmaceutical composition useful for treating hypercholesterolemia or atherosclerosis in a mammal comprising an effective amount of a compound of claim 1 together with a pharmaceutically acceptable carrier.

10. A method of treating hypercholesterolemia or atherosclerosis in a patent in need thereof which comprises administering to said patient a compound according to claim 1.

* * * * *